(12) United States Patent
Cuero Rengifo et al.

(10) Patent No.: US 10,995,345 B2
(45) Date of Patent: May 4, 2021

(54) BIOLOGICAL DEVICES FOR PRODUCING OXIDIZED ZINC AND APPLICATIONS THEREOF

(71) Applicants: BIOCAPITAL HOLDINGS, LLC, Houston, TX (US); Raul Cuero Rengifo, Cypress, TX (US); Juliana Londono Murillo, Manizales (CO)

(72) Inventors: Raul Cuero Rengifo, Cypress, TX (US); Juliana Londono Murillo, Manizales (CO)

(73) Assignee: BIOCAPITAL HOLDINGS, LLC, Houston, TX (US)

( * ) Notice: Subject to any disclaimer, the term of this patent is extended or adjusted under 35 U.S.C. 154(b) by 0 days.

(21) Appl. No.: 16/646,220

(22) PCT Filed: Sep. 12, 2018

(86) PCT No.: PCT/US2018/050573
§ 371 (c)(1),
(2) Date: Mar. 11, 2020

(87) PCT Pub. No.: WO2019/055457
PCT Pub. Date: Mar. 21, 2019

(65) Prior Publication Data
US 2020/0270641 A1    Aug. 27, 2020

Related U.S. Application Data

(60) Provisional application No. 62/650,356, filed on Mar. 30, 2018, provisional application No. 62/557,340, filed on Sep. 12, 2017.

(51) Int. Cl.
| | | |
|---|---|---|
| *C12N 15/52* | (2006.01) | |
| *C12P 3/00* | (2006.01) | |
| *A01N 59/16* | (2006.01) | |
| *A61K 8/27* | (2006.01) | |
| *A61K 9/00* | (2006.01) | |
| *A61K 33/30* | (2006.01) | |
| *A61Q 19/00* | (2006.01) | |
| *C07K 14/395* | (2006.01) | |
| *C12N 1/18* | (2006.01) | |
| *C12N 9/04* | (2006.01) | |
| *C12N 9/16* | (2006.01) | |
| *C12N 9/20* | (2006.01) | |

(52) U.S. Cl.
CPC ............ *C12P 3/00* (2013.01); *A01N 59/16* (2013.01); *A61K 8/27* (2013.01); *A61K 9/0029* (2013.01); *A61K 9/0053* (2013.01); *A61K 33/30* (2013.01); *A61Q 19/00* (2013.01); *C07K 14/395* (2013.01); *C12N 1/18* (2013.01); *C12N 9/0006* (2013.01); *C12N 9/16* (2013.01); *C12N 9/20* (2013.01); *C12N 15/52* (2013.01); *C12Y 101/01001* (2013.01); *C12Y 301/03001* (2013.01)

(58) Field of Classification Search
CPC .... C12Y 301/03001; C12Y 101/01001; C12N 9/20; C12N 9/14; C12N 15/52
See application file for complete search history.

(56) References Cited

U.S. PATENT DOCUMENTS

2007/0178499 A1 * 8/2007 Barbas, III ........... C12Q 1/6837
435/6.12
2020/0123527 A1 * 4/2020 Shakeel ............... C07K 14/005

FOREIGN PATENT DOCUMENTS

| EP | 0168933 A2 | 6/1985 |
|---|---|---|
| WO | 1996009074 A1 | 3/1996 |

OTHER PUBLICATIONS

Jayaseelan et al., Novel microbial route to synthesize ZnO nanoparticles using Aeromonas hydrophila and their activity against pathogenic bacteria and fungi, Spectrochimica Acta Part A 90, p. 78-84, 2012.
International Search Report and Written Opinion issued for PCT/US2018/050573, dated Nov. 30, 2018.

* cited by examiner

*Primary Examiner* — Tekchand Saidha
(74) *Attorney, Agent, or Firm* — Thomas|Horstemeyer, LLP

(57) ABSTRACT

Described herein are biological devices and methods for using the same to produce oxidized zinc. The biological devices include microbial cells transformed with a DNA construct containing genes for producing a zinc-related protein, an alkaline phosphatase, and an alcohol dehydrogenase. In some instances, the biological devices also include a gene for lipase. The oxidized zinc compositions produced herein have numerous applications.

20 Claims, 26 Drawing Sheets
Specification includes a Sequence Listing.

Control: Bacterial Culture (*Bacillus subtilis*) growth before UV exposure.

Figure A: 24 hour bacterial culture growth (replicate 1);
Figure B: 24 hour bacterial culture growth (replicate 2)

SEQUENCE LISTING

<160> NUMBER OF SEQ ID NOS: 7

<210> SEQ ID NO 1
<211> LENGTH: 1493
<212> TYPE: DNA
<213> ORGANISM: Streptomyces zinciresistens

<400> SEQUENCE: 1

```
cctaggatga cagatcgttg tccaggtagg gatgctccac acttagcagt cattggagca      60
ggtccagctg gcttagcagc agcattagct gctgctgcta gaggtgttcg tgtaaccttg     120
ttggatgctg aaccagaagc aggaggccaa ttctatagac agccagcagc agctttacgt     180
gctagaaggc cacaagcatt acaccatcag tggcgtacct ttgccagatt gagacacgga     240
ttagccaggc acattgcagc aggtagagtt agacatgcta gagaacacca tgtttggttt     300
gctgagagag ctcctgatgg tggattcacc gttcatgctt tgactggtcc aggtagagga     360
gatccagcag aagtgagagc agatgcagtc ttgttggcaa ctggtggtca cgagactgtg     420
ttgccattcc caggttggac cttgccaggt gttgtcacag ctggaggtgc ccaagccatg     480
ttgaaggcag gtttagttac atctggcaac accgcagtcg tagctggtac tggtccattg     540
ttgttgccag tagctacagg tttagctgct gctggtgttg acgtaagagc attagtcgaa     600
agtgctgatc ctggtgcctt accaagacag gcacgtgctt tggcagctca acctggcaag     660
ttggctgaag gtgctttgta tgctggtcaa ttgttgaggc acagagtgcg tgtcttgact     720
agacacactg tcgttgaagc acatggtaca gagaggttgg aagcagttac tgttgcagcc     780
ttggatgcag gtggacgtac tagacctggc actgctagaa gaatagcatg tgcaacttta     840
gctgtgggtc atggtatgtt gccacataca gacttggcag acgccttagg ctgccgttta     900
gcaggtccag cagttcatgc agatgatgaa caaagaactg atgttcctgg tgtgtgggca     960
gcaggagagt gtactggcgt aggtggtgca gctttgtctt tggctgaggg tcatatcgct    1020
ggcagaagtg cagcagccag attgttagga gcacctccag gtcccgacgc atggccagag    1080
gcagctagaa caagagcaag gttgagagct ttctccgctg tattggatgc tgtttacact    1140
cctcctcctg gttggggtga gagagtcacc gacgcaaccg ttgtatgcag gtgtgaagaa    1200
gttacagcag gtgcaatccg tgcttctgtg agggaattgg gagctggtga cgtacgtact    1260
gtaaagttgt tgactagagc tggcatggga tggtgtcagg gaagaatgtg tgctcctgct    1320
gtcgctggat tggcaggttg tgctttcact cctagtcgta gaccattcgc taggccagtg    1380
```

```
cctttgggag tgttggccag agctggtgaa gatgcaggtg gcgatggagg cagagctgag   1440
gatcaaggtg aaggagatgg acgtgctgct ggagcaggag gttgattaat taa          1493

<210> SEQ ID NO 2
<211> LENGTH: 1124
<212> TYPE: DNA
<213> ORGANISM: Haliscomenobacter hydrossis

<400> SEQUENCE: 2
ggcgcgccac catgaagaag ttgttgattt gtgccttggc tatgttgttg tgtttacctg     60
tattctccca gaagaaggct aaaggtgcag caagtcctgc tgtcgctgtt cctaaggcta    120
agaatgtaat cttgttaatc ggtgatggta tgggtttaac acacatttca gctggaatgt    180
actttaacaa taaccaatcc aactttgaaa gatttccagt tgcaggtttg cagaaagcat    240
attctgctag tgatttgatt accgatagtg ctgctggtgc taccgctttc gcttctggca    300
ttaagactta caacggtgca ataggtgtga atactgattc tatgcctgtt aagaccatct    360
tggaagaggc agaagaaaga ggcttagcaa ctggaatggt cgttacaagt acattaactc    420
atgctactcc agcttcattt gttgctcatg ttaggaatag gaaattcgat gaggaaattg    480
caaccttctt cttaaagact gaaatcgact tcttggcagg tggtgaaaag aagttctttg    540
aacagagagc agccgacggc agaaacttgt accaagagtt aaaggataaa ggttatcagg    600
tatctgattt cactcagaag aatgcatctt ctttggcacc tgatccatct aagaacttta    660
tctatttcag tgcagacgca gatcctgcta agcctccga aggaagatcc tatttggctc    720
ctttatctgt gttagcagct aatcatttga agaagcgtag tgagaaaggt tcttccttga    780
tggttgaatc ttcacaaatt gattggggag acataacaa tgaaagtgac tacatagtct    840
cagaagttgt cgatttcgac caaaccattg gaaagatatt ggatttcgca gctgctgatg    900
gagaaacctt ggtcattgtt actgccgacc atgaaaccgg tggatatgca atttctccag    960
gctccgaatt aggcaagatc cgtggtgctt tcacaactaa aggtcatact gcacaattga   1020
tccctgtatt cgctttcggt ccaggtgctg aattgtttgc tggtgtttat gagaacactg   1080
ctatctacgt caagatgagg caagtcttag gattctaagg tacc                   1124

<210> SEQ ID NO 3
<211> LENGTH: 1059
<212> TYPE: DNA
<213> ORGANISM: Saccharomyces cerevisiae

<400> SEQUENCE: 3
ggtaccatgt ctattccaga aactcaaaaa gccattatct tctacgaatc caacggcaag     60
ttggagcata aggatatccc agttccaaag ccaaagccca acgaattgtt aatcaacgtc    120
aagtactctg gtgtctgcca caccgatttg cacgcttggc atggtgactg gccattgcca    180
actaagttac cattagttgg tggtcacgaa ggtgccggtg tcgttgtcgg catgggtgaa    240
aacgttaagg ctggaagat cggtgactac gccggtatca atggttgaa cggttcttgt     300 atggcctgtg aatactgtga attgggtaac gaatccaact gtcctcacgc tgacttgtca    360
ggttacaccc acgacggttc tttccaagaa tacgctaccg ctgacgctgt tcaagccgct    420
cacattcctc aaggtactga cttggctgaa gtcgcgccaa tcttgtgtgc tggtatcacc    480
gtatacaagg ctttgaagtc tgccaacttg agagcaggcc actgggcggc catttctggt    540
gctgctggtg gtctaggttc tttggctgtt caatatgcta aggcgatggg ttacagagtc    600
ttaggtattg atggtggtcc aggaaaggaa gaattgttta cctcgctcgg tggtgaagta    660
```

```
ttcatcgact tcaccaaaga gaaggacatt gttagcgcag tcgttaaggc taccaacggc      720
ggtgcccacg gtatcatcaa tgtttccgtt tccgaagccg ctatcgaagc ttctaccaga      780
tactgtaggg cgaacggtac tgttgtcttg gttggtttgc cagccggtgc aaagtgctcc      840
tctgatgtct tcaaccacgt tgtcaagtct atctccattg tcggctctta cgtggggaac      900
agagctgata ccagagaagc cttagatttc tttgccagag gtctagtcaa gtctccaata      960
aaggtagttg gcttatccag tttaccagaa atttacgaaa agatggagaa gggccaaatt     1020
gctggtagat acgttgttga cacttctaaa taactcgag                            1059

<210> SEQ ID NO 4
<211> LENGTH: 890
<212> TYPE: DNA
<213> ORGANISM: Artificial sequence
<220> FEATURE:
<223> OTHER INFORMATION: Synthetic construct

<400> SEQUENCE: 4
ggattcaaag aggagaaata ctagatggtg agcaagggcg aggagctgtt caccggggtg       60
gtgcccatcc tggtcgagct ggacggcgac gtaaacggcc acaagttcag cgtgtccggc      120
gagggcgagg gcgatgccac ctacggcaag ctgaccctga agttcatctg caccaccggc      180
aagctgcccg tgccctggcc caccctcgtg accaccttcg gctacggcct gcaatgcttc      240
gcccgctacc ccgaccacat gaagctgcac gacttcttca gtccgccat gcccgaaggc       300 tacgtccagg agcgcaccat cttcttcaag gacgacggca actacaagac ccgcgccgag      360
gtgaagttcg agggcgacac cctggtgaac cgcatcgagc tgaagggcat cgacttcaag      420
gaggacggca acatcctggg gcacaagctg gagtacaact acaacagcca caacgtctat      480
atcatggccg acaagcagaa gaacggcatc aaggtgaact tcaagatccg ccacaacatc      540
gaggacggca gcgtgcagct cgccgaccac taccagcaga cacccccat cggcgacggc       600 cccgtgctgc tgcccgacaa ccactacctg agctaccagt ccgccctgag caaagacccc      660
aacgagaagc gcgatcacat ggtcctgctg gagttcgtga ccgccgccgg gatcactctc      720
ggcatggacg agctgtacaa gtaataatac tagagccagg catcaaataa acgaaaggc      780 tcagtcgaaa gactgggcct ttcgttttat ctgttgtttg tcggtgaacg ctctctacta      840
gagtcacact ggctcacctt cgggtgggcc tttctgcgtt tataaagctt                 890

<210> SEQ ID NO 5
<211> LENGTH: 12243
<212> TYPE: DNA
<213> ORGANISM: Artificial sequence
<220> FEATURE:
<223> OTHER INFORMATION: Synthetic construct

<400> SEQUENCE: 5
acggattaga agccgccgag cgggtgacag ccctccgaag gaagactctc ctccgtgcgt       60
cctcgtcttc accggtcgcg ttcctgaaac gcagatgtgc ctcgcgccgc actgctccga      120
acaataaaga ttctacaata ctagcttta tggttatgaa gaggaaaaat tggcagtaac       180
ctggccccac aaaccttcaa atgaacgaat caaattaaca accataggat gataatgcga      240
ttagtttttt agccttattt ctgggtaat taatcagcga agcgatgatt tttgatctat       300
taacagatat ataaatgcaa aaactgcata accactttaa ctaatacttt caacattttc      360
ggtttgtatt acttcttatt caaatgtaat aaaagtatca acaaaaaatt gttaatatac      420
```

```
ctctatactt taacgtcaag gagaaaaaac cccggatcgg actactagca gctgtaatac    480
gactcactat agggaatatt aagcttccta ggatgacaga tcgttgtcca ggtagggatg    540
ctccacactt agcagtcatt ggagcaggtc cagctggctt agcagcagca ttagctgctg    600
ctgctagagg tgttcgtgta accttgttgg atgctgaacc agaagcagga ggccaattct    660
atagacagcc agcagcagct ttacgtgcta gaaggccaca agcattacac catcagtggc    720
gtacctttgc cagattgaga cacggattag ccaggcacat tgcagcaggt agagttagac    780
atgctagaga acaccatgtt tggtttgctg agagagctcc tgatggtgga ttcaccgttc    840
atgctttgac tggtccaggt agaggagatc cagcagaagt gagagcagat gcagtcttgt    900
tggcaactgg tggtcacgag actgtgttgc cattcccagg ttggaccttg ccaggtgttg    960
tcacagctgg aggtgcccaa gccatgttga aggcaggttt agttacatct ggcaacaccg   1020
cagtcgtagc tggtactggt ccattgttgt tgccagtagc tacaggttta gctgctgctg   1080
gtgttgacgt aagagcatta gtcgaaagtg ctgatcctgg tgccttacca agacaggcac   1140
gtgctttggc agctcaacct ggcaagttgg ctgaaggtgc tttgtatgct ggtcaattgt   1200
tgaggcacag agtgcgtgtc ttgactagac acactgtcgt tgaagcacat ggtacagaga   1260
ggttggaagc agttactgtt gcagccttgg atgcaggtgg acgtactaga cctggcactg   1320
ctagaagaat agcatgtgca actttagctg tgggtcatgg tatgttgcca catacagact   1380
tggcagacgc cttaggctgc cgtttagcag gtccagcagt tcatgcagat gatgaacaaa   1440
gaactgatgt tcctggtgtg tgggcagcag gagagtgtac tggcgtaggt ggtgcagctt   1500
tgtctttggc tgagggtcat atcgctggca gaagtgcagc agccagattg ttaggagcac   1560
ctccaggtcc cgacgcatgg ccagaggcag ctagaacaag agcaaggttg agagctttct   1620
ccgctgtatt ggatgctgtt tacactcctc ctcctggttg gggtgagaga gtcaccgacg   1680
caaccgttgt atgcaggtgt gaagaagtta cagcaggtgc aatccgtgct tctgtgaggg   1740
aattgggagc tggtgacgta cgtactgtaa agttgttgac tagagctggc atgggatggt   1800
gtcagggaag aatgtgtgct cctgctgtcg ctggattggc aggttgtgct ttcactccta   1860
gtcgtagacc attcgctagg ccagtgcctt gggagtgtt ggccagagct ggtgaagatg   1920
caggtggcga tggaggcaga gctgaggatc aaggtgaagg agatggacgt gctgctggag   1980
caggaggttg attaattaat catgtaatta gttatgtcac gcttacattc acgccctccc   2040
cccacatccg ctctaaccga aaaggaagga gttagacaac ctgaagtcta ggtccctatt   2100
tatttttta tagttatgtt agtattaaga acgttattta tatttcaaat ttttcttttt   2160
tttctgtaca gacgcgtgta cgcatgtaac attatactga aaaccttgct tgagaaggtt   2220
ttgggacgct cgaaggcttt aatttgccgg attagaagcc gccgagcggg tgacagccct   2280
ccgaaggaag actctcctcc gtgcgtcctc gtcttcaccg gtcgcgttcc tgaaacgcag   2340
atgtgcctcg cgccgcactg ctccgaacaa taaagattct acaatactag cttttatggt   2400
tatgaagagg aaaaattggc agtaacctgg ccccacaaac cttcaaatga acgaatcaaa   2460
ttaacaacca taggatgata atgcgattag ttttttagcc ttatttctgg ggtaattaat   2520
cagcgaagcg atgattttg atctattaac agatatataa atgcaaaaac tgcataacca   2580
ctttaactaa tactttcaac attttcggtt tgtattactt cttattcaaa tgtaataaaa   2640
gtatcaacaa aaaattgtta atatacctct atactttaac gtcaaggagg gcgcgccacc   2700
atgaagaagt tgttgatttg tgccttggct atgttgttgt gtttacctgt attctcccag   2760
aagaaggcta aaggtgcagc aagtcctgct gtcgctgttc ctaaggctaa gaatgtaatc   2820
```

```
ttgttaatcg gtgatggtat gggtttaaca cacatttcag ctggaatgta ctttaacaat    2880
aaccaatcca actttgaaag atttccagtt gcaggtttgc agaaagcata ttctgctagt    2940
gatttgatta ccgatagtgc tgctggtgct accgctttcg cttctggcat taagacttac    3000
aacggtgcaa taggtgtgaa tactgattct atgcctgtta agaccatctt ggaagaggca    3060
gaagaaagag gcttagcaac tggaatggtc gttacaagta cattaactca tgctactcca    3120
gcttcatttg ttgctcatgt taggaatagg aaattcgatg aggaaattgc aaccttcttc    3180
ttaaagactg aaatcgactt cttggcaggt ggtggaaaga agttctttga cagagagca    3240 gccgacggca gaaacttgta ccaagagtta aaggataaag gttatcaggt atctgatttc    3300
actcagaaga atgcatcttc tttggcacct gatccatcta agaactttat ctatttcagt    3360
gcagacgcag atcctgctaa agcctccgaa ggaagatcct atttggctcc tttatctgtg    3420
ttagcagcta atcatttgaa gaagcgtagt gagaaaggtt tcttcttgat ggttgaatct    3480
tcacaaattg attggggagg acataacaat gaaagtgact acatagtctc agaagttgtc    3540
gatttcgacc aaaccattgg aaagatattg gatttcgcag ctgctgatgg agaaaccttg    3600
gtcattgtta ctgccgacca tgaaaccggt ggatatgcaa tttctccagg ctccgaatta    3660
ggcaagatcc gtggtgcttt cacaactaaa ggtcatactg cacaattgat ccctgtattc    3720
gctttcggtc caggtgctga attgtttgct ggtgtttatg agaacactgc tatctacgtc    3780
aagatgaggc aagtcttagg attctaaggt acctcatgta attagttatg tcacgcttac    3840
attcacgccc tccccccaca tccgctctaa ccgaaaagga aggagttaga caacctgaag    3900
tctaggtccc tatttatttt tttatagtta tgttagtatt aagaacgtta tttatatttc    3960 aaattttct tttttttctg tacagacgcg tgtacgcatg taacattata ctgaaaacct    4020
tgcttgagaa ggttttggga cgctcgaagg ctttaatttg ccggattaga agccgccgag    4080
cgggtgacag ccctccgaag gaagactctc ctccgtgcgt cctcgtcttc accggtcgcg    4140
ttcctgaaac gcagatgtgc ctcgcgccgc actgctccga acaataaaga ttctacaata    4200
ctagctttta tggttatgaa gaggaaaaat tggcagtaac ctggccccac aaaccttcaa    4260
atgaacgaat caaattaaca accataggat gataatgcga ttagtttttt agccttattt    4320
ctggggtaat taatcagcga agcgatgatt tttgatctat taacagatat ataaatgcaa    4380
aaactgcata accactttaa ctaatacttt caacattttc ggtttgtatt acttcttatt    4440
caaatgtaat aaaagtatca acaaaaaatt gttaatatac ctctatactt taacgtcaag    4500
gagggatcca tgtctattcc agaaactcaa aaagccatta tcttctacga atccaacggc    4560
aagttggagc ataaggatat cccagttcca aagccaaagc caacgaatt gttaatcaac    4620 gtcaagtact ctggtgtctg ccacaccgat ttgcacgctt ggcatggtga ctggccattg    4680
ccaactaagt taccattagt tggtggtcac gaaggtgccg gtgtcgttgt cggcatgggt    4740
gaaaacgtta agggctggaa gatcggtgac tacgccggta tcaaatggtt gaacggttct    4800
tgtatggcct gtgaatactg tgaattgggt aacgaatcca actgtcctca cgctgacttg    4860
tctggttaca cccacgacgg ttcttttcca agaatacgcta ccgctgacgc tgttcaagcc    4920
gctcacattc ctcaaggtac tgacttggct gaagtcgcgc aatcttgtg tgctggtatc    4980 accgtataca aggctttgaa gtctgccaac ttgagagcag gccactgggc ggccatttct    5040
ggtgctgctg gtggtctagg ttcctttggct gttcaatatg ctaaggcgat gggttacaga    5100
gtcttaggta ttgatggtgg tccaggaaag gaagaattgt ttacctcgct cggtggtgaa    5160
```

-continued

```
gtattcatcg acttcaccaa agagaaggac attgttagcg cagtcgttaa ggctaccaac   5220
ggcggtgccc acggtatcat caatgttttcc gtttccgaag ccgctatcga agcttctacc  5280
agatactgta gggcgaacgg tactgttgtc ttggttggtt tgccagccgg tgcaaagtgc   5340
tcctctgatg tcttcaacca cgttgtcaag tctatctcca ttgtcggctc ttacgtgggg   5400
aacagagctg ataccagaga agccttagat ttctttgcca gaggtctagt caagtctcca   5460
ataaaggtag ttggcttatc cagtttacca gaaatttacg aaaagatgga aagggccaa    5520
attgctggta gatacgttgt tgacacttct aaataagaat tctcatgtaa ttagttatgt   5580
cacgcttaca ttcacgccct cccccacat ccgctctaac cgaaaaggaa ggagttagac    5640
aacctgaagt ctaggtccct atttattttt ttatagttat gttagtatta agaacgttat   5700
ttatatttca aattttttctt tttttctgt acagacgcgt gtacgcatgt aacattatac   5760
tgaaaacctt gcttgagaag gttttgggac gctcgaaggc tttaatttgc cggattagaa   5820
gccgccgagc gggtgacagc cctccgaagg aagactctcc tccgtgcgtc ctcgtcttca   5880
ccggtcgcgt tcctgaaacg cagatgtgcc tcgcccgca ctgctccgaa caataaagat    5940
tctacaatac tagcttttat ggttatgaag aggaaaaatt ggcagtaacc tggccccaca   6000
aaccttcaaa tgaacgaatc aaattaacaa ccataggatg ataatgcgat tagtttttta   6060
gccttatttc tggggtaatt aatcagcgaa gcgatgattt tgatctatt aacagatata    6120
taaatgcaaa aactgcataa ccactttaac taatactttc aacattttcg gtttgtatta   6180
cttcttattc aaatgtaata aaagtatcaa caaaaaattg ttaatatacc tctatacttt   6240
aacgtcaagg aggcggccgc catggtgagc aagggcgagg agctgttcac cggggtggtg   6300
cccatcctgg tcgagctgga cggcgacgta aacggccaca agttcagcgt gtccggcgag   6360
ggcgagggcg atgccaccta cggcaagctg accctgaagt tcatctgcac caccggcaag   6420
ctgcccgtgc cctggcccac cctcgtgacc accttcggct acggcctgca atgcttcgcc   6480
cgctaccccg accacatgaa gctgcacgac ttcttcaagt ccgccatgcc cgaaggctac   6540
gtccaggagc gcaccatctt cttcaaggac gacggcaact acaagacccg cgccgaggtg   6600
aagttcgagg gcgacaccct ggtgaaccgc atcgagctga agggcatcga cttcaaggag   6660
gacggcaaca tcctggggca caagctggag tacaactaca acagccacaa cgtctatatc   6720
atggccgaca agcagaagaa cggcatcaag gtgaacttca agatccgcca caacatcgag   6780
gacggcagcg tgcagctcgc cgaccactac cagcagaaca cccccatcgg cgacggcccc   6840
gtgctgctgc ccgacaacca ctacctgagc taccagtccg ccctgagcaa agaccccaac   6900
gagaagcgcg atcacatggt cctgctggag ttcgtgaccg ccgccgggat cactctcggc   6960
atggacgagc tgtacaagta atctagaggg ccgcatcatg taattagtta tgtcacgctt   7020
acattcacgc cctcccccca catccgctct aaccgaaaag gaaggagtta gacaacctga   7080
agtctaggtc cctatttatt tttttatagt tatgttagta ttaagaacgt tatttatatt   7140
tcaaattttt ctttttttttc tgtacagacg cgtgtacgca tgtaacatta tactgaaaac  7200
cttgcttgag aaggttttgg gacgctcgaa ggctttaatt tgcggccctg cattaatgaa   7260
tcggccaacg cgcggggaga ggcggtttgc gtattgggcg ctcttccgct tcctcgctca   7320
ctgactcgct gcgctcggtc gttcggctgc ggcgagcggt atcagctcac tcaaaggcgg   7380
taatacggtt atccacagaa tcaggggata acgcaggaaa gaacatgtga gcaaaaggcc   7440
agcaaaagcc caggaaccgt aaaaaggccg cgttgctggc gtttttccat aggctccgcc   7500
ccctgacga gcatcacaaa aatcgacgct caagtcagag gtggcgaaac ccgacaggac   7560
```

```
tataaagata ccaggcgttt cccctggaa gctccctcgt gcgctctcct gttccgaccc    7620
tgccgcttac cggatacctg tccgcctttc tccttcggg aagcgtggcg ctttctcata    7680
gctcacgctg taggtatctc agttcggtgt aggtcgttcg ctccaagctg gctgtgtgc    7740 acgaaccccc cgttcagccc gaccgctgcg ccttatccgg taactatcgt cttgagtcca    7800
acccggtaag acacgactta tcgccactgg cagcagccac tggtaacagg attagcagag    7860
cgaggtatgt aggcggtgct acagagttct tgaagtggtg gcctaactac ggctacacta    7920
gaaggacagt atttggtatc tgcgctctgc tgaagccagt taccttcgga aaaagagttg    7980
gtagctcttg atccgcaaa caaaccaccg ctggtagcgg tggttttttt gtttgcaagc    8040
agcagattac gcgcagaaaa aaggatctca agaagatcc tttgatcttt tctacggggt    8100
ctgacgctca gtggaacgaa aactcacgtt aagggatttt ggtcatgaga ttatcaaaaa    8160
ggatcttcac ctagatcctt ttaaattaaa aatgaagttt taaatcaatc taaagtatat    8220
atgagtaaac ttggtctgac agttaccaat gcttaatcag tgaggcacct atctcagcga    8280
tctgtctatt tcgttcatcc atagttgcct gactccccgt cgtgtagata actacgatac    8340
gggagcgctt accatctggc cccagtgctg caatgatacc gcgagaccca cgctcaccgg    8400
ctccagattt atcagcaata aaccagccag ccggaagggc cgagcgcaga gtggtcctg    8460 caactttatc cgcctccatc cagtctatta attgttgccg ggaagctaga gtaagtagtt    8520
cgccagttaa tagtttgcgc aacgttgttg gcattgctac aggcatcgtg gtgtcactct    8580
cgtcgtttgg tatggcttca ttcagctccg gttcccaacg atcaaggcga gttacatgat    8640 ccccatgtt gtgcaaaaaa gcggttagct ccttcggtcc tccgatcgtt gtcagaagta    8700
agttggccgc agtgttatca ctcatggtta tggcagcact gcataattct cttactgtca    8760
tgccatccgt aagatgcttt tctgtgactg gtgagtactc aaccaagtca ttctgagaat    8820
agtgtatgcg gcgaccgagt tgctcttgcc cggcgtcaat acgggataat agtgtatcac    8880
atagcagaac tttaaaagtg ctcatcattg gaaaacgttc ttcggggcga aaactctcaa    8940
ggatcttacc gctgttgaga tccagttcga tgtaacccac tcgtgcaccc aactgatctt    9000
cagcatcttt tactttcacc agcgtttctg ggtgagcaaa aacaggaagg caaaatgccg    9060
caaaaaaggg aataagggcg acacggaaat gttgaatact catactcttc ctttttcaat    9120
gggtaataac tgatataatt aaattgaagc tctaatttgt gagtttagta tacatgcatt    9180
tacttataat acagttttt agttttgctg gccgcatctt ctcaaatatg cttcccagcc    9240
tgcttttctg taacgttcac cctctacctt agcatccctt cccttttgcaa atagtcctct    9300 tccaacaata ataatgtcag atcctgtaga gaccacatca tccacggttc tatactgttg    9360
acccaatgcg tctcccttgt catctaaacc cacaccgggt gtcataatca accaatcgta    9420
accttcatct cttccacccca tgtctctttg agcaataaag ccgataacaa atctttgtc    9480 gctcttcgca atgtcaacag tacccttagt atattctcca gtagataggg agcccttgca    9540
tgacaattct gctaacatca aaaggcctct aggttccttt gttacttctt ctgccgcctg    9600
cttcaaaccg ctaacaatac ctgggcccac cacaccgtgt gcattcgtaa tgtctgccca    9660
ttctgctatt ctgtatacac ccgcagagta ctgcaatttg actgtattac caatgtcagc    9720
aaattttctg tcttcgaaga gtaaaaaatt gtacttggcg ataatgcct ttagcggctt    9780 aactgtgccc tccatggaaa aatcagtcaa gatatccaca tgtgttttta gtaaacaaat    9840
tttgggacct aatgcttcaa ctaactccag taattccttg gtggtacgaa catccaatga    9900
```

```
agcacacaag tttgtttgct tttcgtgcat gatattaaat agcttggcag caacaggact    9960
aggatgagta gcagcacgtt ccttatatgt agctttcgac atgatttatc ttcgtttcct   10020
gcaggttttt gttctgtgca gttgggttaa gaatactggg caatttcatg tttcttcaac   10080
actacatatg cgtatatata ccaatctaag tctgtgctcc ttccttcgtt cttccttctg   10140
ttcggagatt accgaatcaa aaaaatttca agaaaccga aatcaaaaaa agaataaaa     10200
aaaaaatgat gaattgaatt gaaaagctag cttatcgatg ataagctgtc aaagatgaga   10260
attaattcca cggactatag actatactag atactccgtc tactgtacga tacacttccg   10320
ctcaggtcct tgtcctttaa cgaggcctta ccactctttt gttactctat tgatccagct   10380
cagcaaaggc agtgtgatct aagattctat cttcgcgatg tagtaaaact agctagaccg   10440
agaaagagac tagaaatgca aaaggcactt ctacaatggc tgccatcatt attatccgat   10500
gtgacgctgc agcttctcaa tgatattcga atacgctttg aggagataca gcctaatatc   10560
cgacaaactg ttttacagat ttacgatcgt acttgttacc catcattgaa tttttgaacat  10620
ccgaacctgg gagttttccc tgaaacagat agtatatttg aacctgtata ataatatata   10680
gtctagcgct ttacggaaga caatgtatgt atttcggttc ctggagaaac tattgcatct   10740
attgcatagg taatcttgca cgtcgcatcc ccggttcatt ttctgcgttt ccatcttgca   10800
cttcaatagc atatctttgt taacgaagca tctgtgcttc attttgtaga acaaaaatgc   10860
aacgcgagag cgctaatttt tcaaacaaag aatctgagct gcattttac agaacagaaa   10920
tgcaacgcga agcgctatt ttaccaacga agaatctgtg cttcattttt gtaaaacaaa   10980
aatgcaacgc gacgagagcg ctaattttc aaacaaagaa tctgagctgc attttacag   11040
aacagaaatg caacgcgaga gcgctatttt accaacaaag aatctatact tctttttgt   11100
tctacaaaaa tgcatcccga gagcgctatt tttctaacaa agcatcttag attacttttt   11160
ttctcctttg tgcgctctat aatgcagtct cttgataact ttttgcactg taggtccgtt   11220
aaggttagaa gaaggctact ttggtgtcta ttttctcttc cataaaaaaa gcctgactcc   11280
acttcccgcg tttactgatt actagcgaag ctgcgggtgc attttttcaa gataaaggca   11340
tccccgatta tattctatac cgatgtggat tgcgcatact tgtgaacag aaagtgatag   11400
cgttgatgat tcttcattgg tcagaaaatt atgaacggtt tcttctattt tgtctctata   11460
tactacgtat aggaaatgtt tacattttcg tattgttttc gattcactct atgaatagtt   11520
cttactacaa ttttttttgtc taaagagtaa tactagagat aaacataaaa aatgtagagg   11580
tcgagtttag atgcaagttc aaggagcgaa aggtggatgg gtaggttata tagggatata   11640
gcacagagat atatagcaaa gagatacttt tgagcaatgt ttgtggaagc ggtattcgca   11700
atgggaagct ccaccccggt tgataatcag aaaagcccca aaaacaggaa gattgtataa   11760
gcaaatattt aaattgtaaa cgttaatatt ttgttaaaat tcgcgttaaa ttttttgttaa   11820
atcagctcat tttttaacga atagcccgaa atcggcaaaa tcccttataa atcaaaagaa   11880
tagaccgaga tagggttgag tgttgttcca gtttccaaca agagtccact attaaagaac   11940
gtggactcca acgtcaaagg gcgaaaaagg gtctatcagg gcgatggccc actacgtgaa   12000
ccatcacccct aatcaagttt ttggggtcg aggtgccgta aagcagtaaa tcggaagggt  12060
aaacggatgc ccccatttag agcttgacgg ggaaagccgg cgaacgtggc gagaaaggaa   12120
gggaagaaag cgaaaggagc gggggctagg gcggtgggaa gtgtaggggt cacgctgggc   12180
gtaaccacca caccgccgc gcttaatggg gcgctacagg gcgcgtgggg atgatccact   12240
agt                                                                 12243
```

<210> SEQ ID NO 6
<211> LENGTH: 1215
<212> TYPE: DNA
<213> ORGANISM: Micrococcus sp. HL-2003

<400> SEQUENCE: 6

```
atggtgttta tcgtcaatct tttctcctgc accttatctg aaaccacggt tagctcaata      60
aaatctgaag ctacggttag ctcaacattt actgccgtca cggccctgca attggtggct     120
gagggtaagt tgcagtcggc gaagggtttc ggtggtggta cgattcacta cccaaccctc     180
gcggccgaag caccctggtg gacgccgggc caaggccatg ttacgaggc gatcacctac      240
ggctggctgg tcggcgaact gctgcgccgc gccgatgggc gtgggcctgg tctgttaggc     300
gctattgccg tggttcctgg ttacgtttct tacgagaact ctatcaagtg gtggggaccg     360
cgtctggctt cttggggctt tgtcgttgca cggccgttgg gcctggactt tcatgtgggc     420
ctggcggatg aagagtttta tcgtgttgcc catatagcgc gcagcaaagc caatgcagca     480
ctagataaca ttgctgatga caccgtcggc agtatagatc taagcggtt gggcgctatt      540
ggctggtcag gtggcggcgg cgcgcttaaa ctggcaacgg agcgcagcac agtacgagcc     600
attttgacca gtactaataa acctgaatgg cgacgcttcg ataaattctt atgtgcctgc     660
gaggatgacc ggattgctga gactaagaaa tatgccaacg cgttttataa aaatgccgac     720
atgctcgaag agttgacccg tgaacacagt atcgggccgg ataaaacatt attgacacaa     780
actcggtttg gcttggggtg cttggatcaa ccgcaagcag gggttaaaat tcatttgaa      840
gagtaccttg atcaaaccca tggatttatc aatttgacgc cagtttcaca taaggcgaga     900
gcaaatctga ttcagatgcc taatgccaca ttcggccttg gccgcgtgc ttttgggcat      960
cctggtgcag gtggatcggt aggttttgcc gaccccgaac acgatgtagc gtttggtttc    1020
gtgactaata cattgggcc ttatgtagtt gagtttaaaa gccgtcatcc ctcatttat      1080
gcatataaag atggattggt gctgactgga aatgacgtcg actatgtgac tgattactat    1140
gcaacaaagc atgctgtaca tttagatgat ccacgtgcac agaagttggt cggaatattg    1200
gccggttgtc tgtaa                                                     1215
```

<210> SEQ ID NO 7
<211> LENGTH: 14168
<212> TYPE: DNA
<213> ORGANISM: Artificial sequence
<220> FEATURE:
<223> OTHER INFORMATION: Synthetic construct

<400> SEQUENCE: 7

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa aggaaaaat tggcagtaac      180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaaatac    480
gactcactat agggaatatt aagcttccta ggatgacaga tcgttgtcca ggtagggatg     540
```

-continued

```
ctccacactt agcagtcatt ggagcaggtc cagctggctt agcagcagca ttagctgctg    600
ctgctagagg tgttcgtgta accttgttgg atgctgaacc agaagcagga ggccaattct    660
atagacagcc agcagcagct ttacgtgcta gaaggccaca agcattacac catcagtggc    720
gtacctttgc cagattgaga cacgattag ccaggcacat tgcagcaggt agagttagac     780
atgctagaga acaccatgtt tggtttgctg agagagctcc tgatggtgga ttcaccgttc    840
atgctttgac tggtccaggt agaggagatc cagcagaagt gagagcagat gcagtcttgt    900
tggcaactgg tggtcacgag actgtgttgc cattcccagg ttggaccttg ccaggtgttg    960
tcacagctgg aggtgcccaa gccatgttga aggcaggttt agttacatct ggcaacaccg   1020
cagtcgtagc tggtactggt ccattgttgt tgccagtagc tacaggttta gctgctgctg   1080
gtgttgacgt aagagcatta gtcgaaagtg ctgatcctgg tgccttacca agacaggcac   1140
gtgctttggc agctcaacct ggcaagttgg ctgaaggtgc tttgtatgct ggtcaattgt   1200
tgaggcacag agtgcgtgtc ttgactagac acactgtcgt tgaagcacat ggtacagaga   1260
ggttggaagc agttactgtt gcagccttgg atgcaggtga acgtactaga cctggcactg   1320
ctagaagaat agcatgtgca actttagctg tgggtcatgg tatgttgcca catacagact   1380
tggcagacgc cttaggctgc cgtttagcag gtccagcagt tcatgcagat gatgaacaaa   1440
gaactgatgt tcctggtgtg tgggcagcag gagagtgtac tggcgtaggt ggtgcagctt   1500
tgtctttggc tgagggtcat atcgctggca gaagtgcagc agccagattg ttaggagcac   1560
ctccaggtcc cgacgcatgg ccagaggcag ctagaacaag agcaaggttg agagctttct   1620
ccgctgtatt ggatgctgtt tacactcctc ctcctggttg gggtgagaga gtcaccgacg   1680
caaccgttgt atgcaggtgt gaagaagtta cagcaggtgc aatccgtgct tctgtgaggg   1740
aattgggagc tggtgacgta cgtactgtaa agttgttgac tagagctggc atgggatggt   1800
gtcagggaag aatgtgtgct cctgctgtcg ctggattggc aggttgtgct ttcactccta   1860
gtcgtagacc attcgctagg ccagtgcctt tgggagtgtt ggccagagct ggtgaagatg   1920
caggtggcga tggaggcaga gctgaggatc aaggtgaagg agatggacgt gctgctggag   1980
caggaggttg attaattaat catgtaatta gttatgtcac gcttacattc acgccctccc   2040
cccacatccg ctctaaccga aaaggaagga gttagacaac ctgaagtcta ggtccctatt   2100 tatttttta tagttatgtt agtattaaga acgttattta tatttcaaat ttttctttt    2160 tttctgtaca gacgcgtgta cgcatgtaac attatactga aaaccttgct tgagaaggtt   2220
ttgggacgct cgaaggcttt aatttgccgg attagaagcc gccgagcggg tgacagccct   2280
ccgaaggaag actctcctcc gtgcgtcctc gtcttcaccg gtcgcgttcc tgaaacgcag   2340
atgtgcctcg cgccgcactg ctccgaacaa taaagattct acaatactag cttttatggt   2400
tatgaagagg aaaaattggc agtaacctgg ccccacaaac cttcaaatga acgaatcaaa   2460
ttaacaacca taggatgata atgcgattag tttttagcc ttatttctgg ggtaattaat    2520
cagcgaagcg atgattttg atctattaac agatatataa atgcaaaaac tgcataacca   2580
ctttaactaa tactttcaac attttcggtt tgtattactt cttattcaaa tgtaataaaa   2640
gtatcaacaa aaaattgtta atataccctct atactttaac gtcaaggagg gcgcgccacc   2700
atggtgttta tcgtcaatct tttctcctgc accttatctg aaaccacggt tagctcaata   2760
aaatctgaag ctacggttag ctcaacattt actgccgtca cggccctgca attggtggct   2820
gagggtaagt tgcagtcggc gaagggtttc ggtggtggta cgattcacta cccaaccctc   2880
gcggccgaag caccctggtg gacgccgggc caaggccatg gttacgaggc gatcacctac   2940
```

```
ggctggctgg tcggcgaact gctgcgccgc gccgatgggc gtgggcctgg tctgttaggc    3000
gctattgccg tggttcctgg ttacgtttct tacgagaact ctatcaagtg gtggggaccg    3060
cgtctggctt cttggggctt tgtcgttgca cggccgttgg gcctggactt tcatgtgggc    3120
ctggcggatg aagagtttta tcgtgttgcc catatagcgc gcagcaaagc caatgcagca    3180
ctagataaca ttgctgatga caccgtcggc agtatagatc ctaagcggtt gggcgctatt    3240
ggctggtcag gtggcggcgg cgcgcttaaa ctggcaacgg agcgcagcac agtacgagcc    3300
attttgacca gtactaataa acctgaatgg cgacgcttcg ataaattctt atgtgcctgc    3360
gaggatgacc ggattgctga gactaagaaa tatgccaacg cgttttataa aaatgccgac    3420
atgctcgaag agttgacccg tgaacacagt atcgggccgg ataaaacatt attgacacaa    3480
actcggtttg gctggggtg cttggatcaa ccgcaagcag gggttaaaat tcatttgaa    3540 gagtaccttg atcaaaccca tggatttatc aatttgacgc cagtttcaca taaggcgaga    3600
gcaaatctga ttcagatgcc taatgccaca ttcggccttg gccgcgtgc ttttgggcat    3660 cctggtgcag gtggatcggt aggttttgcc gaccccgaac acgatgtagc gtttggtttc    3720
gtgactaata cattgggcc ttatgtagtt gagtttaaaa gccgtcatcc ctcatttat    3780 gcatataaag atggattggt gctgactgga aatgacgtcg actatgtgac tgattactat    3840
gcaacaaagc atgctgtaca tttagatgat ccacgtgcac agaagttggt cggaatattg    3900
gccggttgtc tgtaagttta aactcatgta attagttatg tcacgcttac attcacgccc    3960
tccccccaca tccgctctaa ccgaaaagga aggagttaga caacctgaag tctaggtccc    4020
tatttatttt tttatagtta tgttagtatt aagaacgtta tttatatttc aaatttttct    4080 ttttttttctg tacagacgcg tgtacgcatg taacattata ctgaaaacct tgcttgagaa    4140
ggttttggga cgctcgaagg ctttaatttg ccggattaga agccgccgag cgggtgacag    4200
ccctccgaag gaagactctc ctccgtgcgt cctcgtcttc accggtcgcg ttcctgaaac    4260
gcagatgtgc ctcgcgccgc actgctccga acaataaaga ttctacaata ctagctttta    4320
tggttatgaa gaggaaaaat tggcagtaac ctggccccac aaaccttcaa atgaacgaat    4380
caaattaaca accataggat gataatgcga ttagtttttt agccttattt ctggggtaat    4440
taatcagcga agcgatgatt tttgatctat taacagatat ataaatgcaa aaactgcata    4500
accactttaa ctaatacttt caacattttc ggtttgtatt acttcttatt caaatgtaat    4560
aaaagtatca acaaaaaatt gttaatatac ctctatactt taacgtcaag gagctcgagg    4620
ccaccatgaa gaagttgttg atttgtgcct tggctatgtt gttgtgttta cctgtattct    4680
cccagaagaa ggctaaaggt gcagcaagtc ctgctgtcgc tgttcctaag gctaagaatg    4740
taatcttgtt aatcggtgat ggtatgggt taacacacat ttcagctgga atgtacttta    4800
acaataacca atccaacttt gaaagatttc cagttgcagg tttgcagaaa gcatattctg    4860
ctagtgattt gattaccgat agtgctgctg gtgctaccgc tttcgcttct ggcattaaga    4920
cttacaacgg tgcaataggt gtgaatactg attctatgcc tgttaagacc atcttggaag    4980
aggcagaaga aagaggctta gcaactggaa tggtcgttac aagtacatta actcatgcta    5040
ctccagcttc atttgttgct catgttagga ataggaaatt cgatgaggaa attgcaacct    5100
tcttcttaaa gactgaaatc gacttccttgg caggtggtgg aaagaagttc tttgaacaga    5160
gagcagccga cggcagaaac ttgtaccaag agttaaagga taaggttat caggtatctg    5220 atttcactca gaagaatgca tcttctttgg cacctgatcc atctaagaac tttatctatt    5280
```

```
tcagtgcaga cgcagatcct gctaaagcct ccgaaggaag atcctatttg gctcctttat    5340
ctgtgttagc agctaatcat ttgaagaagc gtagtgagaa aggtttcttc ttgatggttg    5400
aatcttcaca aattgattgg ggaggacata acaatgaaag tgactacata gtctcagaag    5460
ttgtcgattt cgaccaaacc attggaaaga tattggattt cgcagctgct gatggagaaa    5520
ccttggtcat tgttactgcc gaccatgaaa ccggtggata tgcaatttct ccaggctccg    5580
aattaggcaa gatccgtggt gcttccacaa ctaaaggtca tactgcacaa ttgatccctg    5640
tattcgcttt cggtccaggt gctgaattgt ttgctggtgt ttatgagaac actgctatct    5700
acgtcaagat gaggcaagtc ttaggattct aaggtacctc atgtaattag ttatgtcacg    5760
cttacattca cgccctcccc ccacatccgc tctaaccgaa aaggaaggag ttagacaacc    5820
tgaagtctag gtccctattt atttttttat agttatgtta gtattaagaa cgttatttat    5880
atttcaaatt tttctttttt ttctgtacag acgcgtgtac gcatgtaaca ttatactgaa    5940
aaccttgctt gagaaggttt tgggacgctc gaaggcttta atttgccgga ttagaagccg    6000
ccgagcgggt gacagccctc cgaaggaaga ctctcctccg tgcgtcctcg tcttcaccgg    6060
tcgcgttcct gaaacgcaga tgtgcctcgc gccgcactgc tccgaacaat aaagattcta    6120
caatactagc ttttatggtt atgaagagga aaaattggca gtaacctggc cccacaaacc    6180
ttcaaatgaa cgaatcaaat taacaaccat aggatgataa tgcgattagt ttttttagcct    6240 tatttctggg gtaattaatc agcgaagcga tgattttga tctattaaca gatatataaa    6300
tgcaaaaact gcataaccac tttaactaat actttcaaca ttttcggttt gtattacttc    6360
ttattcaaat gtaataaaag tatcaacaaa aaattgttaa tatacctcta tactttaacg    6420
tcaaggaggg atccatgtct attccagaaa ctcaaaaagc cattatcttc tacgaatcca    6480
acggcaagtt ggagcataag gatatcccag ttccaaagcc aaagcccaac gaattgttaa    6540
tcaacgtcaa gtactctggt gtctgccaca ccgatttgca cgcttggcat ggtgactggc    6600
cattgccaac taagttacca ttagttggtg gtcacgaagg tgccggtgtc gttgtcggca    6660
tgggtgaaaa cgttaagggc tggaagatcg gtgactacgc cggtatcaaa tggttgaacg    6720
gttcttgtat ggcctgtgaa tactgtgaat tgggtaacga atccaactgt cctcacgctg    6780
acttgtctgg ttacacccac gacggttctt ccaagaata cgctaccgct gacgctgttc    6840
aagccgctca cattcctcaa ggtactgact ggctgaagt cgcgccaatc ttgtgtgctg    6900
gtatcaccgt atacaaggct ttgaagtctg ccaacttgag agcaggccac tgggcggcca    6960
tttctggtgc tgctggtggt ctaggttctt ggctgttca atatgctaag gcgatgggtt    7020
acagagtctt aggtattgat ggtggtccag gaaaggaaga attgtttacc tcgctcggtg    7080
gtgaagtatt catcgacttc accaaagaga aggacattgt tagcgcagtc gttaaggcta    7140
ccaacggcgg tgcccacggt atcatcaatg tttccgtttc cgaagccgct atcgaagctt    7200
ctaccagata ctgtagggcg aacggtactg ttgtcttggt tggttttgcca gccggtgcaa    7260 agtgctcctc tgatgtcttc aaccacgttg tcaagtctat ctccattgtc ggctcttacg    7320
tggggaacag agctgatacc agagaagcct agatttctt tgccagaggt ctagtcaagt    7380
ctccaataaa ggtagttggc ttatccagtt taccagaaat ttacgaaaag atggagaagg    7440
gccaaattgc tggtagatac gttgttgaca cttctaaata agaattctca tgtaattagt    7500
tatgtcacgc ttacattcac gccctccccc cacatccgct ctaaccgaaa aggaaggagt    7560
tagacaacct gaagtctagg tccctatttta tttttttata gttatgttag tattaagaac    7620
gttatttata tttcaaattt ttctttttttt tctgtacaga cgcgtgtacg catgtaacat    7680
```

```
tatactgaaa accttgcttg agaaggtttt gggacgctcg aaggctttaa tttgccggat   7740
tagaagccgc cgagcgggtg acagccctcc gaaggaagac tctcctccgt gcgtcctcgt   7800
cttcaccggt cgcgttcctg aaacgcagat gtgcctcgcg ccgcactgct ccgaacaata   7860
aagattctac aatactagct tttatggtta tgaagaggaa aaattggcag taacctggcc   7920
ccacaaacct tcaaatgaac gaatcaaatt aacaaccata ggatgataat gcgattagtt   7980
ttttagcctt atttctgggg taattaatca gcgaagcgat gattttgat ctattaacag     8040 atatataaat gcaaaaactg cataaccact ttaactaata ctttcaacat tttcggtttg   8100
tattacttct tattcaaatg taataaaagt atcaacaaaa aattgttaat atacctctat   8160
actttaacgt caaggaggcg gccgccatgg tgagcaaggg cgaggagctg ttcaccgggg   8220
tggtgcccat cctggtcgag ctggacggcg acgtaaacgg ccacaagttc agcgtgtccg   8280
gcgagggcga gggcgatgcc acctacggca agctgaccct gaagttcatc tgcaccaccg   8340
gcaagctgcc cgtgccctgg cccaccctcg tgaccacctt cggctacggc ctgcaatgct   8400
tcgcccgcta ccccgaccac atgaagctgc acgacttctt caagtccgcc atgcccgaag   8460
gctacgtcca ggagcgcacc atcttcttca aggacgacgg caactacaag acccgcgccg   8520
aggtgaagtt cgagggcgac accctggtga accgcatcga gctgaagggc atcgacttca   8580
aggaggacgg caacatcctg gggcacaagc tggagtacaa ctacaacagc cacaacgtct   8640
atatcatggc cgacaagcag aagaacggca tcaaggtgaa cttcaagatc cgccacaaca   8700
tcgaggacgg cagcgtgcag ctcgccgacc actaccagca gaacacccc atcggcgacg     8760 gccccgtgct gctgcccgac aaccactacc tgagctacca gtccgccctg agcaaagacc   8820
ccaacgagaa gcgcgatcac atggtcctgc tggagttcgt gaccgccgcc gggatcactc   8880
tcggcatgga cgagctgtac aagtaatcta gagggccgca tcatgtaatt agttatgtca   8940
cgcttacatt cacgccctcc ccccacatcc gctctaaccg aaaaggaagg agttagacaa   9000
cctgaagtct aggtccctat ttatttttt atagttatgt tagtattaag aacgttattt     9060
atatttcaaa ttttcttttt tttctgtac agacgcgtgt acgcatgtaa cattatactg    9120
aaaaccttgc ttgagaaggt tttgggacgc tcgaaggctt taatttgcgg ccctgcatta   9180
atgaatcggc caacgcgcgg ggagaggcgg tttgcgtatt gggcgctctt ccgcttcctc   9240
gctcactgac tcgctgcgct cggtcgttcg gctgcggcga gcggtatcag ctcactcaaa   9300
ggcggtaata cggttatcca cagaatcagg ggataacgca ggaaagaaca tgtgagcaaa   9360
aggccagcaa aagcccagga accgtaaaaa ggccgcgttg ctggcgtttt tccataggct   9420 ccgccccct gacgagcatc acaaaaatcg acgctcaagt cagaggtggc gaaacccgac      9480
aggactataa agataccagg cgtttccccc tggaagctcc ctcgtgcgct ctcctgttcc   9540
gaccctgccg cttaccggat acctgtccgc ctttctccct tcgggaagcg tggcgctttc   9600
tcatagctca cgctgtaggt atctcagttc ggtgtaggtc gttcgctcca agctgggctg   9660
tgtgcacgaa ccccccgttc agcccgaccg ctgcgcctta tccggtaact atcgtcttga   9720
gtccaacccg gtaagacacg acttatcgcc actggcagca gccactggta acaggattag   9780
cagagcgagg tatgtaggcg gtgctacaga gttcttgaag tggtggccta actacggcta   9840
cactagaagg acagtatttg gtatctgcgc tctgctgaag ccagttacct tcggaaaaag   9900
agttggtagc tcttgatccg gcaaacaaac caccgctggt agcggtggtt tttttgtttg   9960
caagcagcag attacgcgca gaaaaaaagg atctcaagaa gatcctttga tcttttctac  10020
```

```
ggggtctgac gctcagtgga acgaaaactc acgttaaggg attttggtca tgagattatc   10080
aaaaaggatc ttcacctaga tccttttaaa ttaaaaatga agttttaaat caatctaaag   10140
tatatatgag taaacttggt ctgacagtta ccaatgctta atcagtgagg cacctatctc   10200
agcgatctgt ctatttcgtt catccatagt tgcctgactc cccgtcgtgt agataaactac  10260 gatacgggag cgcttaccat ctggccccag tgctgcaatg ataccgcgag acccacgctc   10320
accggctcca gatttatcag caataaacca gccagccgga agggccgagc gcagaagtgg   10380
tcctgcaact ttatccgcct ccatccagtc tattaattgt tgccgggaag ctagagtaag   10440
tagttcgcca gttaatagtt tgcgcaacgt tgttggcatt gctacaggca tcgtggtgtc   10500
actctcgtcg tttggtatgg cttcattcag ctccggttcc caacgatcaa ggcgagttac   10560
atgatccccc atgttgtgca aaaagcggt tagctccttc ggtcctccga tcgttgtcag   10620
aagtaagttg gccgcagtgt tatcactcat ggttatggca gcactgcata attctcttac   10680
tgtcatgcca tccgtaagat gcttttctgt gactggtgag tactcaacca agtcattctg   10740
agaatagtgt atgcggcgac cgagttgctc ttgcccggcg tcaatacggg ataatagtgt   10800
atcacatagc agaactttaa aagtgctcat cattggaaaa cgttcttcgg ggcgaaaact   10860
ctcaaggatc ttaccgctgt tgagatccag ttcgatgtaa cccactcgtg cacccaactg   10920
atcttcagca tcttttactt tcaccagcgt ttctgggtga gcaaaaacag gaaggcaaaa   10980
tgccgcaaaa aagggaataa gggcgacacg gaaatgttga atactcatac tcttcctttt   11040
tcaatgggta ataactgata taattaaatt gaagctctaa tttgtgagtt tagtatacat   11100
gcatttactt ataatacagt ttttagtttt gctggccgc atcttctcaa atatgcttcc    11160
cagcctgctt ttctgtaacg ttcaccctct accttagcat cccttccctt tgcaaatagt   11220
cctcttccaa caataataat gtcagatcct gtagagacca catcatccac ggttctatac   11280
tgttgaccca atgcgtctcc cttgtcatct aaacccacac cgggtgtcat aatcaaccaa   11340
tcgtaacctt catctcttcc acccatgtct ctttgagcaa taaagccgat aacaaaatct   11400
ttgtcgctct tcgcaatgtc aacagtaccc ttagtatatt ctccagtaga tagggagccc   11460
ttgcatgaca attctgctaa catcaaaagg cctctaggtt cctttgttac ttcttctgcc   11520
gcctgcttca aaccgctaac aatacctggg cccaccacac cgtgtgcatt cgtaatgtct   11580
gcccattctg ctattctgta tacacccgca gagtactgca atttgactgt attaccaatg   11640
tcagcaaatt ttctgtcttc gaagagtaaa aaattgtact tggcggataa tgcctttagc   11700
ggcttaactg tgccctccat ggaaaaatca gtcaagatat ccacatgtgt ttttagtaaa   11760
caaattttgg gacctaatgc ttcaactaac tccagtaatt ccttggtggt acgaacatcc   11820
aatgaagcac acaagtttgt ttgcttttcg tgcatgatat taaatagctt ggcagcaaca   11880
ggactaggat gagtagcagc acgttcctta tatgtagctt tcgacatgat ttatcttcgt   11940
ttcctgcagg ttttttgttct gtgcagttgg gttaagaata ctgggcaatt tcatgtttct   12000
tcaacactac atatgcgtat atataccaat ctaagtctgt gctccttcct tcgttcttcc   12060
ttctgttcgg agattaccga atcaaaaaaa tttcaaagaa accgaaatca aaaaaagaa    12120 taaaaaaaaa atgatgaatt gaattgaaaa gctagcttat cgatgataag ctgtcaaaga   12180
tgagaattaa ttccacggac tatagactat actagatact ccgtctactg tacgatacac   12240
ttccgctcag gtccttgtcc tttaacgagg ccttaccact cttttgttac tctattgatc   12300
cagctcagca aaggcagtgt gatctaagat tctatcttcg cgatgtagta aaactagcta   12360
gaccgagaaa gagactagaa atgcaaaagg cacttctaca atggctgcca tcattattat   12420
```

-continued

```
ccgatgtgac gctgcagctt ctcaatgata ttcgaatacg ctttgaggag atacagccta   12480
atatccgaca aactgtttta cagatttacg atcgtacttg ttacccatca ttgaattttg   12540
aacatccgaa cctgggagtt ttccctgaaa cagatagtat atttgaacct gtataataat   12600
atatagtcta gcgctttacg gaagacaatg tatgtatttc ggttcctgga gaaactattg   12660
catctattgc ataggtaatc ttgcacgtcg catccccggt tcattttctg cgtttccatc   12720
ttgcacttca atagcatatc tttgttaacg aagcatctgt gcttcatttt gtagaacaaa   12780
aatgcaacgc gagagcgcta attttcaaa caaagaatct gagctgcatt tttacagaac    12840
agaaatgcaa cgcgaaagcg ctattttacc aacgaagaat ctgtgcttca tttttgtaaa   12900
acaaaaatgc aacgcgacga gagcgctaat ttttcaaaca aagaatctga gctgcatttt   12960
tacagaacag aaatgcaacg cgagagcgct attttaccaa caaagaatct atacttcttt   13020
tttgttctac aaaaatgcat cccgagagcg ctatttttct aacaaagcat cttagattac   13080 ttttttttctc ctttgtgcgc tctataatgc agtctcttga taactttttg cactgtaggt  13140
ccgttaaggt tagaagaagg ctactttggt gtctattttc tcttccataa aaaaagcctg   13200
actccacttc ccgcgtttac tgattactag cgaagctgcg ggtgcatttt ttcaagataa   13260
aggcatcccc gattatattc tataccgatg tggattgcgc atactttgtg aacagaaagt   13320
gatagcgttg atgattcttc attggtcaga aaattatgaa cggtttcttc tattttgtct   13380
ctatatacta cgtataggaa atgtttacat tttcgtattg ttttcgattc actctatgaa   13440
tagttcttac tacaattttt ttgtctaaag agtaatacta gagataaaca taaaaaatgt   13500
agaggtcgag tttagatgca agttcaagga gcgaaaggtg gatgggtagg ttatataggg   13560
atatagcaca gagatatata gcaaagagat acttttgagc aatgtttgtg gaagcggtat   13620
tcgcaatggg aagctccacc ccggttgata atcagaaaag ccccaaaaac aggaagattg   13680
tataagcaaa tatttaaatt gtaaacgtta atattttgtt aaaattcgcg ttaaattttt    13740
gttaaatcag ctcattttt aacgaatagc ccgaaatcgg caaatccct tataaatcaa     13800 aagaatagac cgagatagg ttgagtgttg ttccagtttc aacaagagt ccactattaa     13860 agaacgtgga ctccaacgtc aaagggcgaa aaagggtcta tcagggcgat ggcccactac   13920
gtgaaccatc accctaatca agttttttgg ggtcgaggtg ccgtaaagca gtaaatcgga   13980
agggtaaacg gatgccccca tttagagctt gacggggaaa gccggcgaac gtggcgagaa   14040
aggaagggaa gaaagcgaaa ggagcggggg ctagggcggt gggaagtgta ggggtcacgc   14100
tgggcgtaac caccacaccc gccgcgctta atggggcgct acagggcgcg tggggatgat   14160
ccactagt                                                             14168
```

BIOLOGICAL DEVICES FOR PRODUCING OXIDIZED ZINC AND APPLICATIONS THEREOF

CROSS REFERENCE TO RELATED APPLICATIONS

This application claims priority upon U.S. provisional application Serial Nos. 62/557,340 filed on Sep. 12, 2017 and 62/650,356 filed Mar. 30, 2018. These applications are hereby incorporated by reference in their entirety.

CROSS REFERENCE TO SEQUENCE LISTING

The genetic components described herein are referred to by sequence identifier numbers (SEQ ID NO). The SEQ ID NOs correspond numerically to the sequence identifiers <400>1, <400>2, etc. The Sequence Listing, in written computer readable format (CRF), is incorporated by reference in its entirety.

BACKGROUND

Zinc oxide is widely used across a variety of industries. Its ultraviolet-absorbing properties have been exploited in materials such as paints and coatings, plastics, and even sunscreen creams. Zinc oxide is employed industrially in the curing and vulcanization of rubber and latex, to impart heat resistance and abrasion resistance to rubber and plastic products, and in the medical industry in applications from wound healing to dental cement. Further, zinc oxide is a precursor material for other zinc salts including zinc diacrylate (used in the manufacture of golf balls), zinc chromate (used for anti-corrosion purposes), zinc borate and zinc chloride (used as flame retardants), zinc gluconate (used in cold-prevention lozenges and sprays), and zinc dithiophosphate (an anti-wear ingredient in lubricants), among others.

Production of zinc oxide can be expensive. Zinc ores must first be ground and sometimes roasted to produce zinc oxide. Sulfur dioxide is a typical byproduct of the process of roasting zinc ores; when this compound is released into the atmosphere, it contributes to acid rain. Toxic cadmium vapor is another byproduct of zinc refining, and further, zinc mining operations can lead to significant levels of heavy metal pollution in the air, in soil, and in waterways, causing concerns for human health, agriculture, and wildlife. Furthermore, the use of impure sources of zinc can lead to impurities and discoloration in the final product, affecting its use as a pigment, and can cause material to aggregate in processing furnaces and other equipment, reducing the lifetime of said equipment. Finally, although zinc oxide is non-toxic, fumes such as those generated when zinc and/or zinc alloys are vaporized or melted and oxidized can be quite hazardous, as well.

What is needed is a new method for producing oxidized zinc. Ideally, the method would be inexpensive to conduct and would work with a variety of starting materials including recycled materials and impure zinc sources. Furthermore, the method would not require the use of harsh chemicals or high-temperature furnaces and would generate fewer health and environmental hazards than traditional methods for producing zinc oxide.

SUMMARY

Described herein are biological devices and methods for using the same to produce oxidized zinc. The biological devices include microbial cells transformed with a DNA construct containing genes for producing a zinc-related protein, an alkaline phosphatase, and an alcohol dehydrogenase. In some instances, the biological devices also include a gene for lipase. The oxidized zinc compositions produced herein have numerous applications.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIG. 4A represents 30 minutes of UV exposure, FIG. 4B represents 1 hour of UV exposure, and FIG. 4C represents 24 hours of UV exposure. In each, the leftmost petri dish is a control bacterial culture without treatment, the center petri dish is a low dilution of a bacterial culture treated with the extracts disclosed herein, and the right petri dish is a high dilution of a bacterial culture treated with the extracts disclosed herein.

FIG. 5A represents a culture prior to UV exposure. FIG. 5B represents bacterial cultures after 30 minutes of UV exposure in an untreated control (left panel) and a culture treated with the extracts disclosed herein (right panel). FIG. 5C represents bacterial cultures after 1 hour of UV exposure in an untreated control (left panel) and a culture treated with the extracts disclosed herein (right panel). FIG. 5D represents the same cultures, respectively, after 24 hours of exposure to UV light.

FIG. 6A represents a culture prior to UV exposure treated with <100 nm zinc oxide nanopowder. FIG. 6B represents this same culture after 30 minutes of UV exposure (left panel), 1 hour of UV exposure (center panel), and after 24 hours of UV exposure (right panel).

FIG. 7A shows zinc oxide nanopowder (<100 nm particle size), which dissolves at pH 2. FIG. 7B shows an extract from the devices disclosed herein, which dissolves at a pH of 6.89. FIG. 7C shows an acid digestion of zinc oxide nanopowder (required for dissolution of the sample). FIG. 7D shows an acid digestion of extracts from the devices disclosed herein.

FIG. 8A represents current (in A) versus potential difference (in V) for zinc nanopowder in nitric acid. FIG. 8B represents current versus potential difference for the undigested extracts disclosed herein.

FIG. 9A is a standard curve for zinc. FIG. 9B is a standard curve for zinc oxide in 65% nitric oxide. FIG. 9C is a standard curve for the zinc oxide nanopowder used as a control herein. FIG. 9D is a standard curve for extracts produced by the biological devices disclosed herein. FIG. 9E is a standard curve for the extracts produced from the biological devices disclosed herein for lower concentrations than in FIG. 9D, wherein the samples were not filtered. FIG. 9F is a standard curve for the extracts produced by the biological devices disclosed herein wherein the samples were filtered with a 0.2 µm nylon filter prior to analysis.

DETAILED DESCRIPTION

Figure 1A:
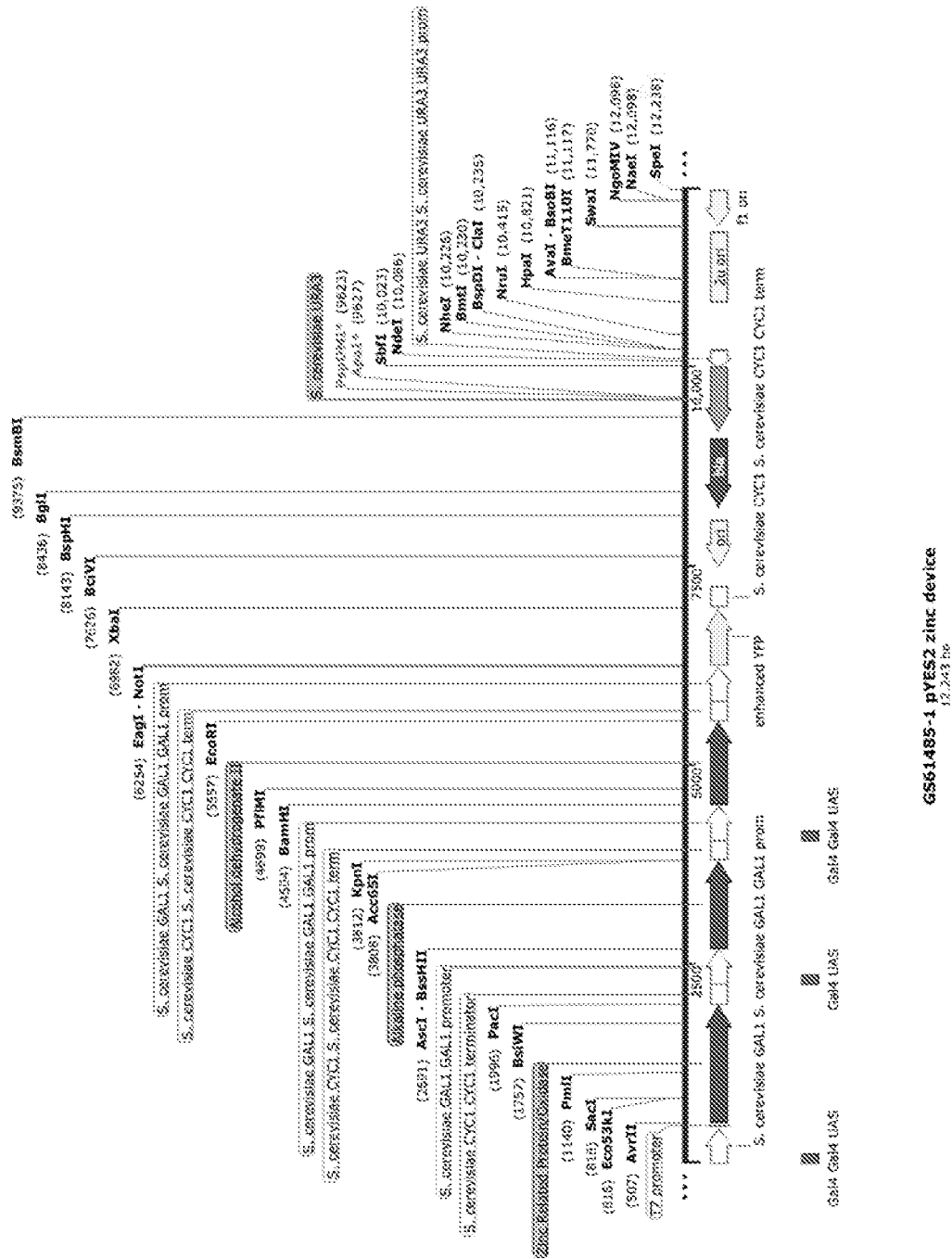
FIGS. 1A and 1B show, respectively, a linear and circular schematic of a constructed pYES2 plasmid showing the direction, placement, and size of genetic parts used of an exemplary DNA device described herein.

Before the present compounds, compositions, articles, devices, and/or methods are disclosed and described, it is to be understood that the aspects described below are not limited to specific compounds, synthetic methods, or uses, as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an," and "the" include plural referents unless the context clearly dictates otherwise. Thus, for example, reference to "a restriction enzyme" includes mixtures of two or more such restriction enzymes, and the like.

"Optional" or "optionally" means that the subsequently described event or circumstance can or cannot occur, and that the description includes instances where the event or circumstance occurs and instances where it does not. For example, the phrase "optionally includes a reporter protein" means that the reporter protein may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc., of these materials are disclosed, that while specific reference to each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed, it is understood that each of these additional steps can be performed with any specific embodiment or combination of embodiments of the disclosed methods, and that each such combination is specifically contemplated and should be considered disclosed.

Described herein is a process for producing oxidized zinc using microbial cells that includes (a) making a DNA construct containing genes for producing a zinc-related protein, an alkaline phosphatase, and an alcohol dehydrogenase, (b) introducing the DNA construct into host microbial cells via transformation or transfection, and (c) culturing the microbial host cells to produce oxidized zinc.

I. DNA Constructs

DNA constructs are provided herein for the production of oxidized zinc. It is understood that one way to define the variants and derivatives of the genetic components and DNA constructs described herein is in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed according to published algorithms (see Zuker, M., *Science,* 244:48-52, 1989; Jaeger et al., *Proc. Natl. Acad. Sci. USA,* 86:7706-7710, 1989; and Jaeger et al., *Methods Enzymol.,* 183:281-306, 1989, which are herein incorporated by reference for at least material related to nucleic acid alignment.

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of mutations and homology can be combined together in any combination, such as embodiments that have at least 70%, 75%, 80%, 85%, 90%, 95%, or 99% homology to a particular sequence wherein the variants are conservative or silent mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, genes of interest can be incorporated into a DNA construct. In a further aspect, the DNA construct can be incorporated as part of a vector for transfection into microbial cells. In a still further aspect, the vector can be a plasmid, a phagemid, a cosmid, a yeast artificial chromosome, a bacterial artificial chromosome, a virus, a phage, or a transposon. In another aspect, the microorganisms are fungi or bacteria. In one aspect, the fungi are yeasts such as, for example, *Saccharomyces cerevisiae*. In another aspect, the bacteria are *Escherichia coli*.

Vectors capable of high levels of expression of recombinant genes and proteins are well known in the art. Vectors useful for the transformation of a variety of host cells are common and commercially available and include, for example, pWLneo, pSV2cat, pOG44, pXT1, pSG, pSVK3, pBSK, pBR322, pYES, pYES2, pBSKII, and pUC. The skilled practitioner will be able to choose a plasmid based on such factors as (a) the amount of nucleic acid (i.e., number of genes and other elements) to be inserted, (b) the host organism, (c) culture conditions for the host organism, and other related factors.

In one aspect, the DNA construct includes the following genetic components: (a) a gene that expresses zinc-related protein; (b) a gene that expresses alkaline phosphatase; and (c) a gene that expresses alcohol dehydrogenase.

In one aspect, the nucleic acids (e.g., genes that express zinc-related protein, alkaline phosphatase, and alcohol dehydrogenase) used in the DNA constructs described herein can be amplified using polymerase chain reaction (PCR) prior to being ligated into a plasmid or other vector. Typically, PCR amplification techniques make use of primers, or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for both efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the skilled practitioner with primer design. Primers can optionally incorporate restriction enzyme recognition sites at their 5' ends to assist in later ligation into plasmids or other vectors.

PCR can be carried out using purified DNA, unpurified DNA that is integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the plasmid can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of that coding sequence.

As used herein, "expression" refers to transcription and/or accumulation of an mRNA derived from a gene or DNA fragment. Expression may also be used to refer to translation of mRNA into a peptide, polypeptide, or protein.

In one aspect, the gene that expresses zinc-related protein is isolated from an animal. In a further aspect, the animal is a fish such as, for example, Atlantic salmon. In an alternative aspect, the gene that expresses zinc-related protein is isolated from a bacterium. In one aspect, the bacterium is a *Streptomyces, Polaribacter, Kitasatospora, Actinobacter, Azospirillum, Clostridium*, or *Collimonas, Micromonospora* species. In a still further aspect, the gene that expresses zinc-related protein is isolated from an alga. In one aspect, the alga is *Guillardia theta*. In a further aspect, the gene that expresses zinc-related protein has SEQ ID NO. 1 or at least 70% homology thereto, at least 75% homology thereto, at least 80% homology thereto, at least 85% homology thereto, at least 90% homology thereto, or at least 95% homology thereto. In another aspect, the zinc-related protein is calmodulin or another zinc-binding protein, or a homolog thereof. In one aspect, the gene that expresses zinc-related protein is isolated from *Streptomyces zinciresistens* and can be found in GenBank with GI number EGX59011.1.

Other sequences expressing zinc-related protein or related or homologous genes can be identified in a database such as, for example, GenBank. In one aspect, sequences useful herein include those with the GI numbers listed in Table 1:

TABLE 1

Zinc-Related Protein Genes

| Source Organism | Sequence Description | GI Number |
| --- | --- | --- |
| *Streptomyces lincolnensis* | genomic DNA | CP016438.1 |
| *Streptomyces* sp. 4F | genomic DNA | CP013142.1 |
| *Streptomyces collinus* | genomic DNA | CP006259.1 |
| *Streptomyces avermitilis* | genomic DNA | BA000030.4 |
| *Streptomyces* sp. 3124.6 | genomic DNA | LT670819.1 |
| *Streptomyces* sp. 1H-SSA4 | genomic DNA | CP022161.1 |
| *Streptomyces parvulus* | genomic DNA | CP015866.1 |

TABLE 1-continued

Zinc-Related Protein Genes

| Source Organism | Sequence Description | GI Number |
|---|---|---|
| Streptomyces ambofaciens | genomic DNA | CP012949.1 |
| Streptomyces ambofaciens | genomic DNA | CP012382.1 |
| Streptomyces scabiei | genomic DNA | FN554889.1 |
| Streptomyces davawensis | genomic DNA | HE971709.1 |
| Polaribacter sp. SA4-12 | genomic DNA | CP019334.1 |
| Streptomyces sp. 11-1-2 | genomic DNA | CP022545.1 |
| Streptomyces sp. CdTB01 | genomic DNA | CP013743.1 |
| Kitasatospora setae | genomic DNA | AP010968.1 |
| Streptomyces pluripotens | genomic DNA | CP022433.1 |
| Streptomyces pluripotens | genomic DNA | CP021080.1 |
| Streptomyces pactum | genomic DNA | CP019724.1 |
| Polaribacter sp. Hell_33_78 | genomic DNA | LT629794.1 |
| Streptomyces sp. TLI_053 | genomic DNA | LT629775.1 |
| Streptomyces pactum | genomic DNA | CP016795.1 |
| Streptomyces puniciscabiei | genomic DNA | CP017248.1 |
| Streptomyces griseochromogenes | genomic DNA | CP016279.1 |
| Streptomyces incarnates | genomic DNA | CP011497.1 |
| Kitasatospora auregfaciens | genomic DNA | CP020567.1 |
| Streptomyces sp. S10(2016) | genomic DNA | CP015098.1 |
| Streptomyces reticuli | genomic DNA | LN997842.1 |
| Actinobacteria bacterium IMCC25003 | genomic DNA | CP015603.1 |
| Polaribacter sp. KT25b | genomic DNA | LT629752.1 |
| Streptomyces hygroscopicus | genomic DNA | CP013219.1 |
| Streptomyces sp. Mg1 | genomic DNA | CP011664.1 |
| Azospirillum brasilense | genomic DNA | CP007796.1 |
| Streptomyces hygroscopicus | genomic DNA | CP003720.1 |
| Streptomyces hygroscopicus | genomic DNA | CP003275.1 |
| Clostridium cochlearium | genomic DNA | LT906477.1 |
| Collimonas arenae | genomic DNA | CP009962.1 |
| Polaribacter sp. MED152 | genomic DNA | CP004349.1 |
| Streptomyces sp. S8 | genomic DNA | CP015362.1 |
| Micromonospora echinofusca | genomic DNA | LT607733.1 |
| Streptomyces sp. PBH53 | genomic DNA | CP011799.1 |
| Streptomyces fulvissimus | genomic DNA | CP005080.1 |
| Streptomyces katrae | genomic DNA | CP020042.1 |
| Streptomyces silaceus | genomic DNA | CP015588.1 |
| Streptomyces venezuelae | genomic DNA | CP018074.1 |
| Salmo solar | calmodulin | XM_014213459.1 |
| Streptomyces venezuelae | genomic DNA | FR845719.1 |
| Salmo solar | calmodulin | BT059493.1 |
| Salmo solar | calmodulin | BT045544.1 |
| Streptomyces albireticuli | genomic DNA | CP021744.1 |
| Streptomyces sp. 3211 | genomic DNA | CP020039.1 |
| Clostridium sporogenes | genomic DNA | CP011663.1 |
| Clostridium sporogenes | genomic DNA | CP009225.1 |
| Clostridium botulinum | genomic DNA | CP006902.1 |
| Guillardia theta | genomic DNA | XM_005830304.1 |

In one aspect, the gene that expresses alkaline phosphatase is isolated from an insect. In a further aspect, the insect is a fruit fly such as, for example, from the genus Ceratitis. In another aspect, the gene that expresses alkaline phosphatase is isolated from a fungus. In a further aspect, the fungus can be a pathogenic or non-pathogenic fungus, a fungus that forms a symbiotic relationship with plant roots, a yeast, a slime mold, or a mitosporic fungus. In a still further aspect, the fungus can be from the genus Vanderwaltozyma, Dactylellina, Funneliformis, Gigaspora, Cyberlindnera, Schizosaccharomyces, Candida, Polysphondylium, Trichophyton, Lobosporangium, Hyphopichia, or another common fungal genus. In a still another aspect, the gene that expresses alkaline phosphatase is isolated from a bacterium. In one aspect, the bacterium can be Gram-negative or Gram-positive, can be aerobic or anaerobic, can be spore-forming or non-spore forming, can be motile or sessile, can have a bacillus or coccus shape, can be found in a freshwater or marine environment or associated with the microbiome of a human or other animal, or can be adapted to an extreme condition such as cold or a hyperthermophilic environment. In one aspect, the bacterium is from one of the following genera: Haliscomenobacter, Alkalitalea, Owenweeksia, Porphyromonadaceae, Aequorivita, Alteromoas, Polaribacter, Enterococcus, Xenorhabdus, Bacteroides, Maribacter, Thermotoga, Dokdonia, Bacillus, Sphingobacterium, Mucilaginibacter, Cellulophaga, or Glaciecola. In a further aspect, the gene that expresses alkaline phosphatase has SEQ ID NO. 2 or at least 70% homology thereto, at least 75% homology thereto, at least 80% homology thereto, at least 85% homology thereto, at least 90% homology thereto, or at least 95% homology thereto. In one aspect, the gene that expresses an alkaline phosphatase is isolated from Haliscomenobacter hydrossis and can be found in GenBank with GI number AEE52072.1.

Other sequences expressing alkaline phosphatase or related or homologous genes can be identified in a database such as, for example, GenBank. In one aspect, sequences useful herein include those with the GI numbers listed in Table 2:

TABLE 2

Alkaline Phosphatase Genes

| Source Organism | Sequence Description | GI Number |
|---|---|---|
| Haliscomenobacter hydrossis | genomic DNA | CP002691.1 |
| Alkalitalea saponilacus | genomic DNA | CP021904.1 |
| Uncultured bacterium | genomic DNA | KU516288.1 |
| Uncultured bacterium | genomic DNA | KU516232.1 |
| Uncultured bacterium | genomic DNA | KU516199.1 |
| Uncultured bacterium | genomic DNA | KU516115.1 |
| Owenweeksia hongkongensis | genomic DNA | CP003156.1 |
| Vanderwaltozyma polyspora | hypothetical protein | XM_001645979.1 |
| Dactylellina haptotyla | hypothetical protein | XM_011111730.1 |
| Porphyromonadaceae bacterium | genomic DNA | LN515532.1 |
| Aequorivita sublithincola | genomic DNA | CP003280.1 |
| Alteromonas macleodii | genomic DNA | CP014323.1 |
| Alteromonas macleodii | genomic DNA | CP003873.1 |
| Polaribacter sp. | genomic DNA | CP019334.1 |
| Funneliformis mosseae | alkaline phosphatase | CP002528.1 |
| Enterococcus faecalis | genomic DNA | JX997747.1 |
| Enterococcus faecalis | genomic DNA | CP022712.1 |
| Enterococcus faecalis | genomic DNA | CP015883.1 |
| Enterococcus faecalis | genomic DNA | CP021161.1 |
| Enterococcus faecalis | genomic DNA | CP015410.2 |
| Enterococcus faecalis | genomic DNA | CP019512.1 |
| Enterococcus faecalis | genomic DNA | CP015998.1 |
| Enterococcus faecalis | genomic DNA | CP018102.1 |
| Enterococcus faecalis | genomic DNA | AP017623.1 |
| Enterococcus faecalis | genomic DNA | CP014949.1 |
| Enterococcus faecalis | genomic DNA | CP008816.1 |
| Xenorhabdus poinarii | genomic DNA | FO704551.1 |
| Enterococcus faecalis | genomic DNA | CP004081.1 |
| Enterococcus faecalis | genomic DNA | HF558530.1 |
| Enterococcus faecalis | genomic DNA | CP003726.1 |
| Enterococcus faecalis | genomic DNA | CP002621.1 |
| Enterococcus faecalis | genomic DNA | CP002491.1 |
| Enterococcus sp. | genomic DNA | FP929058.1 |
| TnphoZ mutagenesis vector | genomic DNA | AY028776.1 |
| Enterococcus faecalis | genomic DNA | AE016830.1 |
| Cloning vector | genomic DNA | AF167172.1 |
| Bacteroides helcogenes | genomic DNA | CP002352.1 |
| Maribacter sp. | genomic DNA | CP002157.1 |
| Gigaspora margarita | alkaline phosphatase | AB114299.1 |
| Cyberlindnera fabianii | genomic DNA | LK052911.1 |
| Thermotoga naphthophila | genomic DNA | CP001839.1 |
| Thermotoga sp. | genomic DNA | CP000969.1 |
| Thermotoga sp. | 16S RNA | AJ872273.1 |
| Thermotoga naphthophila | 16S RNA | AJ872268.1 |
| Enterococcus faecalis | genomic DNA | CP018004.1 |
| Dokdonia donghaensis | genomic DNA | CP015125.1 |
| Bacillus simplex | genomic DNA | CP011008.1 |

TABLE 2-continued

Alkaline Phosphatase Genes

| Source Organism | Sequence Description | GI Number |
|---|---|---|
| Schizosaccharomyces pombe | vacuolar membrane alkaline phosphatase | NM_001022665.2 |
| Candida dubliniensis | alkaline phosphatase precursor | XM_002417429.1 |
| Candida dubliniensis | genomic DNA | FM992688.1 |
| Schizosaccharomyces pombe | genomic DNA | CU329671.1 |
| Schizosaccharomyces pombe | alkaline phosphatase | AF316541.1 |
| Polysphondylium pallidum | alkaline phosphatase | XM_020573858.1 |
| Bacillus anthracis | genomic DNA | CP019726.1 |
| Proteiniphilum saccharofermetans | genomic DNA | LT605205.1 |
| Bacillus cereus | genomic DNA | CP018935.1 |
| Bacillus cereus | genomic DNA | CP018931.1 |
| Bacillus anthracis | genomic DNA | AP014833.1 |
| Bacillus cereus | genomic DNA | CP009605.1 |
| Bacillus thuringiensis | genomic DNA | CP010088.1 |
| Bacillus anthracis | genomic DNA | CP009981.1 |
| Bacillus cereus | genomic DNA | CP009968.1 |
| Bacillus anthracis | genomic DNA | CP009902.1 |
| Bacillus thuringiensis | genomic DNA | CP009720.1 |
| Bacillus anthracis | genomic DNA | CP009598.1 |
| Bacillus cereus | genomic DNA | CP009596.1 |
| Bacillus anthracis | genomic DNA | CP009700.1 |
| Bacillus anthracis | genomic DNA | CP009544.1 |
| Bacillus anthracis | genomic DNA | CP009541.1 |
| Bacillus anthracis | genomic DNA | CP009476.1 |
| Bacillus anthracis | genomic DNA | CP009464.1 |
| Bacillus anthracis | genomic DNA | CP009331.1 |
| Bacillus anthracis | genomic DNA | CP009325.1 |
| Bacillus anthracis | genomic DNA | CP008752.1 |
| Bacillus anthracis | genomic DNA | CP007618.1 |
| Bacillus cereus | genomic DNA | CP003747.1 |
| Bacillus coagulans | genomic DNA | CP003056.1 |
| Trichophyton verrucosum | hypothetical protein | XM_003019232.1 |
| Tricophyton benhamiae | hypothetical protein | XM_003016737.1 |
| Bacillus anthracis | genomic DNA | EF039850.1 |
| Sphingobacterium mizutaii | genomic DNA | LT906468.1 |
| Sphingobacteriaceae bacterium | genomic DNA | CP021237.1 |
| Ceratitis capitate | membrane-bound alkaline phosphatase | XM_004522406.3 |
| Candida tanzawaensis | alkaline phosphatase-like protein | XM_020211106.1 |
| Mucilaginibacter sp. | genomic DNA | CP014773.1 |
| Thermotoga maritima | genomic DNA | CP011108.1 |
| Thermotoga maritima | genomic DNA | CP011107.1 |
| Thermotoga maritima | genomic DNA | CP010967.1 |
| Cellulophaga baltica | genomic DNA | CP009976.1 |
| Thermotoga sp. | genomic DNA | CP003409.1 |
| Dokdonia sp. | genomic DNA | CP009301.1 |
| Thermotoga maritima | genomic DNA | CP007013.1 |
| Thermotoga maritima | genomic DNA | CP004077.1 |
| Glaciecola psychrophila | genomic DNA | CP003837.1 |
| Cellulophaga algicola | genomic DNA | CP002453.1 |
| Thermotoga petrophila | genomic DNA | CP000702.1 |
| Thermotoga maritima | genomic DNA | AE000512.1 |
| Lobosporangium transversal | alkaline phosphatase-like protein | XM_022029226.1 |
| Bacillus horikoshii | genomic DNA | CP020880.1 |
| Hyphopichia burtonii | alkaline phosphatase-like protein | XM_020222701.1 |

In one aspect, the gene that expresses alcohol dehydrogenase is isolated from a fungus. In a further aspect, the fungus is a yeast such as, for example, *Saccharomyces cerevisiae*. In a still further aspect, the *S. cerevisiae* is from strain S288c, N85, Y12, ySR127, AHY0914, YJM451, YJM470, YJM554, YJM555, YJM682, YJM689, YJM972, YJM975, YJM978, YJM996, YJM1083, YJM1133, YJM1190, YJM1208, YJM1250, YJM1307, YJM1356, YJM1381, YJM1383, YJM1385, YJM1386, YJM1388, YJM1389, YJM1419, YJM1433, YJM1456, YJM1460, YJM1526, YJM1592, or YJM1615. In an alternative aspect, the *S. cerevisiae* is a wild type strain. In a further aspect, the gene that expresses alcohol dehydrogenase has SEQ ID NO. 3 or at least 70% homology thereto, at least 75% homology thereto, at least 80% homology thereto, at least 85% homology thereto, at least 90% homology thereto, or at least 95% homology thereto. In one aspect, the gene that expresses alcohol dehydrogenase is isolated from *Saccharomyces cerevisiae* and can be found in GenBank with GI number J01314.1.

Other sequences expressing alcohol dehydrogenase or related or homologous genes can be identified in a database such as, for example, GenBank. In one aspect, sequences useful herein include those with the GI numbers listed in Table 3:

TABLE 3

Alcohol Dehydrogenase Genes

| Source Organism | Sequence Description | GI Number |
|---|---|---|
| Saccharomyces cerevisiae | alcohol dehydrogenase II | J01314.1 |
| Saccharomyces cerevisiae | chromosome XIII sequence | CP005453.2 |
| Saccharomyces cerevisiae | chromosome XIII sequence | CP020135.1 |
| Saccharomyces cerevisiae | chromosome XIII sequence | CP005452.2 |
| Saccharomyces cerevisiae | chromosome XIII sequence | CP005450.2 |
| Saccharomyces cerevisiae | chromosome XIII sequence | BK006946.2 |
| Saccharomyces cerevisiae | chromosome XIII sequence | Z49212.1 |
| Saccharomyces cerevisiae | alcohol dehydrogenase II | NM_001182812.1 |
| Saccharomyces cerevisiae | alcohol dehydrogenase II | EF059086.1 |
| Saccharomyces cerevisiae | alcohol dehydrogenase | M38457.1 |
| Saccharomyces cerevisiae | chromosome XIII sequence | CP005464.2 |
| Saccharomyces cerevisiae | chromosome XIII sequence | CP005483.2 |
| Saccharomyces cerevisiae | chromosome XIII sequence | CP005432.2 |
| Saccharomyces cerevisiae | chromosome XIII sequence | CP005482.2 |
| Saccharomyces cerevisiae | chromosome XIII sequence | LN907796.1 |
| Saccharomyces cerevisiae | chromosome XIII sequence | CP005456.1 |
| Saccharomyces cerevisiae | chromosome XIII sequence | CP005455.1 |
| Saccharomyces cerevisiae | chromosome XIII sequence | CP005440.1 |
| Saccharomyces cerevisiae | chromosome XIII sequence | CP020203.1 |
| Saccharomyces cerevisiae | chromosome XIII sequence | CP005403.2 |
| Saccharomyces cerevisiae | chromosome XIII sequence | CP005472.2 |
| Saccharomyces cerevisiae | chromosome XIII sequence | CP005465.2 |
| Saccharomyces cerevisiae | chromosome XIII sequence | CP005405.2 |
| Saccharomyces cerevisiae | chromosome XIII sequence | CP005414.2 |
| Saccharomyces cerevisiae | chromosome XIII sequence | CP005412.2 |
| Saccharomyces cerevisiae | chromosome XIII sequence | CP005451.2 |
| Saccharomyces cerevisiae | chromosome XIII sequence | CP011559.1 |
| Saccharomyces cerevisiae | chromosome XIII sequence | CP005436.1 |
| Saccharomyces cerevisiae | chromosome XIII sequence | CP005426.1 |
| Saccharomyces cerevisiae | chromosome XIII sequence | CP005406.1 |
| Saccharomyces cerevisiae | alcohol dehydrogenase II | JX901290.1 |
| Saccharomyces cerevisiae | chromosome XIII sequence | CP020169.1 |
| Saccharomyces cerevisiae | chromosome XIII sequence | CP005449.2 |
| Saccharomyces cerevisiae | chromosome XIII sequence | CP005429.2 |
| Saccharomyces cerevisiae | chromosome XIII sequence | CP005419.2 |
| Saccharomyces cerevisiae | chromosome XIII sequence | CP005409.2 |
| Saccharomyces cerevisiae | chromosome XIII sequence | CP005428.2 |
| Saccharomyces cerevisiae | chromosome XIII sequence | CP005418.2 |
| Saccharomyces cerevisiae | chromosome XIII sequence | CP005408.2 |
| Saccharomyces cerevisiae | chromosome XIII sequence | CP005477.2 |
| Saccharomyces cerevisiae | chromosome XIII sequence | CP005417.2 |
| Saccharomyces cerevisiae | chromosome XIII sequence | CP005425.2 |
| Saccharomyces cerevisiae | chromosome XIII sequence | CP008265.1 |
| Saccharomyces cerevisiae | chromosome XIII sequence | CP008367.1 |
| Saccharomyces cerevisiae | chromosome XIII sequence | CP008554.1 |
| Saccharomyces cerevisiae | chromosome XIII sequence | CP008537.1 |
| Saccharomyces cerevisiae | chromosome XIII sequence | CP008520.1 |
| Saccharomyces cerevisiae | chromosome XIII sequence | CP008129.1 |
| Saccharomyces cerevisiae | chromosome XIII sequence | CP007993.1 |
| Saccharomyces cerevisiae | chromosome XIII sequence | CP005444.2 |
| Saccharomyces cerevisiae | chromosome XIII sequence | CP005434.2 |
| Saccharomyces cerevisiae | chromosome XIII sequence | CP005424.2 |
| Saccharomyces cerevisiae | chromosome XIII sequence | CP005404.2 |
| Saccharomyces cerevisiae | chromosome XIII sequence | CP005423.2 |
| Saccharomyces cerevisiae | chromosome XIII sequence | CP005422.2 |
| Saccharomyces cerevisiae | chromosome XIII sequence | CP005402.2 |

TABLE 3-continued

Alcohol Dehydrogenase Genes

| Source Organism | Sequence Description | GI Number |
|---|---|---|
| Saccharomyces cerevisiae | chromosome XIII sequence | CP005421.2 |
| Saccharomyces cerevisiae | chromosome XIII sequence | CP005411.2 |
| Saccharomyces cerevisiae | chromosome XIII sequence | CP005420.2 |
| Saccharomyces cerevisiae | chromosome XIII sequence | CP005427.1 |
| Saccharomyces cerevisiae | chromosome XIII sequence | CP005416.1 |
| Saccharomyces cerevisiae | chromosome XIII sequence | CP008010.1 |
| Saccharomyces cerevisiae | glucose-repressible alcohol dehydrogenase II | KJ137141.1 |
| Saccharomyces cerevisiae | chromosome XIII sequence | CP005475.2 |
| Saccharomyces cerevisiae | chromosome XIII sequence | CP008401.1 |
| Saccharomyces cerevisiae | chromosome XIII sequence | CP008503.1 |
| Saccharomyces cerevisiae | chromosome XIII sequence | CP005398.2 |
| Saccharomyces cerevisiae | chromosome XIII sequence | CP005478.2 |
| Saccharomyces cerevisiae | chromosome XIII sequence | CP005437.2 |
| Saccharomyces cerevisiae | chromosome XIII sequence | CP005407.2 |
| Saccharomyces cerevisiae | chromosome XIII sequence | CP005454.2 |
| Saccharomyces cerevisiae | chromosome XIII sequence | CP005462.2 |
| Saccharomyces cerevisiae | chromosome XIII sequence | CP005461.2 |
| Saccharomyces cerevisiae | chromosome XIII sequence | CP005401.2 |
| Saccharomyces cerevisiae | chromosome XIII sequence | CP005396.1 |
| Saccharomyces cerevisiae | chromosome XIII sequence | CP005479.2 |
| Saccharomyces cerevisiae | chromosome XIII sequence | CP005469.2 |
| Saccharomyces cerevisiae | chromosome XIII sequence | CP005399.2 |
| Saccharomyces cerevisiae | chromosome XIII sequence | CP005397.2 |
| Saccharomyces cerevisiae | chromosome XIII sequence | CP005415.2 |
| Saccharomyces cerevisiae | chromosome XIII sequence | CP005395.2 |
| Saccharomyces cerevisiae | chromosome XIII sequence | CP008248.1 |
| Saccharomyces cerevisiae | chromosome XIII sequence | CP008333.1 |
| Saccharomyces cerevisiae | chromosome XIII sequence | CP008316.1 |
| Saccharomyces cerevisiae | chromosome XIII sequence | CP008299.1 |
| Saccharomyces cerevisiae | chromosome XIII sequence | CP008282.1 |
| Saccharomyces cerevisiae | chromosome XIII sequence | CP008231.1 |
| Saccharomyces cerevisiae | chromosome XIII sequence | CP008418.1 |
| Saccharomyces cerevisiae | chromosome XIII sequence | CP008384.1 |
| Saccharomyces cerevisiae | chromosome XIII sequence | CP008350.1 |
| Saccharomyces cerevisiae | chromosome XIII sequence | CP008486.1 |
| Saccharomyces cerevisiae | chromosome XIII sequence | CP008469.1 |
| Saccharomyces cerevisiae | chromosome XIII sequence | CP008435.1 |
| Saccharomyces cerevisiae | chromosome XIII sequence | CP008588.1 |
| Saccharomyces cerevisiae | chromosome XIII sequence | CP008571.1 |
| Saccharomyces cerevisiae | chromosome XIII sequence | CP008656.1 |
| Saccharomyces cerevisiae | chromosome XIII sequence | CP008639.1 |
| Saccharomyces cerevisiae | chromosome XIII sequence | CP008605.1 |
| Saccharomyces cerevisiae | chromosome XIII sequence | CP008214.1 |
| Saccharomyces cerevisiae | chromosome XIII sequence | CP008197.1 |

A lipase is an esterase that catalyzes the hydrolysis of fats, oils, and lipids. In one aspect, the gene that expresses lipase is isolated from a bacterium. In a further aspect, the bacterium is a *Micrococcus* species, a *Pseudomonas* species, a *Moraxella* species, or an *Acinetobacter* species. In a further aspect, the gene that expresses lipase has SEQ ID NO. 6 or at least 70% homology thereof, at least 75% homology thereof, at least 80% homology thereof, at least 85% homology thereof, at least 90% homology thereof, or at least 95% homology thereof. In a further aspect, the cellulose synthase is able to use mannose as a substrate instead of or in addition to glucose. In one aspect, the gene that expresses lipase can be positioned anywhere in the DNA construct disclosed herein. In one aspect, the gene that expresses lipase is positioned 5' (i.e., prior) to the gene that expresses chitin synthase.

Other sequences expressing lipase or related or homologous genes can be identified in a database such as, for example, GenBank. In one aspect, sequences useful herein include those with the GI numbers listed in Table 4:

TABLE 4

Lipase Genes

| Source Organism | Sequence Description | GI Number |
|---|---|---|
| Micrococcus sp. HL-2003 | lipase gene | AY268069.1 |
| Pseudomonas sp. | esterase gene | M68491.1 |
| Moraxella L1 | lipase 1 | X53053.1 |
| A. calcoaceticus | carboxylesterase and peptidyl prolyl-cis-trans-isomerase | X74839.1 |
| Acinetobacter sp. ADP1 | genomic DNA | CR543861.1 |
| A. calcoaceticus | esterase | X71598.1 |
| Pseudomonas trivialis | genomic DNA | CP011507.1 |
| Pseudomonas azotoformans | genomic DNA | CP019856.1 |
| Pseudomonas extremaustralis | genomic DNA | LT629689.1 |
| Pseudomonas fluorescens | genomic DNA | CP005975.1 |
| Pseudomonas fluorescens | genomic DNA | CP010896.1 |
| Pseudomonas fluorescens | genomic DNA | AF228666.1 |
| Pseudomonas simiae | genomic DNA | CP007637.1 |
| Pseudomonas fitioresens | genomic DNA | AM181176.4 |
| Pseudomonas Antarctica | genomic DNA | CP015600.1 |
| Pseudomonas fluorescens | genomic DNA | CP015639.1 |
| Pseudomonas fluorescens | genomic DNA | LT907842.1 |
| Pseudomonas sp. NS1 | genomic DNA | CP022960.1 |
| Pseudomonas poae | genomic DNA | LT629706.1 |
| Pseudomonas poae | genomic DNA | CP004045.1 |
| Pseudomonas rhodesiae | genomic DNA | LT629801.1 |
| Pseudomonas trivialis | genomic DNA | LT629760.1 |
| Pseudomonas azotoformans | genomic DNA | LT629702.1 |
| Pseudomonas Antarctica | genomic DNA | LT629704.1 |
| Pseudomonas fluorescens | genomic DNA | CP012400.1 |
| Pseudomonas azotoformans | genomic DNA | CP014546.1 |
| Pseudomonas yamanorum | genomic DNA | LT629793.1 |
| Pseudomonas prosekii | genomic DNA | LT629762.1 |
| Pseudomonas koreensis | genomic DNA | CP014947.1 |
| Pseudomonas libanensis | genomic DNA | LT629699.1 |
| Pseudomonas sp. GR 6-02 | genomic DNA | CP011567.1 |
| Pseudomonas fluorescens | genomic DNA | CP014868.1 |
| Pseudomonas fluorescens | genomic DNA | CP011117.1 |
| Pseudomonas fluorescens | genomic DNA | S69066.1 |
| Pseudomonas cedrina | genomic DNA | LT629753.1 |
| Pseudomonas sp. bs2935 | genomic DNA | LT629744.1 |
| Pseudomonas fluorescens | genomic DNA | CP017296.1 |
| Pseudomonas sp. WCS374 | genomic DNA | CP007638.1 |
| Pseudomonas fluorescens | genomic DNA | CP003041.1 |
| Pseudomonas corrugate | genomic DNA | LT629798.1 |
| Pseudomonas corrugate | genomic DNA | CP014262.1 |
| Pseudomonas mediterranea | genomic DNA | LT629790.1 |
| Pseudomonas tolaasii | genomic DNA | CP020369.1 |
| Pseudomonas fluorescens | genomic DNA | CP015638.1 |
| Pseudomonas fluorescens | genomic DNA | CP015637.1 |
| Pseudomonas sp. TKP | genomic DNA | CP006852.1 |
| Synthetic construct | carboxylesterase | HM212419.1 |
| Synthetic construct | carboxylesterase | FJ213454.1 |
| Pseudomonas sp. FDAARGOS 380 | genomic DNA | CP023969.1 |
| Pseudomonas synxantha | genomic DNA | LT629786.1 |
| Pseudomonas orientalis | genomic DNA | LT629782.1 |
| Pseudomonas sp. URMO17WK12: I11 | genomic DNA | LN854573.1 |

In another aspect, said construct further includes (d) a promoter, (e) a terminator or stop sequence, (f) a gene that confers resistance to an antibiotic (a "selective marker"), (g) a reporter protein, or a combination thereof.

In another aspect, the DNA construct has the following genetic components: (1) one or more promoters, (2) a gene that expresses zinc-related protein, (3) a gene that expresses alkaline phosphatase, (4) a gene that expresses alcohol dehydrogenase, and (5) one or more terminators or stop sequences.

In an alternative aspect, the DNA construct has the following genetic components: (1) one or more promoters, (2) a gene that expresses zinc-related protein, (3) a gene that expresses lipase, (4) a gene that expresses alkaline phosphatase, (5) a gene that expresses alcohol dehydrogenase, and (6) one or more terminators or stop sequences.

In one aspect, the construct includes a regulatory sequence. In a further aspect, the regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, an iron promoter, and GAL1 promoter. In one aspect, the promoter is the native GAL1 promoter found in the plasmid pYES2. Variants of these promoters are also contemplated. The skilled artisan will be able to use site-directed mutagenesis and/or other mutagenesis techniques to modify the promoters to promote more efficient function. The promoter may be positioned, for example, at about 10-100 nucleotides from a ribosomal binding site. In another aspect, the promoter is positioned before the gene that expresses zinc-related protein, the gene that expresses alkaline phosphatase, the gene that expresses alcohol dehydrogenase, or any combination thereof.

In one aspect, the promoter is a GAL1 promoter. In another aspect, the GAL1 promoter is native to the plasmid used to create the vector. In another aspect, a GAL1 promoter is positioned before the gene that expresses zinc-related protein, the gene that expresses alkaline phosphatase, and the gene that expresses alcohol dehydrogenase. In another aspect, the promoter is a GAL1 promoter obtained from or native to the pYES2 plasmid.

In another aspect, the regulatory sequence is a terminator or stop sequence. As used herein, a "terminator" is a sequence of DNA that marks the end of a gene or operon to be transcribed. In a further aspect, the terminator is an intrinsic terminator or a Rho-dependent transcription terminator. As used herein, an intrinsic terminator is a sequence wherein a hairpin structure can form in the nascent transcript that disrupts the mRNA/DNA/RNA polymerase complex. As used herein, a Rho-dependent transcription terminator requires a Rho factor protein complex to disrupt the mRNA/DNA/RNA polymerase complex. In one aspect, the terminator is a T7 terminator. In an alternative aspect, the terminator is a CYC1 terminator obtained from or native to the pYES2 plasmid.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, XbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g., amount of DNA needed, precise volumes of reagents, purification techniques, as well as information about salt concentration, pH, optimum temperature, incubation time, and the like) are provided by enzyme manufacturers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', usually starting just after a promoter, the order and direction of elements inserted into a plasmid can be especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleotide fragments into the plasmid.

In one aspect, different genes can be ligated into a plasmid in one pot. In this aspect, the genes will first be digested with restriction enzymes. In certain aspects, the digestion of genes with restriction enzymes provides multiple pairs of matching 5' and 3' overhangs that will spontaneously assemble the genes in the desired order. In another aspect, the genes and components to be incorporated into a plasmid can be assembled into a single insert sequence prior to insertion into the plasmid. In a further aspect, a DNA ligase enzyme can be used to assist in the ligation process.

In another aspect, the ligation mix may be incubated in an electromagnetic chamber. In one aspect, this incubation lasts for about 1 minute, about 2 minutes, about 5 minutes, about 10 minutes, about 15 minutes, about 20 minutes, about 30 minutes, or about 1 hour.

The DNA construct described herein can be part of a vector. In general, plasmid vectors containing replicon and control sequences that are derived from species compatible with the host cell are used in connection with the hosts. The vector ordinarily carries a replication site as well as marking sequences that are capable of performing phenotypic selection in transformed cells. Plasmid vectors are well known and are commercially available. Such vectors include, but are not limited to, pWLneo, pSV2cat, pOG44, pXT1, pSG, pSVK3, pBSK, pBR322, pYES, pYES2, pBSKII, pUC, and pUC19 vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the skilled artisan to select host cells that have been successfully transfected with the plasmids (for example, by growing the host cells in a medium containing the antibiotic.

In another aspect, the DNA construct includes a terminator. In a further aspect, the terminator is native to the vector in which the DNA construct is incorporated. In an alternative aspect, a terminator is positioned after each gene of interest, in the 5' to 3' direction.

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not successfully been transformed cannot survive in the presence of the antibiotic; only cells containing the vector that confers antibiotic resistance can survive. Optimally, only cells containing the vector to be expressed will be cultured, as this will result in the highest production efficiency of the desired gene products (e.g., proteins). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolones, rifampin, rifampicin, sulfonamides, cephalothin, erythromycin, streptomycin, gentamycin, penicillin, other commonly-used antibiotics, or a combination thereof.

In certain aspects, the DNA construct can include a gene that expresses a reporter protein. The selection of the reporter protein can vary. For example, the reporter protein can be a yellow fluorescent protein, a red fluorescent protein, a green fluorescent protein, or a cyan fluorescent protein. In one aspect, the reporter protein is a yellow fluorescent protein and the gene that expresses the reporter protein has SEQ ID NO. 4 or at least 70% homology thereto. The amount of fluorescence that is produced by the biological device can be correlated to the amount of DNA incorporated into the microbial host cells. The fluorescence produced by the device can be detected and quantified using techniques known in the art. For example, spectrofluorometers are typically used to measure fluorescence. The Examples provide exemplary procedures for measuring the amount of fluorescence as a result of the expression of DNA.

Figure 1B:
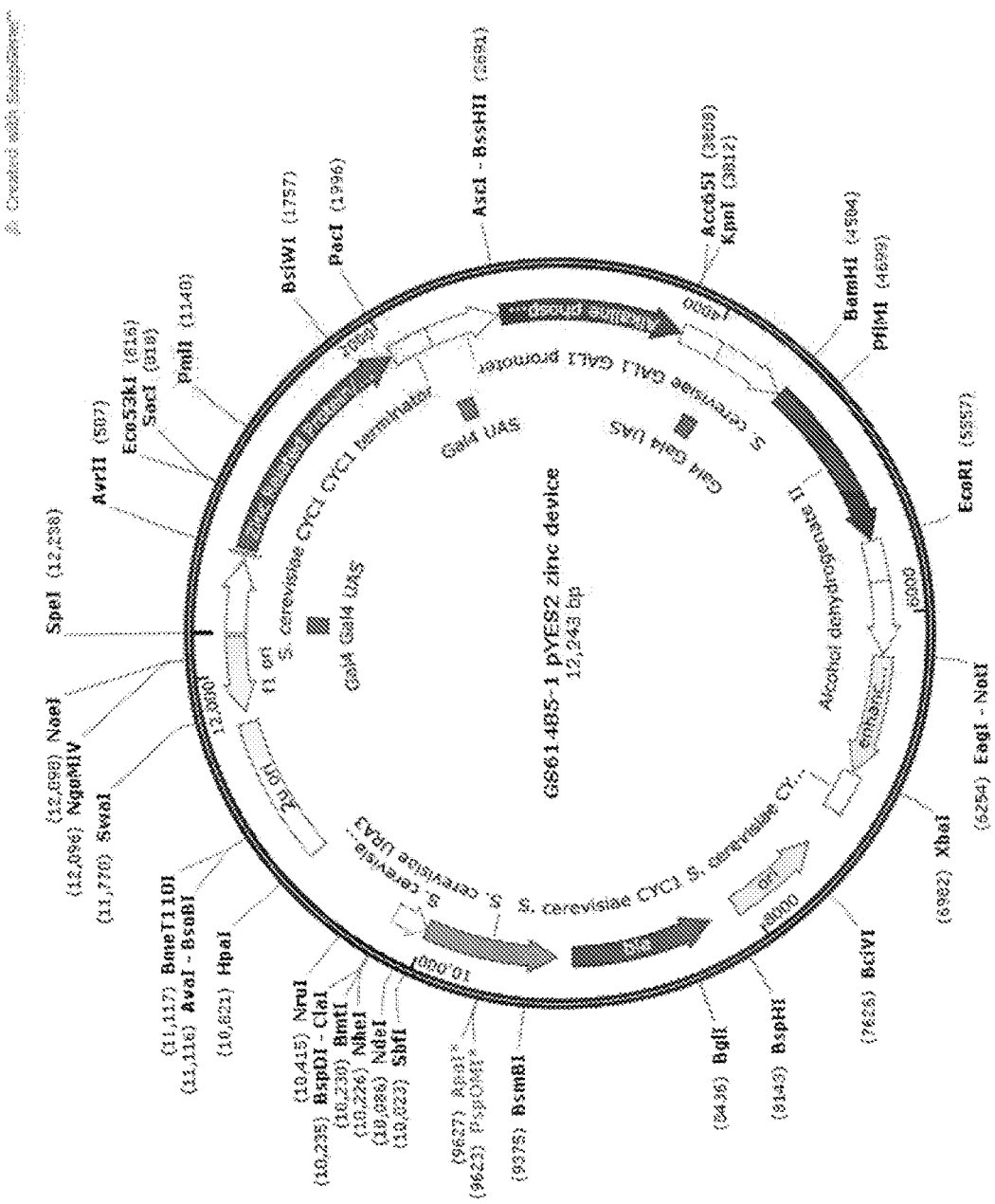

FIGS. 1A and 1B provide non-limiting example of a DNA construct described herein. In one aspect, the construct is a pYES2 plasmid having from 5' to 3' the following genetic components in the following order: (a) a gene that expresses a zinc-related protein, (b) a gene that expresses an alkaline phosphatase, and (c) a gene that expresses an alcohol dehydrogenase. In another aspect, the construct is a pYES2 plasmid having from 5' to 3' the following genetic components in the following order: (a) a GAL1 promoter, (b) a gene that expresses zinc-related protein, (c) a CYC1 terminator, (d) a GAL1 promoter, (e) a gene that expresses alkaline phosphatase, (f) a CYC1 terminator, (g) a GAL1 promoter, (h) a gene that expresses alcohol dehydrogenase, and (i) a CYC1 terminator.

Figure 2A:
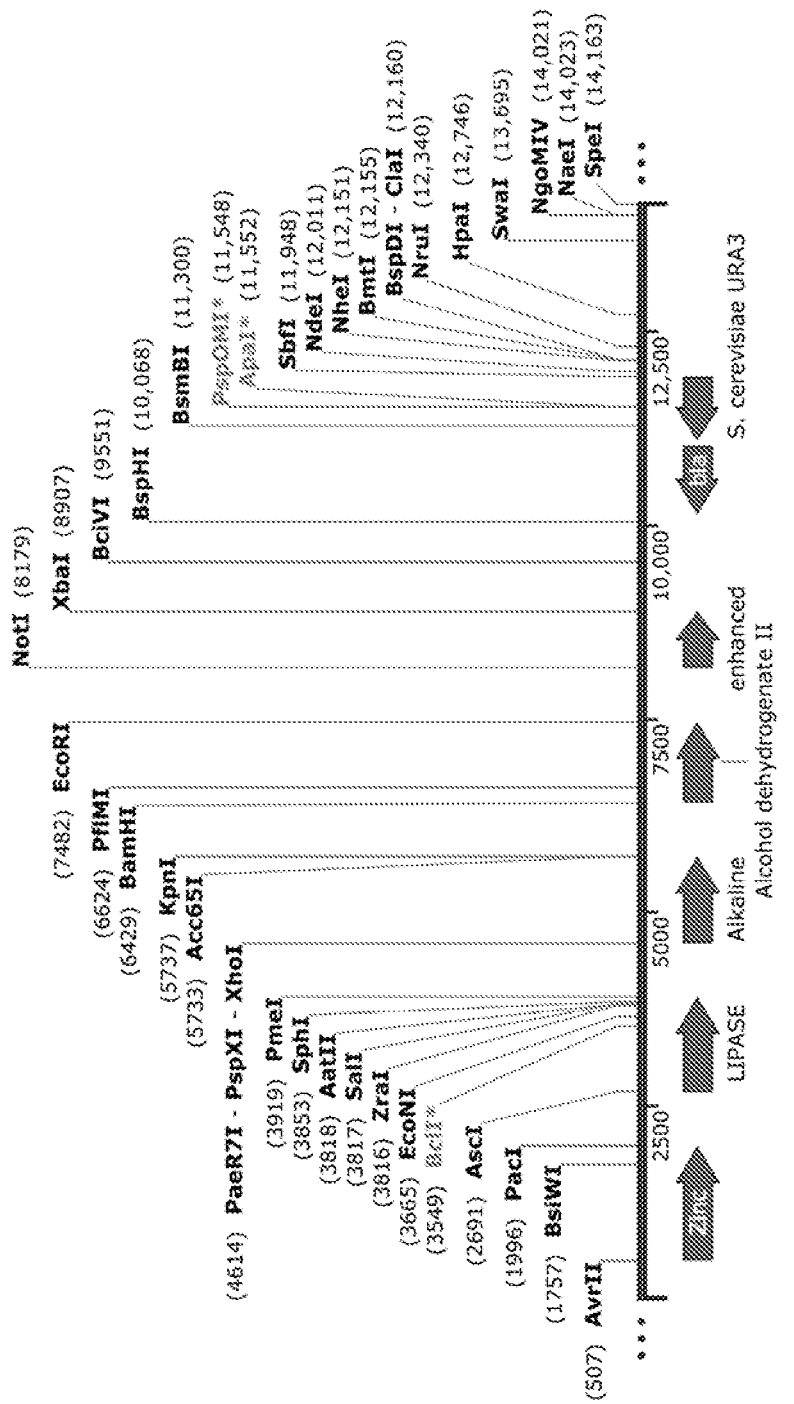
FIGS. 2A and 2B show, respectively, a linear and circular schematic of a constructed pYES2 plasmid showing the direction, placement, and size of genetic parts used of an exemplary DNA device described herein.
Figure 2B:
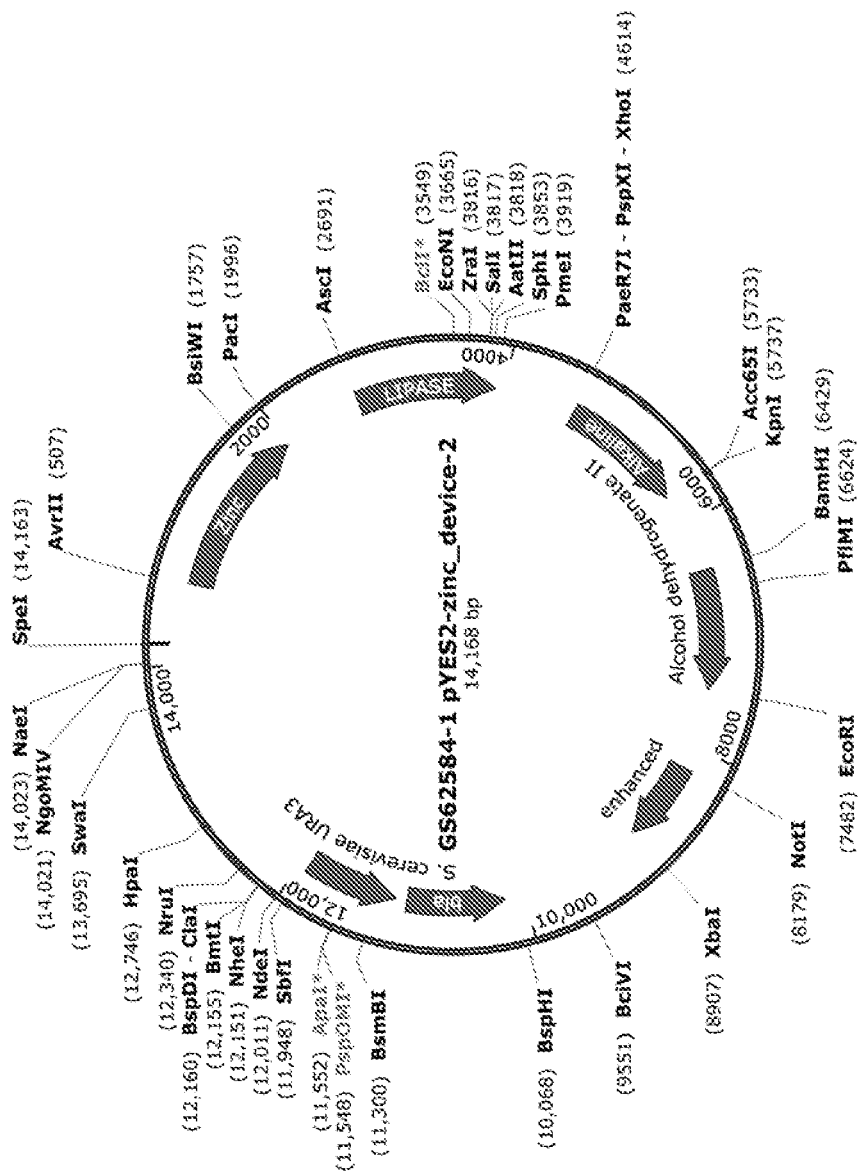

FIGS. 2A and 2B provide an additional non-limiting example of a DNA construct described herein. In one aspect, the construct is a pYES2 plasmid having from 5' to 3' the following genetic components in the following order: (a) a gene that expresses a zinc-related protein, (b) a gene that expresses a lipase, (c) a gene that expresses an alkaline phosphatase, and (d) a gene that expresses an alcohol dehydrogenase. In another aspect, the construct is a pYES2 plasmid having from 5' to 3' the following genetic components in the following order: (a) a gene that expresses zinc-related protein, (b) a CYC1 terminator, (c) a GAL1 promoter, (d) a gene that expresses lipase, (e) CYC1 terminator, (f) a GAL1 promoter, (g) a gene that expresses alkaline phosphatase, (h) a CYC1 terminator, (i) a GAL1 promoter, (j) a gene that expresses alcohol dehydrogenase, and (k) a CYC1 terminator.

In another aspect, the construct comprises from 5' to 3' the following genetic components in the following order: (a) a gene that expresses zinc related protein having SEQ ID NO. 1 or at least 70% homology thereto; (b) a CYC1 terminator, (c) a GAL1 promoter, (d) a gene that expresses alkaline phosphatase having SEQ ID NO. 2 or at least 70% homology thereto; (e) a CYC1 terminator, (f) a GAL1 promoter, (g) a gene that expresses alcohol dehydrogenase having SEQ ID NO. 3 or at least 70% homology thereto, and (h) a CYC1 terminator.

In a further aspect, the construct comprises from 5' to 3' the following genetic components in the following order: (a) a gene that expresses zinc related protein having SEQ ID NO. 1 or at least 70% homology thereto; (b) a CYC1 terminator, (c) a GAL1 promoter, (d) a gene that expresses lipase having SEQ ID NO. 6 or at least 70% homology thereto, (e) a CYC1 terminator, (f) a GAL1 promoter, (g) a gene that expresses alkaline phosphatase having SEQ ID NO. 2 or at least 70% homology thereto; (h) a CYC1 terminator, (i) a GAL1 promoter, (j) a gene that expresses alcohol dehydrogenase having SEQ ID NO. 3 or at least 70% homology thereto, and (k) a CYC1 terminator.

In another aspect, the construct is a plasmid having from 5' to 3' the following genetic components in the following order: (a) a GAL1 promoter, (b) a gene that expresses a zinc-related protein having SEQ ID NO. 1 or at least 70% homology thereto, (c) a CYC1 terminator, (d) a GAL1 promoter, (e) a gene that expresses an alkaline phosphatase having SEQ ID NO. 2 or at least 70% homology thereto, (f) a CYC1 terminator, (g) a GAL1 promoter, (h) a gene that expresses an alcohol dehydrogenase having SEQ ID NO. 3 or at least 70% homology thereto, and (i) a CYC1 terminator.

In yet another aspect, the construct is a plasmid having from 5' to 3' the following genetic components in the following order: (a) a gene that expresses a zinc-related protein having SEQ ID NO. 1 or at least 70% homology thereto, (b) a CYC1 terminator, (c) a GAL1 promoter, (d) a gene that expresses lipase having SEQ ID NO. 6 or at least 70% homology thereto, (e) a CYC1 terminator, (f) a GAL1 promoter, (g) a gene that expresses an alkaline phosphatase having SEQ ID NO. 2 or at least 70% homology thereto, (h) a CYC1 terminator, (i) a GAL1 promoter, (j) a gene that expresses an alcohol dehydrogenase having SEQ ID NO. 3 or at least 70% homology thereto, and (k) a CYC1 terminator.

In a further aspect, the DNA construct has SEQ ID NO. 5 or at least 70% homology thereto.

In an alternative aspect, the DNA construct has SEQ ID NO. 7 or at least 70% homology thereto.

Exemplary methods for producing the DNA constructs described herein are provided in the Examples. Restriction enzymes and purification techniques known in the art can be used to assemble the DNA constructs. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce oxidized zinc. "Heterologous" genes and proteins are genes and proteins that have been experimentally inserted into a cell that are not normally expressed by that cell. A heterologous gene may be cloned or derived from a different cell type or species than the recipient cell or organism. Heterologous genes may be introduced into cells by transfection or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art. Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed for only a limited period of time).

"Competent cells" refers to microbial cells capable of taking up heterologous DNA. Competent cells can be purchased from a commercial source, or cells can be made competent using procedures known in the art. Exemplary procedures for producing competent cells are provided in the Examples.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell.

A transformed cell includes the primary subject cell and its progeny. The host cells can be naturally-occurring cells or "recombinant" cells. Recombinant cells are distinguishable from naturally-occurring cells in that naturally-occurring cells do not contain heterologous DNA introduced through molecular cloning procedures. In one aspect, the host cell is a prokaryotic cell such as, for example, *Escherichia coli*. In other aspects, the host cell is a eukaryotic cell such as, for example, the yeast *Saccharomyces cerevisiae*. Host cells transformed with the DNA construct described herein are referred to as "biological devices."

The DNA construct is first delivered into the host cell. In one aspect, the host cells are naturally competent (i.e., able to take up exogenous DNA from the surrounding environment). In another aspect, cells must be treated to induce artificial competence. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the membranes of the cells through which the vector containing the DNA construct enters. Another method involves exposing intact yeast cells to alkali cations such as, for example, lithium. In one aspect, this method includes exposing yeast to lithium acetate, polyethylene glycol, and single-stranded DNA such as, for example, salmon sperm DNA. Without wishing to be bound by theory, the single-stranded DNA is thought to bind to the cell wall of the yeast, thereby blocking plasmids from binding. The plasmids are then free to enter the yeast cell. Enzymatic and/or electromagnetic techniques can also be used alone, or in combination with other methods, to transform microbial cells. Exemplary procedures for transforming yeast and bacteria with specific DNA constructs are provided in the Examples. In certain aspects, two or more types of DNA can be incorporated into the host cells. Thus, different metabolites can be produced from the same host cells at enhanced rates.

III. Preparation of Oxidized Zinc

The biological devices described herein are useful in the production of oxidized zinc. The oxidized zinc is any chemical species that includes zinc ions. For example the oxidized zinc can be a $Zn^{+1}$ or $Zn^{+2}$ species. In one aspect, the oxidized zinc can be an inorganic material such as, for example, ZnO. In another aspect, the oxidized zinc can be $Zn^{+2}$ with organic groups or molecules bonded to the zinc ion through covalent bonds, electrostatic bonds, hydrogen bonding, Lewis acid/base interactions, or Vander Waals bonds. The organic groups can be small molecules or macromolecules such as proteins. The biological devices described herein can produce a composition composed of one or more zinc ion species.

Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth-promoting substances. For example, the addition of peptone provides a readily-available source of nitrogen and carbon. Furthermore, the use of different types of media results in different growth rates and different stationary phase densities; stationary phase is where secondary metabolite production occurs most frequently. A rich media results in a short doubling time and higher cell density at stationary phase. Minimal media results in slow growth and low final cell densities. Efficient agitation and aeration increase final cell densities.

In one aspect, host cells may be cultured or fermented by any method known in the art. The skilled practitioner will be able to select a culture medium based on the species and/or strain of host cell selected. In certain aspects, the culture medium will contain a carbon source. A variety of carbon sources are contemplated, including, but not limited to: monosaccharides such as glucose and fructose, disaccharides such as lactose or sucrose, oligosaccharides, polysaccharides such as starch, or mixtures thereof. Unpurified mixtures extracted from feedstocks are also contemplated as carbon sources, as are one-carbon substrates such as carbon dioxide and/or methanol in the cases of compatible organisms. The carbon source utilized is limited only by the particular organism being cultured.

Culturing or fermenting of host cells may be accomplished by any technique known in the art. In one aspect, batch fermentation may be conducted. In batch fermentation, the composition of the culture medium is set at the beginning and the system is closed to future artificial alterations. In some aspects, a limited form of batch fermentation may be carried out wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation may be carried out on any scale and may include methods in which literal "fermentation" is carried out as well as other culture methods that are non-fermentative.

In one aspect, the biological devices described herein are provided with an impure source of zinc or zinc oxide. In a further aspect, the impure source of zinc or zinc oxide can be an ore, a recycled material, an environmental sample such as soil with a high zinc content, zinc metal, a zinc salt, or a combination thereof. In a still further aspect, the source of zinc or zinc oxide can be in solution or suspension in water or another solvent, including acidic or basic solutions, or can be in the form of finely ground particles or in another solid form.

In one aspect, the method involves growing the biological devices described herein for a sufficient time to produce oxidized zinc from the impure source of zinc or zinc oxide. The ordinary artisan will be able to choose a culture medium and optimum culture conditions based on the biological identity of the host cells.

In one aspect, the biological device can be exposed to UV radiation at wavelength of 250 nm, 275 nm, 300 nm, 325 nm, 350 nm, 375 nm, or 400 nm, where any value can be a lower or upper end-point of a range (e.g., 250 nm to 400 nm, 300 nm to 375 nm, etc.). The exposure to UV radiation can be from 0.5 hours to 120 hours.

In certain aspects, after culturing the biological device to produce the oxidized zinc, the host cells of the device can be lysed with one or more enzymes. For example, when the host cells are yeast, the yeast cells can be lysed with lyticase. In one aspect, the lyticase concentration can be 500, 600, 700, 800, 900, or 1000 µL per liter of culture, where any value can be the lower or upper endpoint of a range (e.g. 500 to 900 µL, 600 to 800 µL, etc.).

In addition to enzymes, other components can be used to facilitate lysis of the host cells. In one aspect, chitosan can be used in combination with an enzyme to lyse the host cells. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance metabolite production. In one aspect, the chitosan is from 60% to about 100%, 70% to 90%, 75% to 85%, or is about 80% acetylated. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine unit and/or N-acetylglucosamine units. In another aspect, the chitosan includes 5 to 7 glucosamine units and/or N-acetylglucosamine units. In one aspect, the chitosan can be added until a concentration of 0.0015, 0.0025, 0.0050, 0.0075, 0.01, 0.015, 0.02, 0.03, 0.04, or 0.05% (v/v) is achieved in the culture, where any value can be a lower or an upper end-point of a range (e.g., 0.005 to 0.02%, 0.0075 to 0.015%, etc.). Still further in this aspect, the chitosan is present at a concentration of 0.01%.

In a further aspect, the oxidized zinc can be collected, separated from the microbial cells (lysed or intact), and/or purified through any technique known in the art such as, for example, precipitation, centrifugation, filtration, or the like. The Examples provide an exemplary procedure for producing and purifying the oxidized zinc described herein.

In one aspect, compositions composed of the oxidized zinc with lysed and/or intact host cells can be used herein where it is not necessary to separate the host cells and other components from the oxidized zinc.

IV. Applications of the Oxidized Zinc

In one aspect, the oxidized zinc produced herein can be used in the production of ceramic components, semiconductors, or electrical components such as, for example, solar cells. Further in this aspect, the oxidized zinc produced herein may protect such components against lightning or other voltage surges.

In an alternative aspect, the oxidized zinc produced herein can be used in the production of glasses. In one aspect, the low coefficient of expansion of oxidized zinc can help glass materials resist thermal and/or mechanical shock. In a further aspect, glasses produced with the oxidized zinc described herein have high refractive indices and high thermal conductivity. In a still further aspect, inclusion of the oxidized zinc oxide herein in glass formulations reduces the fusion point of the glasses during melting. In one aspect, oxidized zinc produced herein can impart some or all of these properties to other materials in which the zinc oxide is included such as, for example, plastics, ceramics, glass, cement, rubber, lubricants, paints, ointments, adhesives, sealants, concrete, pigments, foods, batteries, fire retardants, and the like.

In a still further aspect, the oxidized zinc produced herein can be used in cosmetic, pharmaceutical, or medical applications. In one aspect, the oxidized zinc has astringent properties and can be used in skincare products. In another aspect, the oxidized zinc can be used in sunscreen creams. In still another aspect, the oxidized zinc can be used as a dietary supplement for humans or a micronutrient sample for livestock and/or other animals. In one aspect, the oxidized zinc can be applied to soil in order to increase crop yield. In a still further aspect, the oxidized zinc can be used in wound healing applications such as, for example, bandages, gauze, and other wound dressings, due to its antifungal properties. In yet another aspect, the oxidized zinc can be used in dental cement or can be used as a precursor to produce components of dental cement.

In yet another aspect, the oxidized zinc described herein can be incorporated on the surface of or throughout various materials to impart desired properties. In one aspect, when incorporated into paints, inks, and dyes, the oxidized zinc acts as a white pigment or as a brightener. In another aspect, the oxidized zinc may protect rubber, plastic, or other polymeric products such as, for example, outdoor furniture, from ultraviolet damage or may impart heat resistance to these items. In yet another aspect, the oxidized zinc can act as a reinforcing agent and/or impart abrasion resistance to objects and materials containing or coated with the oxidized zinc. In any of these applications, the oxidized zinc may aid in color retention due to its ultraviolet-absorbing properties. In a further aspect, the oxidized zinc can impart resistance to bacterial and fungal growth, including the growth of mildew and mold, to objects coated with or formulated to contain the oxidized zinc.

In a further aspect, the oxidized zinc can be used as an activator in the curing and/or vulcanization of rubber or latex products, or can improve adhesion in adhesive products. Further in this aspect, the oxidized zinc produced herein can be used with stearic acid in the vulcanization process and can also protect rubber from colonization by fungi. In an alternative aspect, the oxidized zinc can be dissolved in an acid and used for an industrial process. Further in this aspect, the acid can be phosphoric acid and the resulting solution can be used for coating or priming metal. Alternatively in this aspect, the acid can be sulfuric acid and the resulting solution can be used for electroplating.

In one aspect, the oxidized zinc can be used as a precursor compound in the manufacture of another zinc salt such as, for example, zinc gluconate, zinc borate, zinc chloride, zinc dithiophosphate, zinc chromate, zinc diacrylate, or another zinc salt.

In another aspect, the oxidized zinc produced herein may be useful in the production of ceramics. In one aspect, the oxidized zinc can be incorporated into a ceramic glaze or frit. Further in this aspect, the oxidized zinc can affect the melting point and/or optical properties of objects coated with or formed from the oxidized zinc.

In another aspect, the extracts described herein can be applied to any material that may benefit from a reduction in UV radiation. The exact formulation of the extract plus any carriers can be adjusted based on the desired use. In one aspect, the extract is formulated with only non-toxic components if it is to be used on a human or animal or with another microorganism, such as in a fermentation process or on an agricultural product. In another aspect, the extract can be mixed with other substances to provide UV-protective properties to the overall composition. In still another aspect, if coated on the material to be protected, the extract itself can be covered with a further protective coating to project, for example, against mechanical wear and damage.

In the case when the extract is applied to the surface of an article, it can be applied using techniques known in the art such spraying or coating. In other aspects, the extract can be intimately mixed with a substance or material that ultimately produces the article. For example, the extract can be mixed with molten glass so that the extract is dispersed throughout the final glass product.

In one aspect, the extract is formulated or applied in such a manner as to block approximately 50%, 60%, 70%, 80%, 90%, 95%, or 99% of the UV radiation that encounters the extract, where any value can be a lower and upper end-point of a range (e.g., 60% to 95%). In a further aspect, the extract can also be formulated to block these percentages of particular UV wavelengths, or, more generally, to block these percentages of UVA, UVB, or UVC radiation.

The extracts described herein can be used for a variety of purposes. These purposes include, but are not limited to, the following:

1. blocking UV radiation or other types of radiation;
2. protecting human skin against damage and/or skin cancer induced by UV radiation or other types of radiation;
3. protecting against side effects of radiation used in cancer treatments;
4. protecting animals from deleterious effects of UV radiation or other radiation;
5. protecting plastic, fiberglass, glass, rubber, or other solid surfaces from UV radiation or other radiation;
6. providing a UV radiation screen or screen for other types of radiation;
protecting astronauts and/or other persons or organisms as well as equipment during space trips;
8. enhancement of industrial fermentation processes or other processes requiring energy by allowing the use of UV radiation in connection with the process to supply additional energy and thus to increase the ultimate energy-requiring output of the cells without substantially killing the fermenting organism;
9. protection of experimentation, fermentation, biochemical, and/or biological processes under the presence of UV radiation, for example in extraterrestrial conditions such as on the moon or Mars; and 10. protection of agricultural plants, particularly agricultural plants in which the revenue-producing part of the plant is above ground, such as fruits, vine vegetables, beans and peas, and leaf vegetables.

In one particular embodiment, the extracts described herein can be applied to an agricultural plant. In one aspect, the plant can be one that produces fruit or vegetable, such as, for example, a watermelon or a tomato. Further in this aspect, the extract can be applied during at least a part of the plant's growth to increase the amounts of one or more nutrients of the fruit or vegetable, such as a vitamin, mineral, or other recommended dietary component. In one specific aspect, the amount of lycopene can be increased (which may be accompanied by a decrease in carotene or other less-valuable nutrients formed by competing pathways). In another aspect, the amount of a flavor-enhancing component, such as glucose, can be increased. Further in this aspect, an increase in glucose can help protect against water loss.

In one aspect, the extract can be applied for about 25%, 50%, 75%, 90%, 95%, or 99% of the fruit or vegetable's on-plant life, where the on-plant life includes the time span from the formation of a separate body that will constitute the fruit or vegetable (in some aspects, excepting flowers) until the fruit or vegetable is harvested. In one aspect, the extract can be first applied when the fruit or vegetable is sufficiently large to no longer be substantially protected from UV radiation by leaves. In another aspect, the extract can first be applied five days, one week, or two weeks prior to harvest. Further in this aspect, application at this later stage can be particularly useful with fruits or vegetables in which an increase in a nutrient or flavor-enhancing component can be obtained by protecting the fruit or vegetable from UV radiation later in its on-plant life.

In one aspect, the extract can be applied once or multiple times to each fruit or vegetable. In another aspect, it can be applied weekly, or it can be reapplied after the fruit or vegetable is exposed to rain or after a turning process. In another aspect, the agricultural plant can be another food crop that grows above ground and is exposed to natural UV radiation, wherein the agricultural product produced can be a fruit, leaf, seed, flower, grain, nut, stem, vegetable, or mushroom.

In another aspect, it is desirable for agricultural plants that do not produce parts typically consumed by humans to be protected from UV irradiation. In a further aspect, these other agricultural plants can includes sources of fibers such as, for example, cotton and linen (flax), of cork, of wood or lumber, of feedstocks for producing ethanol or biodiesel (including, but not limited to, sugar beet, sugarcane, cassava, sorghum, corn, wheat, oil palm, coconut, rapeseed, peanut, sunflower, soybean, and the like), of animal feedstocks or fodder, or of decorative or horticultural plants.

In one aspect, any part of the plant can be coated, including, but not limited to, the part of the plant that is collected during harvest. In an alternative aspect, the harvested part of the plant is not coated, but another part can be coated with the extracts disclosed herein. In addition to the aspects already described, in one aspect, coating a plant with the extracts described herein can prolong the life of the plant, increase production capacity of a desired product, can increase the growth rate of the plant relative to an untreated plant of the same type, can increase production of a desired metabolite that might otherwise decrease due to UV-induced stress, can increase yield of a crop of such plants, and the like.

In a further aspect, application can be accomplished with a commercial sprayer. In another aspect, application can be only on the upper portions of the fruit or vegetable, which are exposed to substantially greater amounts of UV radiation than the lower portions of the fruit or vegetable.

In another aspect, provided herein is a pharmaceutical composition containing the extracts produced by the biological devices described herein. In one aspect, the pharmaceutical composition can be applied to a subject, wherein the subject is exposed to radiation. In one aspect, the radiation is applied as a strategy to treat cancer. In another aspect, the pharmaceutical composition is used to prevent radiation-induced cellular and DNA damage. In another aspect, dosage ranges of the extract in the pharmaceutical composition can vary from 0.01 g extract/mL of pharmaceutical composition to 1 g extract/mL of pharmaceutical composition, or can be 0.01, 0.02, 0.025, 0.05, 0.075, or 1 g extract/mL of pharmaceutical composition. In an alternative aspect, provided herein is a cosmetic composition containing the extracts produced by the biological devices described herein. Further in this aspect, the cosmetic composition can be a cleanser, lotion, cream, shampoo, hair treatment, makeup, lip treatment, nail treatment, or related composition. In still a further aspect, the compositions containing the extracts can have both pharmaceutical and cosmetic applications. In yet another aspect, the compositions containing the extracts can be used in veterinary medicine.

In one aspect, the oxidized zinc produced herein can be formulated, along with iron (III) oxide, as calamine lotion to relieve itch. In another aspect, the oxidized zinc can be mixed with eugenol and used as a prosthodontic. In another aspect, the oxidized zinc can be added as an ingredient to baby powder, barrier creams, diaper rash treatments, anti-dandruff shampoos, antiseptic ointments, burn treatment creams, hemorrhoid creams, and the like.

In another aspect, the oxidized zinc can be milled or ground into fine particles and incorporated into materials and compositions for its desirable deodorizing or antibacterial properties for use on the body, on surfaces, in healthcare settings, and the like.

The cosmetic compositions can be formulated in any physiologically acceptable medium typically used to formulate topical compositions. The cosmetic compositions can be in any galenic form conventionally used for a topical application such as, for example, in the form of dispersions of aqueous gel or lotion type, emulsions of liquid or semi-liquid consistency of the milk type, obtained by dispersing a fatty phase in an aqueous phase (O/W) or vice versa (W/O), or suspensions or emulsions of soft, semi-solid or solid consistency of the cream or gel type, or alternatively multiple emulsions (W/O/VV or O/W/O), microemulsions, vesicular dispersions of ionic and/or non-ionic type, or wax/aqueous phase dispersions. These compositions are prepared according to the usual methods.

The cosmetic compositions can also contain one or more additives commonly used in the cosmetics field, such as emulsifiers, preservatives, sequestering agents, fragrances, thickeners, oils, waxes or film-forming polymers. In one aspect, in any of the above scenarios, the pharmaceutical, cosmetic, or veterinary composition also includes additional UV-protective compounds or UV-blocking agents such as, for example, zinc oxide, titanium dioxide, carotenoids, oxybenzone, octinoxate, homosalate, octisalate, octocrylene, avobenzone, or a combination thereof.

In one aspect, the composition is a sunscreen. A sunscreen can be formulated with any of the extracts produced herein. In addition to the extract, the sunscreen in certain aspects can be formulated with one or more UV-protective compounds or UV-blocking agents listed above. The sunscreen can be formulated as a paste, lotion, cream, aerosol, or other suitable formulations for topical use. In certain aspects, the sunscreen can be formulated as a transparent composition. In one aspect, when included in a sunscreen, the oxidized zinc produced herein can block both UVA (320-400 nm) and UVB (280-320 nm) rays. In a still further aspect, when incorporated into a sunscreen or skincare or cosmetic product, the oxidized zinc is non-irritating, non-allergenic, and non-comedogenic.

In one aspect, the cosmetic composition can be a film composed of the extracts produced herein that can be directly applied to the skin. For example, the film can be composed of a biocompatible material such as a protein or oligonucleotide, where the extract is coated on one or more surfaces of the film or, in the alternative dispersed throughout the film. For example, the film can be composed of DNA. In this application, the films can be used as a wound covering and provide protection from UV photodamage. The films can also be prepared so that they are optically transparent. Here, it is possible to view the wound without removing the covering and exposing the wound. The films can also include other components useful in cosmetic applications such as, for example, compounds to prevent or reduce wrinkles.

In one aspect, the pharmaceutical, cosmetic, or veterinary compositions described herein are applied to subjects. In one aspect, the subject is a human, another mammal, or a bird. In a further aspect, the mammal is a pet such as a dog or cat or is livestock such as horses, goats, cattle, sheep, and the like. In an alternative aspect, the bird is a pet bird or is poultry such as, for example, a chicken or turkey. In any of these aspects, the compositions can be applied to skin, fur, feathers, wool, hooves, horns, or hair as appropriate and applicable.

In another aspect, provided herein is a paint, dye, stain, or ink containing the UV-protective and/or UV-resistant extract disclosed herein. In one aspect, there are several benefits to having a paint that is resistant to UV irradiation. In a further aspect, imparting UV resistance to a paint slows or stops photodegradation, bleaching, or color fading. In another aspect, a paint with UV resistance prevents chemical modification of exposed paint surfaces. Further in this aspect, chemical modification of exposed paint surfaces includes change in finish, structural changes in binders, flaking, chipping, and the like. In one aspect, the paint provided herein resists these changes.

In still another aspect, provided herein is an article coated with the extracts disclosed herein. In one aspect, the article is made of glass, plastic, metal, wood, fabric, or any combination thereof. In one aspect, the article is a construction material such as, for example, steel, concrete or cement, brick, wood, window or door glass, fiberglass, siding, wallboard, a flooring material, masonry, mortar, grout, stone, artificial stone, stucco, shingles, roofing materials, and the like. In an alternative aspect, the material is an aeronautical or aerospace material such as, for example, the metal or metal alloy body of an aircraft or spacecraft, paint on the body of an aircraft or spacecraft, glass windows on an aircraft or spacecraft, carbon fiber composite, titanium or aluminum, a ceramic heat absorbing tile, and the like. In still another aspect, the article is a fabric article such as, for example, clothing, drapes, outdoor upholstery, a tent or outdoor pavilion, a flag or banner, or the like. In another aspect, the extract can be applied to the article to fine artwork, solid pieces (e.g., vases), and historical documents in order to preserve them. In another aspect, the extract can be applied to outdoor signs such as highway billboards and advertising.

In other aspects, the extract can be incorporated within or throughout the article. In one aspect, the extract can be mixed with molten glass to produce glass article that are UV resistant such as, for example, sunglasses, car windshields, window glass, and eyeglasses. In another aspect, the glass article can be a bottle for storing a beverage or food container in order to increase the shelf-life of the beverage or food. It is contemplated that the extract can be applied externally to the glass articles as well.

In another aspect, the extract can be mixed with fiberglass or plastics in order to reduce negative effects to aircraft, watercraft, boats, jet skis, decking, house siding, motor homes, sunroofs, and moon roofs that are constantly exposed to UV radiation. It is contemplated that the extract can be applied externally to the fiberglass or plastic articles as well.

In another aspect, the extract can be mixed with rubber, silicon, or latex used to make a variety of articles such as water hoses, tires, and the like. It is contemplated that the extract can be applied externally to the rubber, silicone, or latex articles as well.

In another aspect, the extract can be mixed with foams used to make a variety of articles such as automotive dashboard padding, seat cushions, and the like. It is contemplated that the extract can be applied externally to the foam articles as well.

In another aspect, the extracts described herein can be incorporated into an optical film. In one aspect, the extract is applied to at least one surface of the film. In another aspect, the extract can be dispersed throughout the film. The film can be transparent, translucent or opaque. The film can be composed of, but not limited to, polyolefin resin, such as polyethylene (PE) or polypropylene (PP); polyester resin, such as polyethylene terephthalate (PET); polyacrylate resin, such as polymethyl (meth)acrylate (PMMA); polycarbonate resin; polyurethane resin or a mixture thereof. The optical film can be applied to any substrate where it is desirable to reduce or prevent UV exposure or damage. For example, the optical film can be applied to windows to reduce or prevent UV radiation from entering a structure (e.g., building, vehicle, etc.).

In another aspect, provided herein is a method of reducing or preventing the exposure of an item to UV radiation by applying the extracts described herein to the item or incorporating the extract within/throughout the article. Further in this aspect, "reducing" is defined relative to an untreated control. That is, if two like items are exposed to equal amounts of UV radiation for an equal amount of time, but one has been treated with the UV-resistant extracts and the other has not, and some objective response is measured (e.g., color fading, structural degradation, plant size or yield, etc.), the treated item will appear to have been exposed to a lower amount of UV (for example, the color of the treated item will have faded less and will remain closer to the original, or a treated plant will appear larger and more vigorous and will have a greater yield, etc.). In some aspects, treatment with the extracts disclosed herein will prevent UV exposure from occurring. As used herein, "prevent" indicates that a treated item will not be affected, changed, or altered by UV exposure.

In one aspect, the extract blocks from 50% to 100% of UV radiation from contacting the item. Further in this aspect, the extract blocks at least 50%, 55%, 60%, 65%, 70%, 75%, 80%, 85%, 90%, 95%, 99%, or 100% of UV radiation from contacting the item. In another aspect, the extract blocks from 50% to 100% of longwave UV radiation from contacting the item. Further in this aspect, the extract blocks at least 50%, 55%, 60%, 65%, 70%, 75%, 80%, 85%, 90%, 95%, 99%, or 100% of longwave UV radiation from contacting the item. In one aspect, the extract blocks from 50% to 100% of shortwave UV radiation from contacting the item. Further in this aspect, the extract blocks at least 50%, 55%, 60%, 65%, 70%, 75%, 80%, 85%, 90%, 95%, 99%, or 100% of shortwave UV radiation from contacting the item.

Depending upon the application, the extract can prevent or reduce damage cause by UV radiation from limited to extended periods of time. By varying the amount of extract that is applied as well as the number of times the extract is applied, the degree of UV protection can be varied. In certain aspects, it may be desirable for the article to be protected from UV damage for a short period of time then subsequently biodegrade.

In another aspect, the extracts produced herein can be used to reduce or prevent the growth of barnacles on boats and other water vehicles. In one aspect, the extract can be admixed with a paint that is typically applied to water vehicles, where the paint also includes chitosan. In one aspect, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. In one aspect, chitosan isolated from the shells of crab, shrimp, lobster, and/or krill is useful herein. The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units.

In another aspect, the extracts produced herein can be formulated as a pharmaceutical composition for increasing the zinc levels in a subject. Maintaining zinc levels in a subject is desirable for promoting good health. In certain diseases, zinc levels are decreased significantly. For example, in certain cancers such as, for example, hepatocellular carcinoma (HCC), the patient has a significant decrease in zinc levels. The extracts described herein can be formulated such that when administered to the subject increase zinc levels to a normal and healthy value. The extracts can be administered to a subject that is undergoing chemotherapy.

The extracts described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. For example, the pH of the composition is from about 5 to about 6, which is suitable for topical applications. Additionally, the pharmaceutical compositions can include carriers, thickeners, diluents, preservatives, surface active agents and the like in addition to the compounds described herein.

In one aspect, the extract can also be injected parenterally either intravenously, subcutaneously, intramuscularly, intradermally, intranasally, or intrathecally. For example, the extract can be administered rectally by an enema, suppository, catheter, needleless syringe, or bulb syringe. In other aspects, the extract can be formulated for oral administration in the form of a beverage, lozenge, tablet, capsule, or any other suitable medium for oral administration.

In one aspect, the oxidized zinc produced herein can be formulated as nanoparticles. In this aspect, oxidized zinc does not appear white against the skin when used in cosmetic applications. In a further aspect, oxidized zinc nanoparticles may help contribute to the antibiotic activity of ciprofloxacin and similar drugs by interfering with the action of microbial proteins. In a still further aspect, oxidized zinc nanoparticles may be more difficult for bacteria to develop resistance to than other antimicrobial ingredients.

In another aspect, the oxidized zinc produced herein can be a component of cigarette filters, or can be added to foods, beverages, functional foods, vitamins, and supplements as a source of dietary zinc.

In one aspect, the oxidized zinc produced herein can be incorporated into pigments including oil paints and mineral makeup, or can be used as a paper coating. In still another aspect, the oxidized zinc can be used as an anticorrosive coating for metals such as, for example, galvanized iron, or in nuclear reactors. In one aspect, paints and coatings that include the oxidized zinc produced herein can be flexible and long-lasting in the environment. In still another aspect, the oxidized zinc produced herein can reduce photo-yellowing of plastics (such as poly carbonate) and other materials.

In still another aspect, the oxidized zinc produced herein can be used in a semiconductor such as one that is n-type doped with aluminum or gallium. In an alternative aspect, the oxidized zinc produced herein can be used in electrical elements such as laser diodes, LEDs, field emitters, electrodes (when doped with aluminum), liquid crystal displays, transparent thin-film transistors, ferromagnets (in combination with Mn, Fe, Co, V, or another magnetic ion), piezoelectric devices, anodes in lithium ion batteries, and/or sensors for electric current or hydrogen gas.

In an alternative aspect, the oxidized zinc can be used in an industrial process such as pretreatment of natural gas to remove hydrogen sulfide.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperatures, etc.) but some errors and deviations should be accounted for. Unless indicated otherwise, parts are parts by weight, temperature is in ° C. or is at ambient temperature, and pressure is at or near atmospheric. Numerous variations and combinations of reaction conditions (e.g., component concentrations, desired solvents, solvent mixtures, temperatures, pressures, and other reaction ranges and conditions can be used to optimize the product purity and yield obtained from the desired process. Only reasonable and routine experimentation will be required to optimize such processes and conditions.

Example 1: Preparation of DNA Construct for Production of Oxidized Zinc

The DNA construct was composed of genetic components described herein and assembled in plasmid vectors (e.g., pYES2). Sequences of genes and/or proteins with desired properties were identified in GenBank; these included a zinc-related protein gene, an alkaline phosphatase, and an alcohol dehydrogenase gene. Other genetic parts were also obtained for inclusion in the DNA constructs including, for example, promoter genes (e.g., GAL1 promoter), reporter genes (e.g., yellow fluorescent reporter protein), and terminator sequences (e.g., CYC1 terminator). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. The plasmid was then digested with restriction enzymes according to directions and using reagents provided by the enzyme's supplier (Promega). The complete insert, containing restriction sites on each end, was then ligated into the plasmid. Successful construction of the insert and ligation of the insert into the plasmid were confirmed by gel electrophoresis.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis, 1989, *Molecular Cloning: A Laboratory Manual*, $2^{nd}$ ed., Vol. 1, Cold Spring Harbor Laboratory Press: Cold Spring Harbor, N.Y.). Digestion and ligation were used to ensure assembly of DNA synthesized parts using restriction enzymes and reagents (PCR master mix of restriction enzymes: XhoI, KpnI, XbaI, EcoRI, BamHI, and HindIII, with alkaline phosphatase and quick ligation kit, all from Promega). DNA was quantified using a NanoVue spectrophotometer (GE Life Sciences) and a standard UV/Visible spectrophotometer using the ratio of absorbances at 260 nm versus 280 nm. In order to verify final ligations, DNA was visualized and purified via electrophoresis using a Thermo EC-150 power supply.

The DNA construct was made with gene parts fundamental for expression of sequences such as, for example, ribosomal binding sites, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. The DNA constructs in FIG. 1 was assembled using the techniques above.

After the vector comprising the DNA construct has been produced, the resulting vector can be incorporated into the host cells using the methods known in the art (e.g., Gietz, R. D. and R. H. Schiestl, 2007, *Nature Protocols*, "Quick and easy yeast transformation using the LiAc/SS carrier DNA/PEG method," Vol. 2, 35-37, doi:10.1038/nprot.2007.14). In some instances, competent yeast cells (strain INVSc1) were purchased from Invitrogen, Inc. and transformed with a kit from Sigma Aldrich, Inc.

From a plate of transformed cells (SC dropout plate deficient in uracil), four clones were selected and processed for full-length DNA sequencing. A clone with 100% DNA sequence accuracy was selected for further processing and used to obtain a high concentration of the plasmid construct at a mid-scale plasmid purification level.

Example 2: Growth and Induction of the Yeast-Zinc Device

A small sample of the biological devices described herein (*S. cerevisiae* transformed with the constructs in FIG. 1A-B) was mixed with 3-5 mL of yeast malt (YM) for growing at 30° C., overnight. Growth and production of the metabolites were induced as follows. 1 mL of the devices grown overnight were taken into 1 L of yeast malt medium containing 2% raffinose and incubated at 30° C. for 2-4 hours until the growth of the culture reached 0.6-0.6 optical density. Galactose sugar (1%) was then added to the above culture, which was then incubated for at least 48-72 hours at 30° C.

Example 3: Extraction of Anti UV Metabolites and Compounds from the Yeast-Zinc Device After 48 hours, the culture from Example 2 was treated with lyticase (240 µL/L) for 24 hours. The culture was then centrifuged at 9000 rpm for 15 minutes to obtain a pellet. The pellet was mixed with sterilized distilled water at a ratio of 1 g pellet/100 mL water. This mixture was subjected to a protocol of sonication at alternating periods of 30 seconds on, 15 seconds off, for 2 minutes at 60% of wavelength amplitude (QSONICA Sonicator, Newtown, Conn.); this procedure was repeated twice. The supernatant from the above sonication was centrifuged to discard dead cells and debris, then filtered through a 0.45 µm pore size filter. The filtrate was then used for further anti-UV tests.

Example 4: Electrochemical Analysis

Figure 7A:
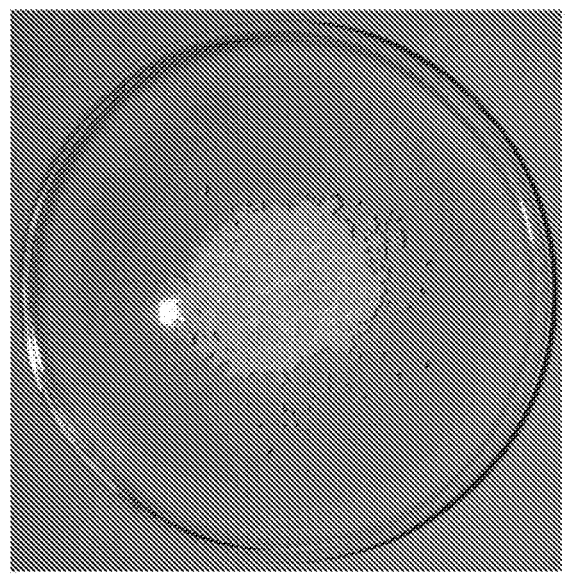
FIGS. 7A-D show the process and results of an electrochemical analysis of zinc oxide nanopowder.

Zinc oxide nanopowder with a particle size of <100 nm was used in the following experiments. The nanopowder was partially soluble in water (pH 7) but completely soluble in water with nitric acid or hydrochloric acid at pH 2. For pH values 3 or greater, a precipitate was observed (FIG. 7A). For quantification of zinc by voltammetry, nitric acid was added to facilitate the availability in solution.

Figure 7B:

The pH of the extracts disclosed herein was approximately 6.89, with the soluble solids representing 0.0027 g/mL of device extract. At pH values of less than 3, a precipitate was observed, whereas appearance of the extracts was translucent at pH 10 (FIG. 7B).

Figure 7C:
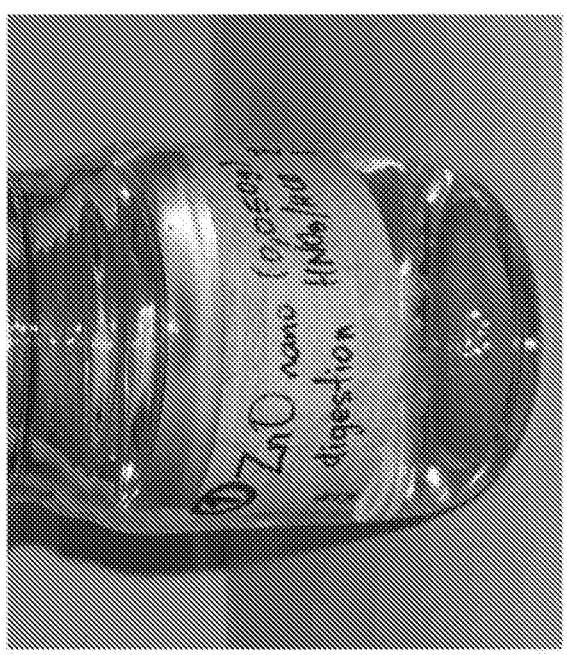

0.05 g of ZnO nanopowder was mixed with 5 mL of $HNO_3$ (65%) and 1 mL of 5M HCl and water was added to 50 mL. The solution was boiled for 10 min. An additional 5 mL of $HNO_3$ (65%) and 2 mL of 5M HCl were added and the samples were brought to a final volume of 100 mL with water to make a clear solution (FIG. 7C).

To determine the amount of device extract needed to obtain 0.05 g of solids, the following equation was used:

$$0.05 \text{ g} \times 0.0027 \text{ g/mL} = 18.5 \text{ mL}$$

Figure 7D:

Thus, 18.5 mL of device extract were measured into a flask. 5 mL of $HNO_3$ (65%) and 2 mL of HCl (5M) were added and deionized water was added to obtain a total volume of 50 mL. This solution was boiled for 10 min and brought to a final volume of 100 mL in the same manner as for the zinc oxide nanopowder samples (FIG. 7D).

Voltammetric measurements were conducted on a Voltamperimeter 797 VA Computrance (Metrohm) using 797 VA Computrance v. 1.3.2 software. Zinc (II) concentration was determined and quantified for experimental samples using ZnO nanopowder as the reference pattern. Samples were prepared with 100 μL of sample in 10 μL of deionized water and 500 mL of buffer (ammonium acetate, pH 4.6). Instrumental parameters are provided in Table 5:

TABLE 5

Instrumental Parameters for Zinc Determination

| | |
|---|---|
| Working electrode | HMDE |
| Stirrer speed | 2000 rpm |
| Mode | DP |
| Drop size | 4 |
| Calibration | Standard addition |
| Purge time | 300 s |
| Deposition potential | −1.15 V |
| Deposition time | 60 s |
| Equilibration time | 5 s |
| Pulse amplitude | 0.05 V |
| Start potential (condition cycles) | −1.2 V |
| End potential | −0.1 V |
| Start potential (sweep) | −1.15 V |
| End potential | −0.3 V |
| Voltage step | 0.0059 V |
| Voltage step time | 0.4 s |
| Sweep rate | 0.0149 V/s |
| Peak potential Zn | 0.96 V |

Figure 8A:
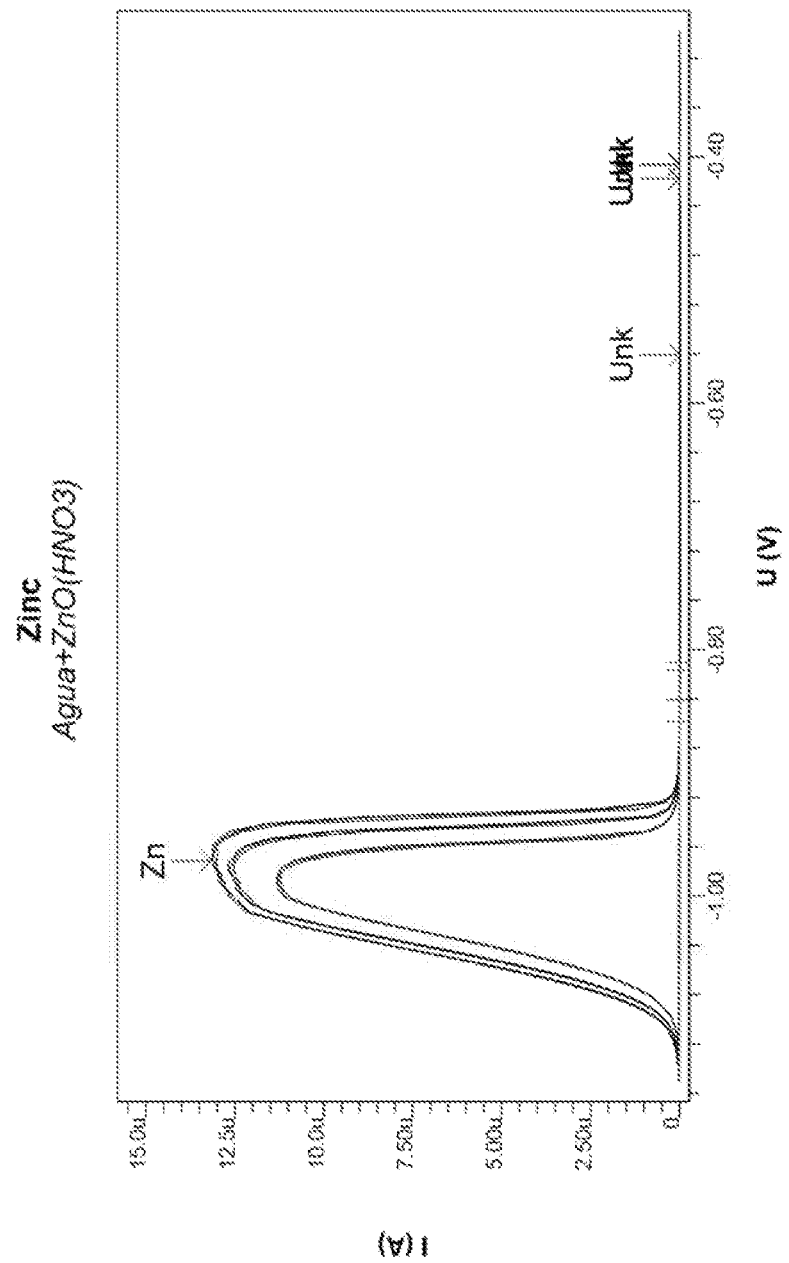
FIGS. 8A-B show output from a voltamperimeter for various experimental samples and controls.
Figure 8B:
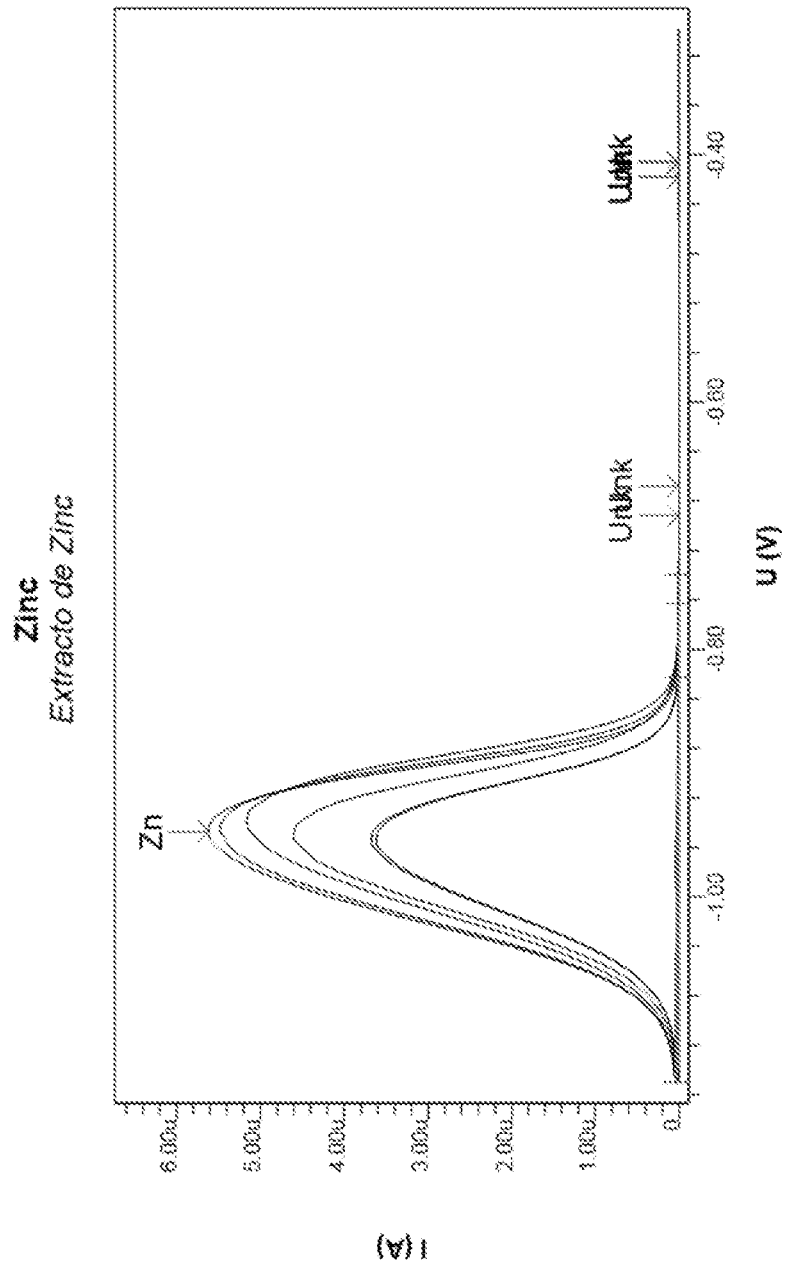

Calculations were performed according to a protocol provided by the manufacturer. The voltamperimeter measured the intensity of current in amperes versus the registered voltage. The zinc peak is specifically detected at −960 mV. Standard additions are made manually following measurement of the initial sample. Sample intensity graphs for zinc nanopowder in nitric acid and the zinc device extract without digestion can be seen in FIGS. 8A and 8B, respectively. Device extracts were filtered with a 0.2 μm nylon filter prior to measurement.

Figure 9A:
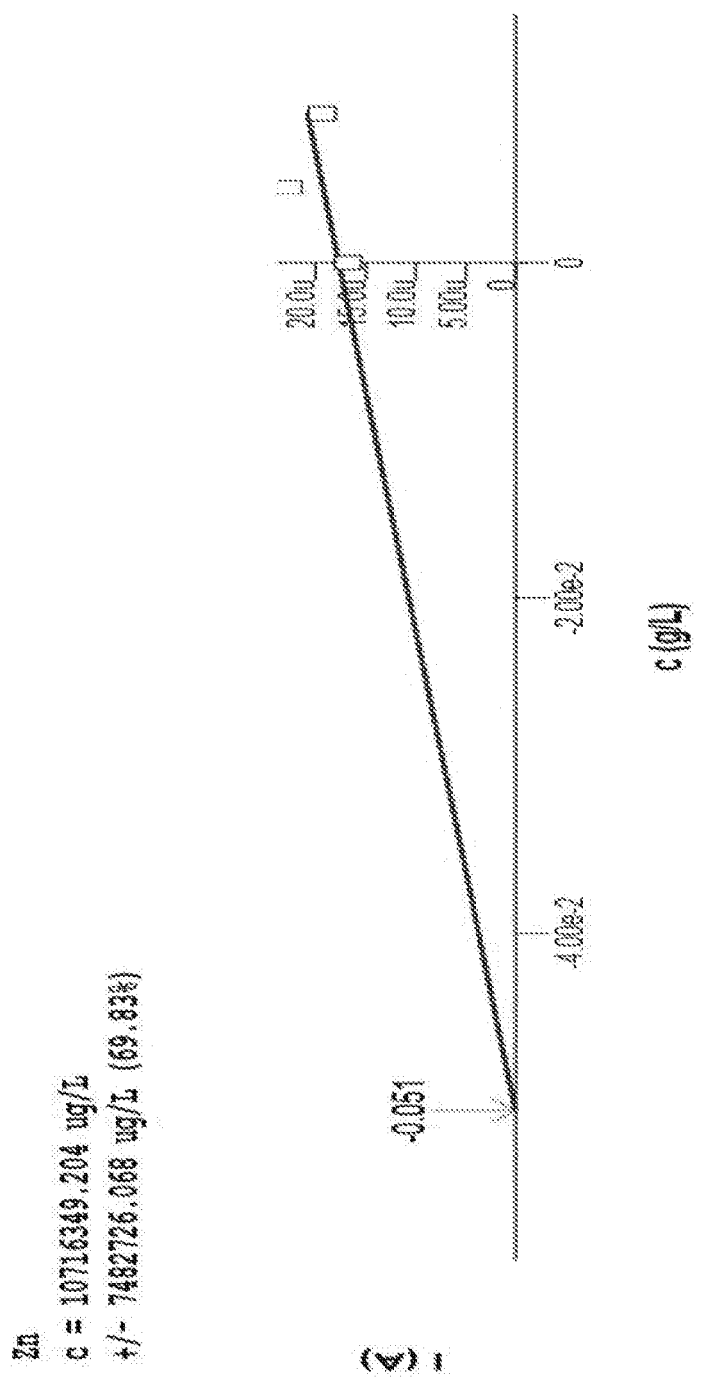
FIGS. 9A-F show calibration curves (current in A versus concentration in g/L) useful in the determination of zinc concentration in the devices disclosed herein.
Figure 9B:
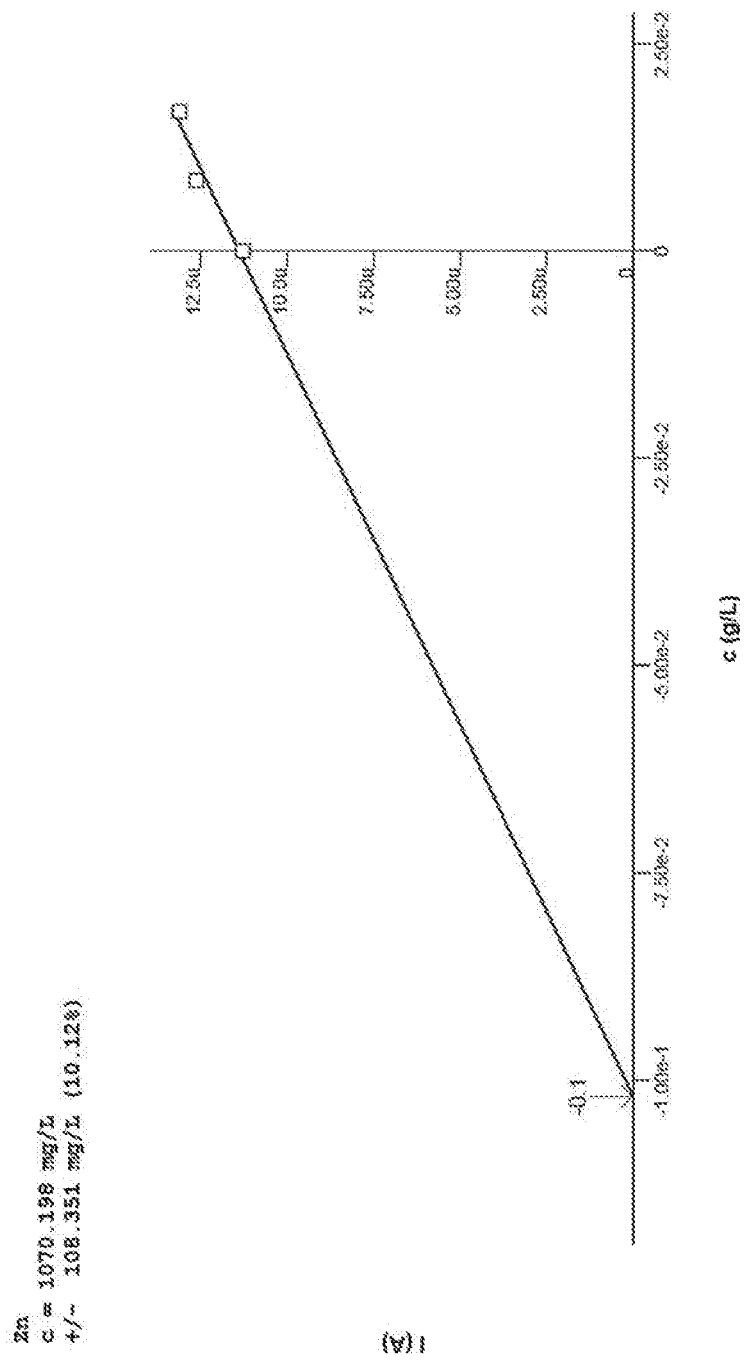
Figure 9C:
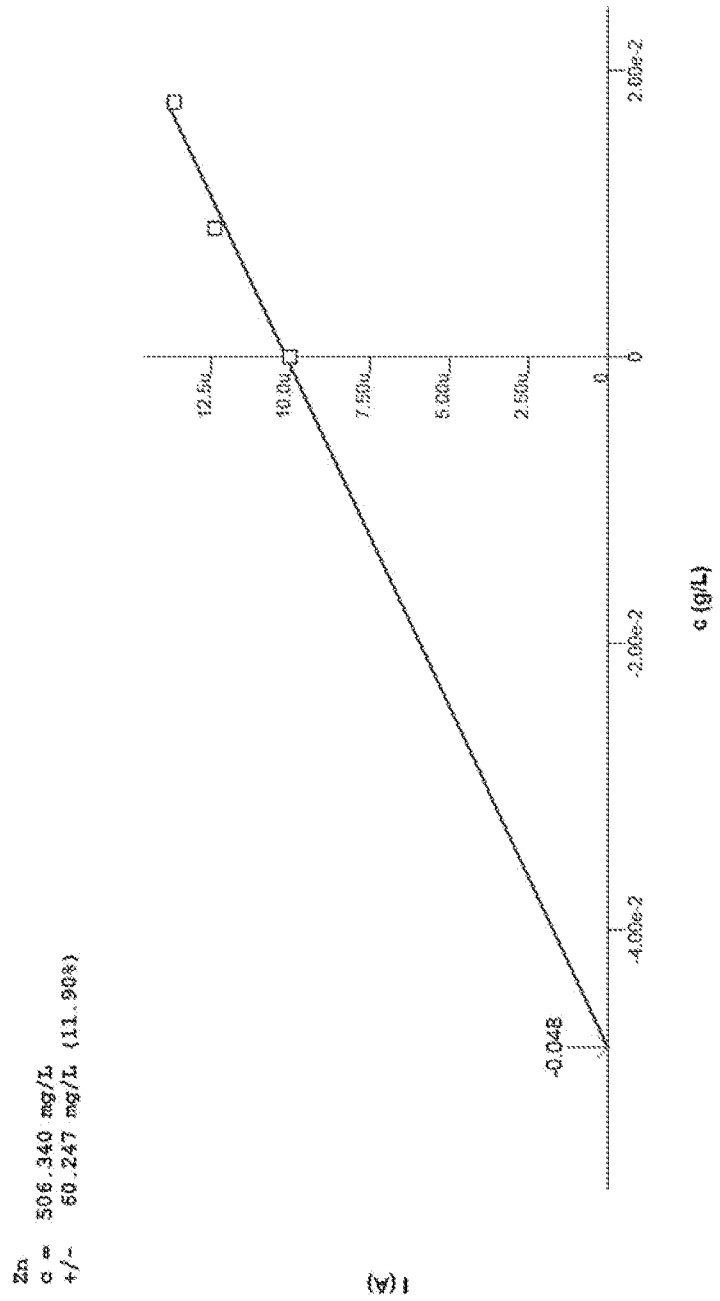
Figure 9D:
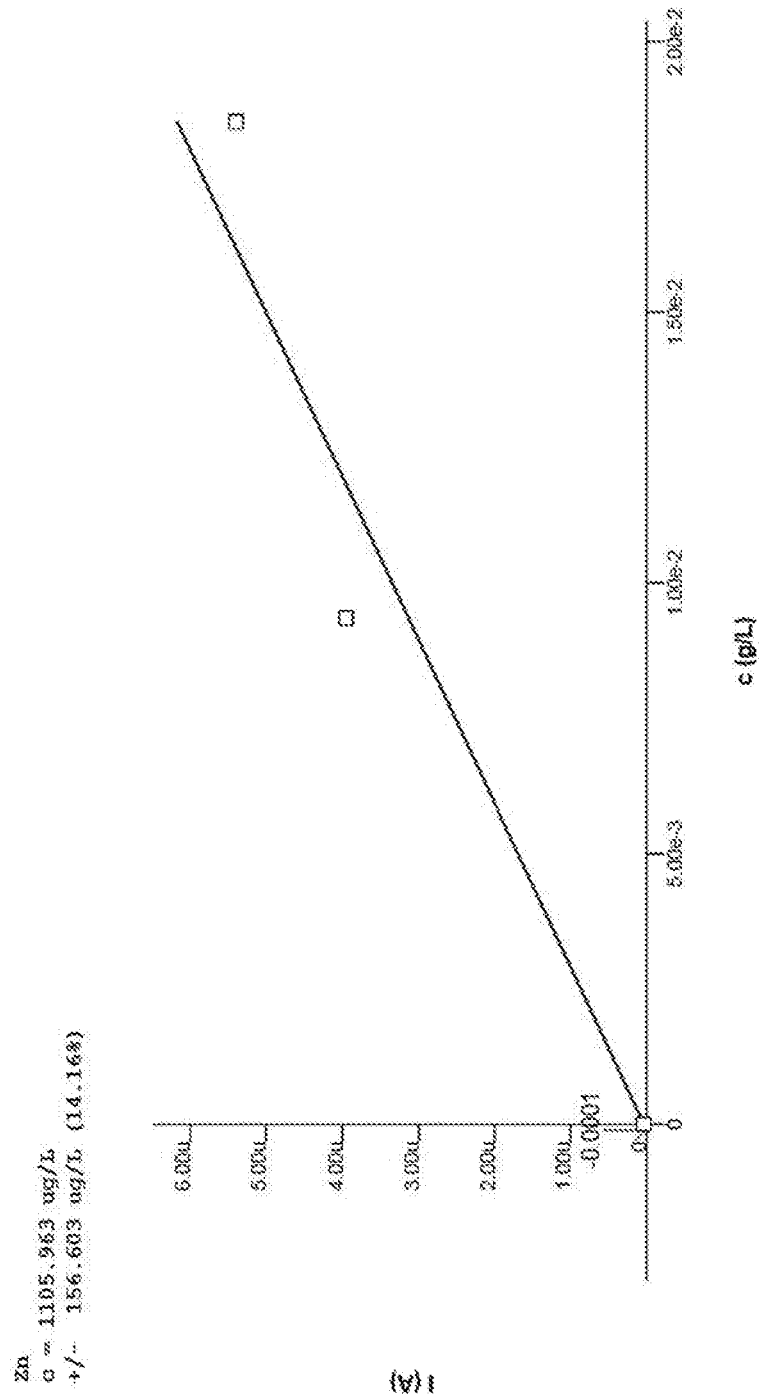
Figure 9E:
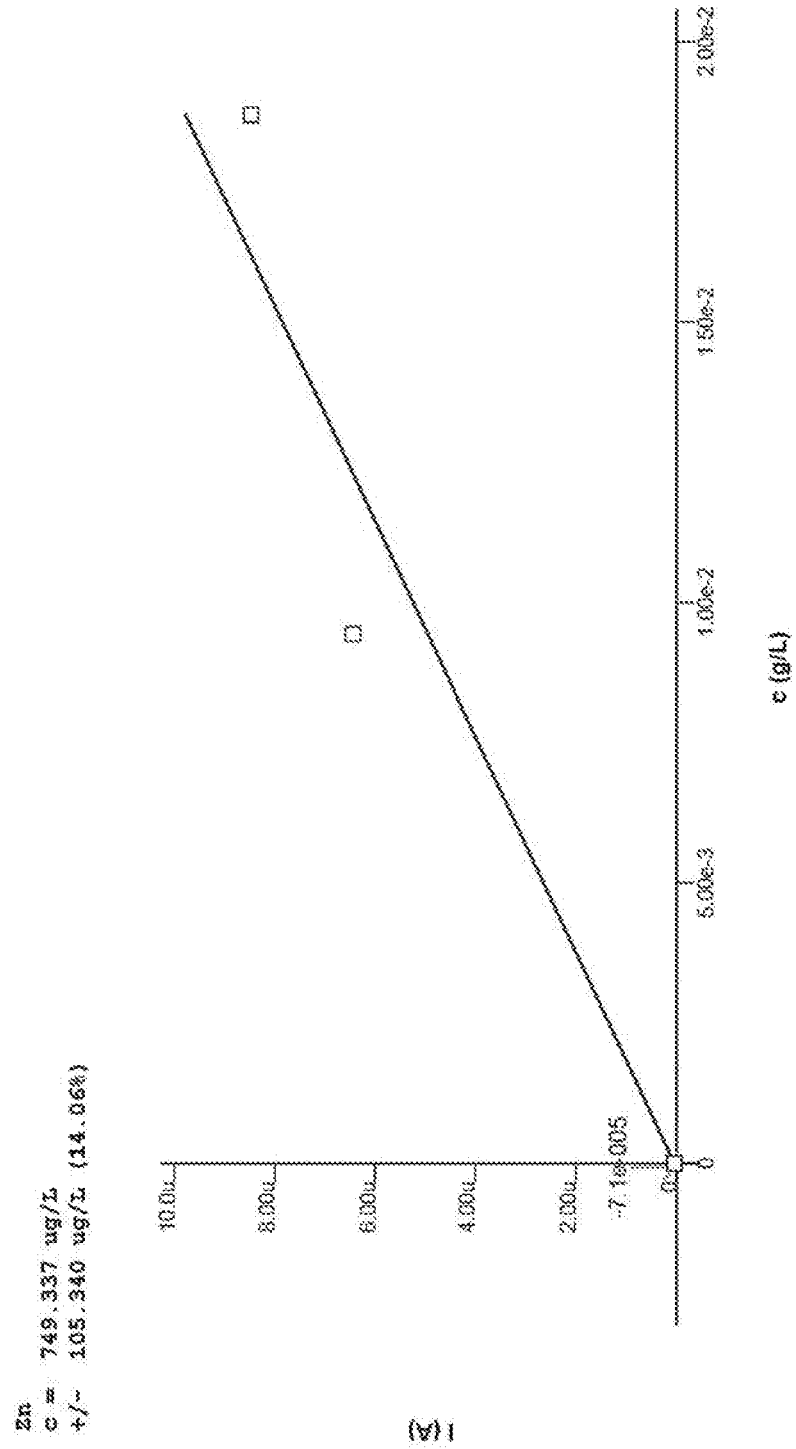
Figure 9F:
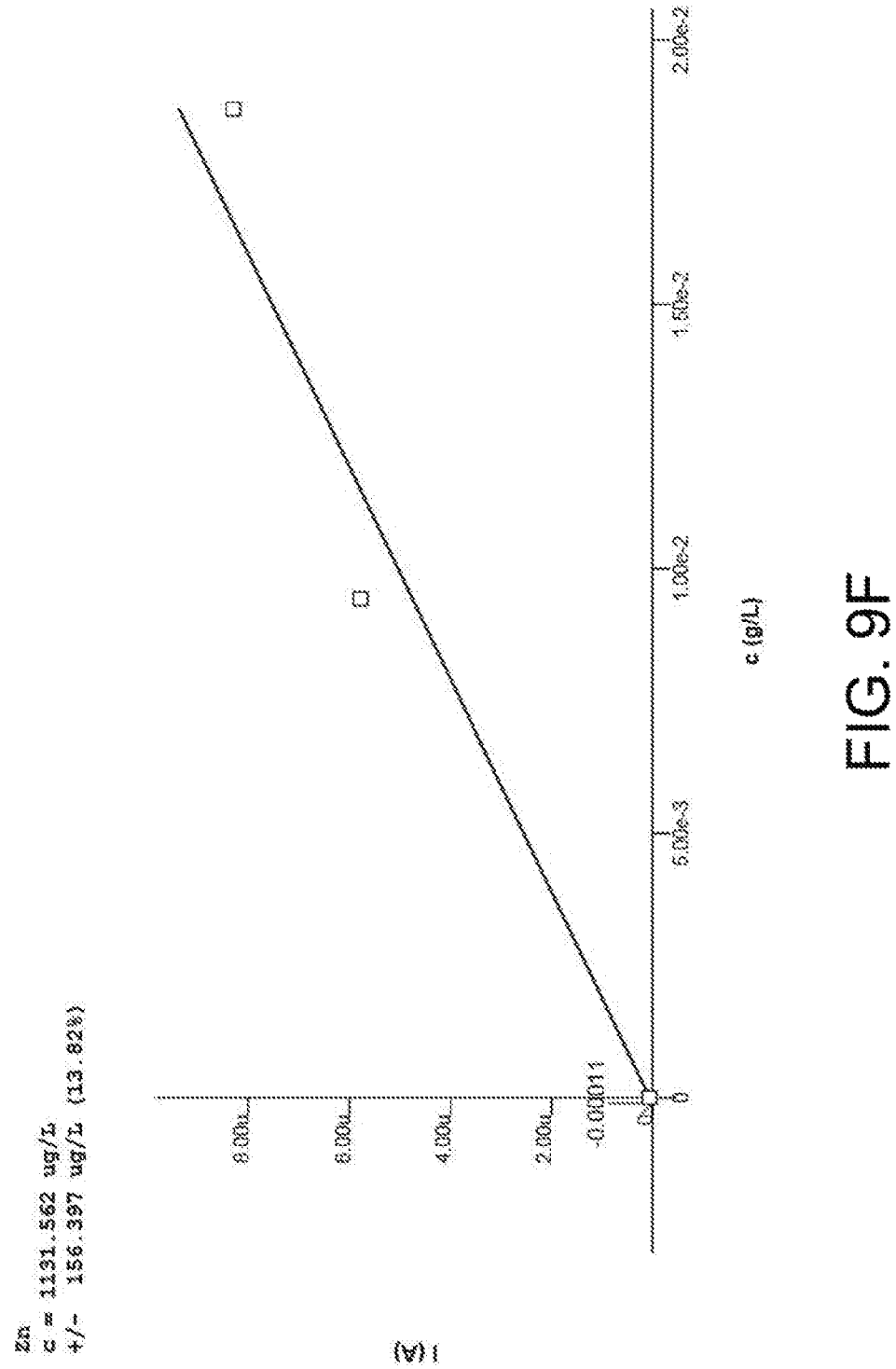

For quantification, calibration curves were constructed using a pure analytical zinc standard solution (1 g/L, Panreac). Standard curves were determined for the analytical solution (FIG. 9A), zinc oxide in nitric acid (FIG. 9B), digested zinc nanopowder (FIG. 9C), the zinc device extract (FIG. 9D), a lower concentration of the unfiltered zinc device extract (FIG. 9E), and the digested zinc device extract filtered through a 0.2 μm nylon filter (FIG. 9F). Results from the voltammetric measurements are presented in Table 6:

TABLE 6

Voltammetric Measurements

| | Zinc concentration (mg/L) | Standard deviation | Correction coefficient |
|---|---|---|---|
| ZnO nanopowder | 1070.198 | ±108.351 | 0.9714 |
| Diluted digestion of ZnO nanopowder | 506.34 | ±60.247 | 0.9362 |
| Concentrated zinc device extract | 11.05 | ±0.156 | 0.9608 |
| Diluted zinc device extract | 4.050 | ±0.105 | 0.9602 |
| Digestion filtered (Nylon 0.2 μm) of Zinc device extract (diluted) | 61.16 | ±0.156 | 0.9696 |

Based on measurements of the concentrated zinc device, an initial volume of 1 L will result in 11.05 mg/L of zinc. For a filtered digestion of the diluted zinc device extract, an initial volume of 1 L of extract will result in 61.16 mg/L of zinc. The zinc from the nanopowder and the device extracts was oxidized ($Zn^{2+}$).

Example 6: Chemical Analysis

Zinc concentration was also determined by complexometric titration with EDTA. Eriochrome black was used as indicator with a color change from blue to red (violet) to determine the endpoint of the titration. 0.05 g of zinc nanopowder sample was dissolved with 500 μL HCl with a final sample volume of 25 mL. 5 mL of this solution was mixed with 2 mL of an ammonium buffer (pH 9.5) and eriochrome black and 0.02M EDTA was added until the solution turned blue at which point the titration was stopped. For zinc device extracts, 18.5 mL samples were used. 500 μL of 5M HCl were added to the extract samples and diluted with deionized water to 25 mL, and then the titration was performed. Biological extract samples were filtered with a 0.2 μm nylon filter to reduce viscosity in order to perform the titrations. Results of $Zn^{2+}$ determination are presented in Table 7:

TABLE 7

Determination of Zinc Concentration by Complexometric Titration

| | Concentration (mg/L) | Standard deviation | C.V. |
|---|---|---|---|
| Zinc nanopowder | 2124.836 | ±29.921 | 1.41% |
| Device extracts | 22.675 | ±6.478 | 28.57% |

The components present in the extract were further evaluated. The extract was evaporated in a water bath and reduced from an initial volume of 60 mL to a final volume of 7 mL. This solution was fractionated by a solid phase column manufactured with RP-18 (40-63 μm) from Merck. The stationary phase was activated with the initial water (0.1% TFA) phase, approximately 5 volumes of the stationary phase were passed for a total of 125 mL. The concentrated extract solution was added followed by the addition of different solvents, with acetonitrile being added in 10%. A total of 11 fractions of 50 mL each were obtained using the following solvents: 1) Water (0.1% TFA). 2) 10% ANC: Water (0.1% TFA). 3) 20% ANC: Water (0.1% TFA). 4) 30% ACN: Water (0.1% TFA). 5) 40% ACN: Water (0.1% TFA). 6) 50% ACN: Water (0.1% TFA). 7) 60% ACN: Water (0.1% TFA). 8) 70% ACN: Water (0.1% TFA). 9) 80% ACN: Water (0.1% TFA). 10) 90% ACN: Water (0.1% TFA). 11) 100% ACN.

TLC chromatography was performed with the first fraction collected from the column. The sample was concentrated by evaporation and applied to four TLC RP-18 plates (10×10 cm) 4 plates. Subsequently, three bands (samples 1, 2, and 3) were cut from each plate and scraped from the plate. Additionally, TLC chromatography was performed with the sixth fraction collected from the column (sample 4). In order to extract the zinc compound from the stationary phase of each band, water (0.1% TFA) 90:10 methanol was added to the scraping dust and it was taken to an ultrasonic bath for 20 minutes 2 times each. Then each fraction was concentrated by evaporation and observed with the UV-lamp (365 nm). The amount of oxidized zinc present in each sample was determined by electrochemical analysis as described above with the results provided in Table 8. Thus, the extract produced by the zinc device produced multiple oxidized zinc species.

TABLE 8

| Sample | Result [mg/L] | Std. Dev. | Corr. Coeff. |
|---|---|---|---|
| 1 | 0.593 | ±0.021 | 0.91789 |
| 2 | 3.835 | ±0.087 | 0.93781 |
| 3 | 3.166 | ±0.087 | 0.90946 |
| 4 | 5.002 | ±0.119 | 0.93693 |

Example 7: Use of the Yeast-Zinc Device for UV Protection of Bacterial Cultures

Figures 3A, 3B:
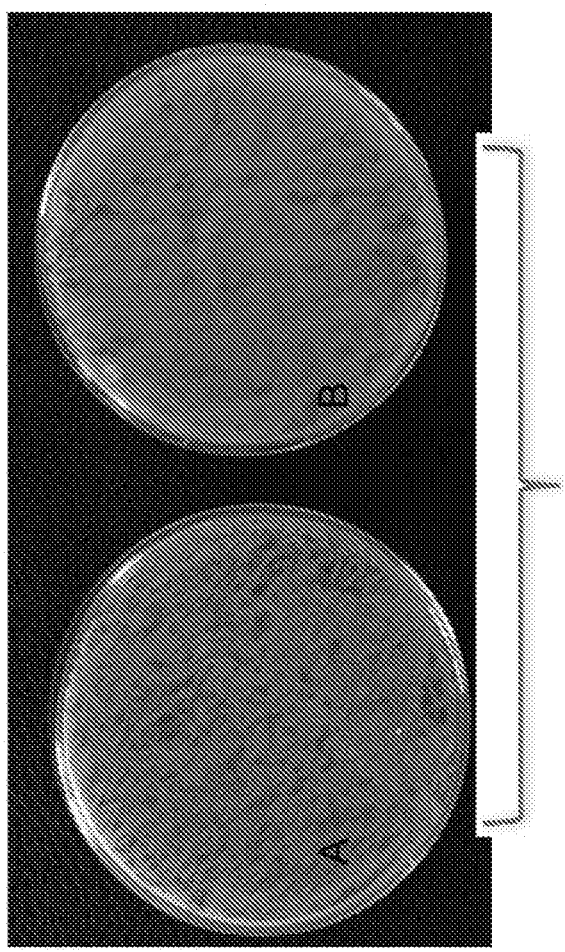
FIGS. 3A and 3B show two replicates of a *Bacillus subtilis* culture after 24 hours and before exposure to UV radiation.
Figure 4A:
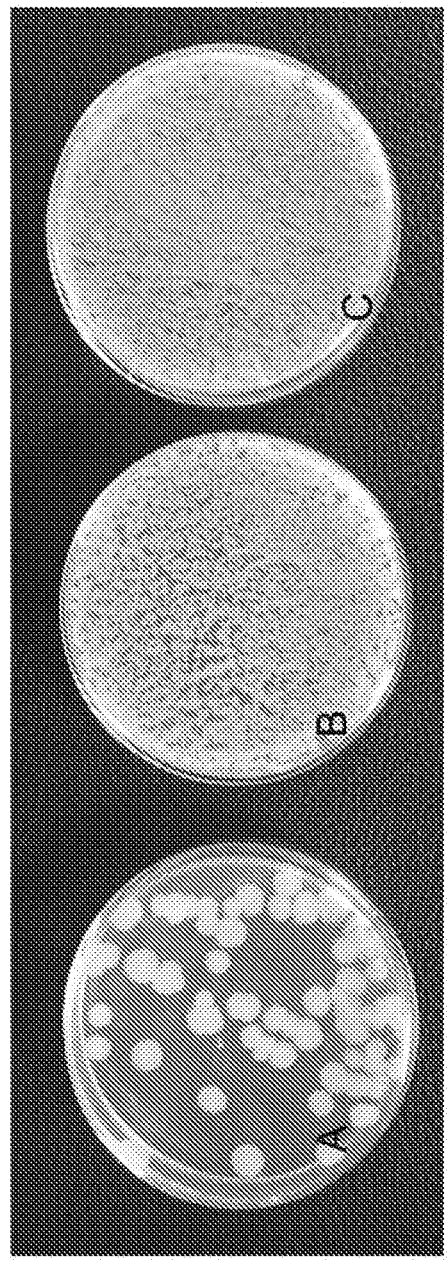
FIGS. 4A-C show bacterial growth after UV exposure.
Figure 4B:
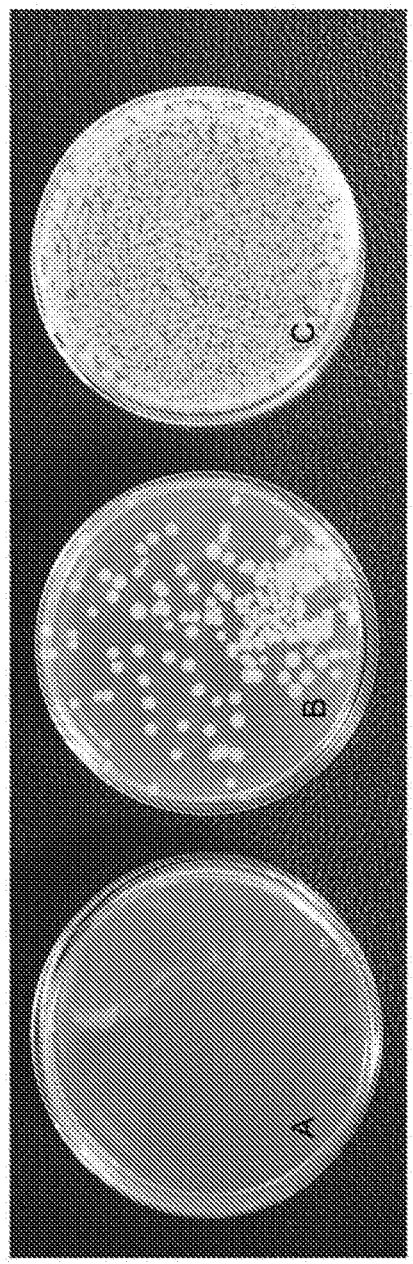
Figure 4C:
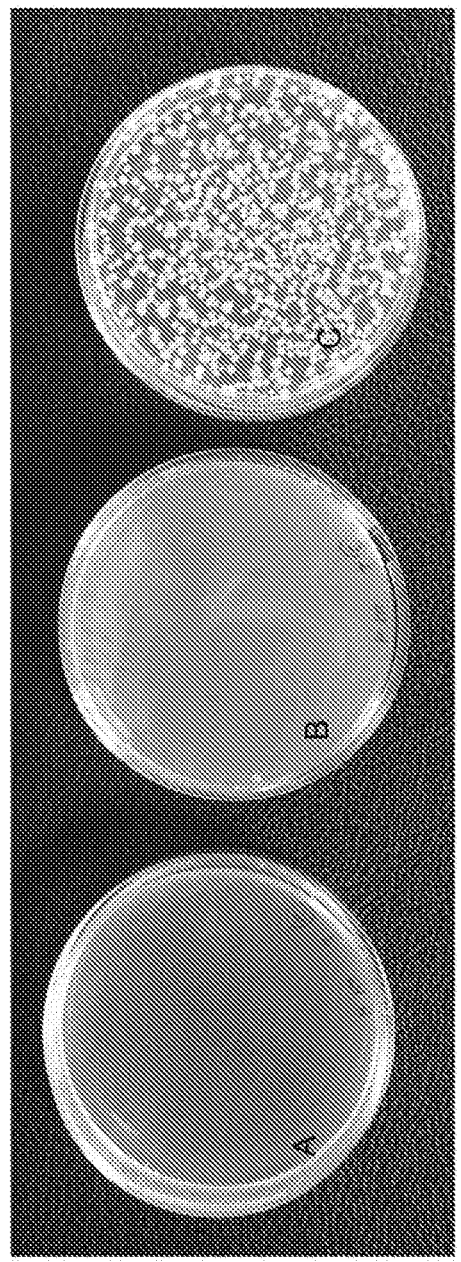

A culture of *Bacillus subtilis* was used for testing the UV-protective effects of the extracts described herein. Cultures of *B. subtilis* (0.1-0.2 optical density) were used. 5 mL of these cultures were mixed in Petri dishes with 1, 2, 5, 10, 15, or 20 mL of extracts from the yeast-zinc device; in general, 10 mL was preferred. The *B. subtilis*/biological device mixtures were exposed to UV radiation (either 254 nm or 365 nm, though 254 nm was preferred) while being protected from non-controlled, outside sources of light. UV exposure was carried out for up to 24 hours at room temperature (24-27° C.). Samples were removed at 0, 30, and 60 minutes as well as at 24 hours. Each sample consisted of a 200 µL aliquot of the treated mixture, which was plated in nutrient agar and incubated at 37° C. for 24 hours. Growth of bacteria was determined by the presence of colonies at each sampling time. FIG. 3 shows sample *B. subtilis* cultures prior to UV exposure. FIGS. 4A-4C show an untreated control (left petri dish), a low concentration of bacteria treated with the extracts described herein and exposed to UV (middle petri dish), and a high concentration of bacteria treated with the extracts described herein and exposed to UV (right petri dish) at different time points (30 min, 1 hour, 24 hours). Treated bacterial cultures (middle and right dishes) show higher bacterial colony counts than untreated cultures (left dish), thus demonstrating the protective effects of the extracts.

Figure 5A:
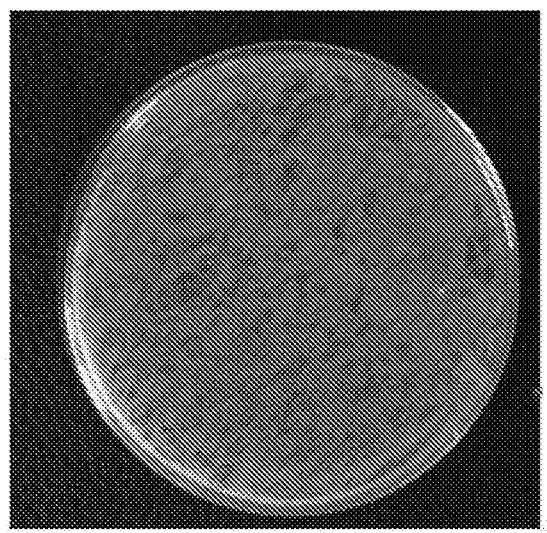
FIGS. 5A-D show *Bacillus subtilis* cultures before and after exposure to UV light.
Figure 5B:
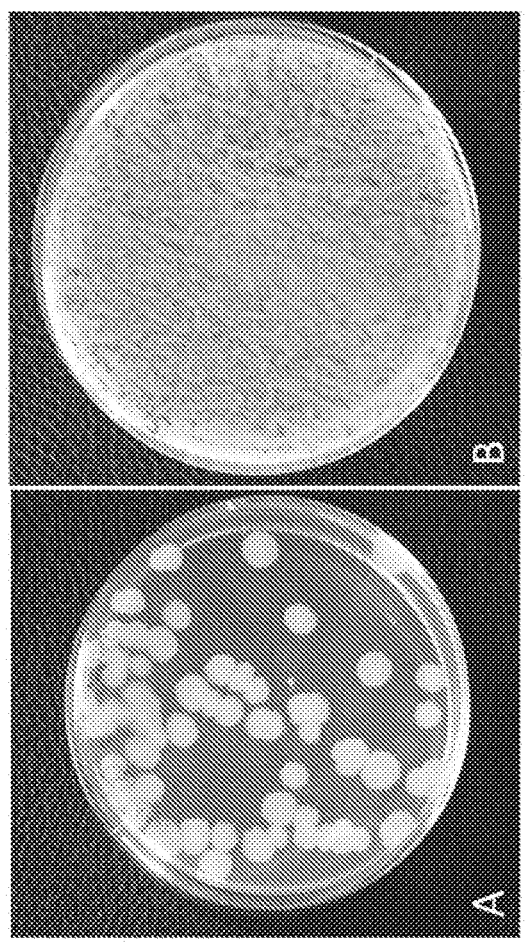
Figure 5C:
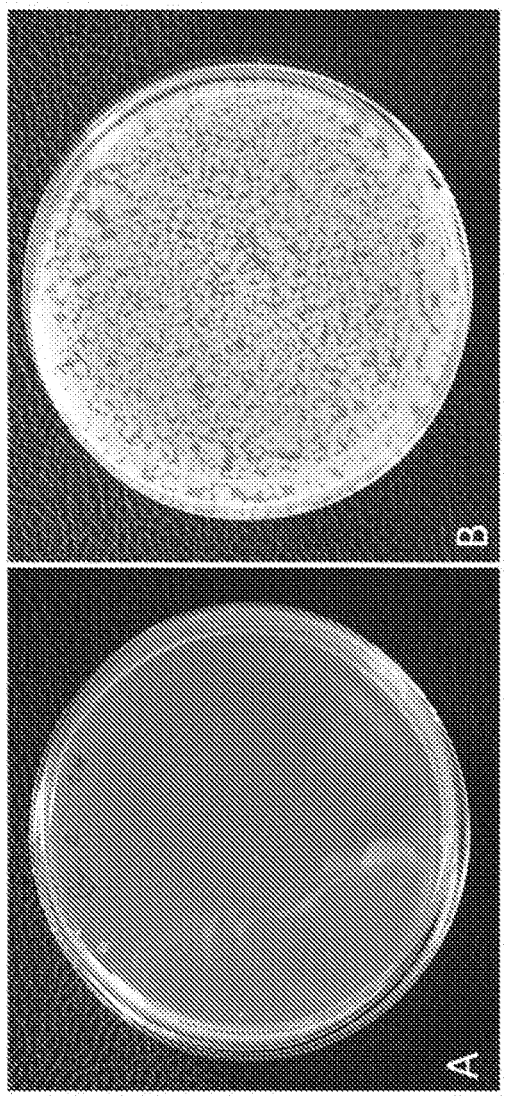
Figure 5D:
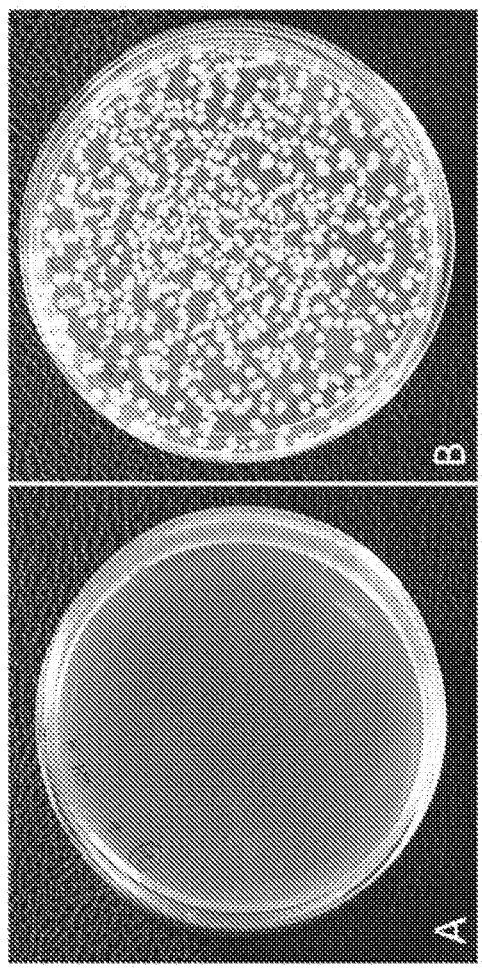

Results of additional trials and experiments are shown in FIGS. 5A-5D and 6A-6B. In these experiments, the effectiveness of a nanopowder form of zinc oxide (particle size<100 nm) at shielding bacterial samples from UV radiation was compared to extracts from the devices disclosed herein. For these experiments, a 254 nm shortwave UV lamp (Cole Parmer) was placed at 20 cm from the samples to be irradiated. Prior to UV exposure, *B. subtilis* showed complete coverage of the experimental plate, with a concentration of greater than $1 \times 10^6$ cells (FIG. 5A). After 30 minutes of exposure to UV light, abnormally shaped colonies were observed for an untreated control, while complete coverage of the plate was again seen in samples treated with the extracts disclosed herein (FIG. 5B). After 1 hour of exposure to UV light, complete cell death was observed in untreated colonies, whereas complete coverage of the plate was again seen in treated samples (FIG. 5C). After 24 hours of exposure to UV light, some decline in cell count was seen in treated samples (i.e., approximately $1 \times 10^5$ cells were present) (FIG. 5D).

Figure 6A:
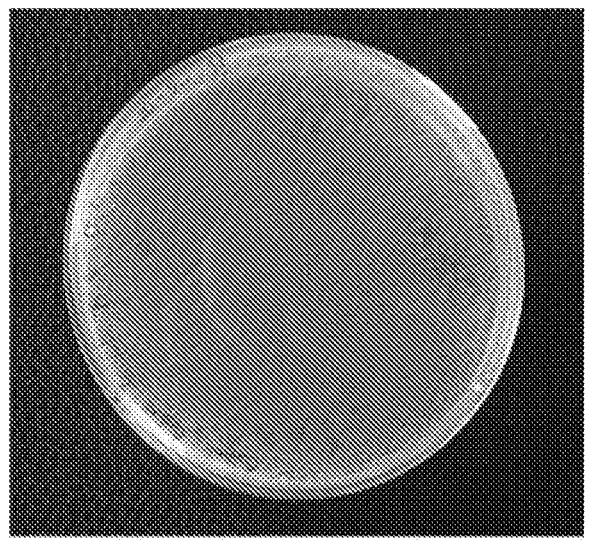
FIGS. 6A-B show *B. subtilits* cultures before and after exposure to UV light.
Figure 6B:
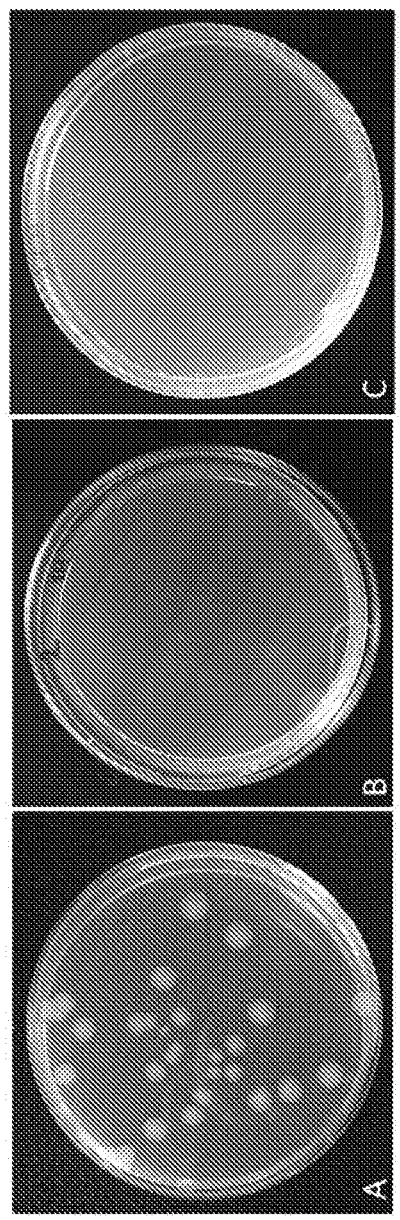

A comparative experiment was conducted using zinc oxide nanopowder with a particle size of <100 nm (Sigma-Aldrich). Prior to UV exposure, cell count in the experimental plate for the sample was approximately $1 \times 10^6$ (FIG. 6A). Following 30 minutes of exposure, abnormal colonies were observed with a cell count of about $1 \times 10^3$; after 1 hour of exposure, complete cell death was observed (FIG. 6B).

Example 8: Use of the Yeast-Zinc Device for UV Protection of Bacterial Cultures

A culture of *Bacillus subtilis* (ATCC 82) was grown at 30° C. for one to two days. Aliquots were taken from this culture and subjected to different bacteria dilutions and the concentration was determined spectrophotometrically at the respective optical density (OD) between 1.0 to 1.5.

Solutions were made from the above dilutions and mixed with different concentrations of extract from Zinc devices, those obtaining different volume ratios (i.e. 8:2, 10:2, zinc extract:bacteria). These solutions were placed in Petri dishes with a total volume of 10 mL and 12 mL respectably. These solutions were made in triplicates.

The solutions were placed in the UV incubator at 30° C. and samples were exposed to UV radiation at different times (i.e. 30 minutes, 1 hour, 12 hours). In a different experiment, the zinc extract (8 or 10 mL) was exposed to radiation (e.g., 30 minutes). At each time interval, aliquots of 1 mL bacterial samples were taken from each replicate (total sampling volume 3 mL) and fully mixed. Then, 500 µL were taken and placed on Nutrient agar by using standard streaking method. Three agar plate replicates were used at each time. The agar plates were incubated at 30° C. for 1-4 days. Bacterial colonies of *Bacillus subtilis* were viewed and counted at each time.

Bacterial colonies samples were stained by using standard Gram staining technique and observed in the compound microscope in order to see the morphology of the *B. subtilis* bacteria.

Table 9 show *B. subtilis* culture treated with zinc extract and exposed to UV-B radiation (302 nm) showed higher growth by covering the agar plate completely as compared to *B. subtilis* without exposure to the zinc extract, which showed very low growth or no growth at all after exposure to radiation. This confirms the ability of the zinc extract to impart UV protection.

TABLE 9

Protective effect of zinc extract (500 µg/L) on *Bacillus subtilis* (ATCC 82) against UV-B radiation (302 nm) at different exposure times and extract/bacteria volume ratios
Protective effect of Zinc Device on *Bacillus subtilis* (ATCC 82), Against UV-B at different times
initial *B. subtilis* culture alone + no UV-B
Colonies covers the plate completly

| *B. subtilis* alone + UV-B<br>Count before UV-B expousure<br>Colonies covers the plate completly | | | | *B. subtilis* + Zn Device +<br>UV-B(10:2, Device extract Bacteria)<br>Count before UV-B expousure<br>Colonies covers the plate completly | |
|---|---|---|---|---|---|
| *B. subtilis* + Zn Device + UV-B | *B. subtilis* + Zn Device + UV-B | *B. subtilis* + Zn Device + UV-B | *B. subtilis* + Zn Device + UV-B | *B. subtilis* + Zn Device + UV-B | *B. subtilis* + Zn Device + UV-B |

TABLE 9-continued

Protective effect of zinc extract (500 μg/L) on *Bacillus subtilis* (ATCC 82)
against UV-B radiation (302 nm) at different exposure times and extract/bacteria volume ratios
Protective effect of Zinc Device on *Bacillus subtilis* (ATCC 82), Against UV-B at different times
initial *B. subtilis* culture alone + no UV-B
Colonies covers the plate completly

| *B. subtilis* alone + UV-B Count before UV-B expousure | (10:2, Device extract: Bacteria) Count before UV-B expousure | (8:2, Device extract: Bacteria) Count before UV-B expousure | *B. subtilis* alone + UV-B 30 minutes UV-B expousure | (10:2, Device extract: Bacteria) 30 minutes UV-B expousure | (8:2, Device extract: Bacteria) 30 minutes UV-B expousure | *B. subtilis* alone + UV-B 1 hour UV-B expousure | (10:2, Device extract: Bacteria) 1 hour UV-B expousure | (8:2, Device extract: Bacteria) 1 hour UV-B expousure | *B. subtilis* alone + UV-B 4 hour UV-B expousure |
|---|---|---|---|---|---|---|---|---|---|
| CPC | CPC | CPC | CPC | CPC | CPC | 4 | CPC | CPC | 0 |

*B. subtilis* + Zn Device +
UV-B(8:2, Device extract Bacteria)
Count before UV-B exposure
Colonies covers the plate completly

| *B. subtilis* + Zn Device + UV-B(10:2, Device extract: Bacteria) 4 hour UV-B expousure | *B. subtilis* + Zn Device + UV-B(8:2, Device extract: Bacteria) 4 hour UV-B expousure | *B. subtilis* alone + UV-B 8 hour UV-B expousure | *B. subtilis* + Zn Device + UV-B(10:2, Device extract: Bacteria) 8 hour UV-B expousure | *B. subtilis* + Zn Device + UV-B(8:2, Device extract: Bacteria) 8 hour UV-B expousure |
|---|---|---|---|---|
| 217 | 68 | 0 | 1 | 50 |

* CPC means colonies covers the plate completly

Tables 10 and 11 show *B. subtilis* culture treated with zinc extract and exposed to UV-B radiation (302 nm) showed higher growth by covering the agar plate completely as compared to *B. subtilis* without exposure to zinc extract and exposed to UV-B radiation, which showed very low growth or no growth at all after exposure to radiation. This confirms the ability of the zinc extract to impart UV protection.

TABLE 10

Protective effect of zinc extract (500 μg/L) on *Bacillus subtilis* (ATCC 82)
against UV-B radiation (302 nm) at different times and extract/bacteria volume ratios
with reapplication at 30 minutes after radiation exposure
Protective effect of Zinc Device on *Bacillus subtilis* (ATCC 82), Against UV-B at different times
initial *B. subtilis* culture alone + no UV-B
Colonies covers the plate completly

| | *B. subtilis* alone + UV-B 30 minutes UV-B exposure before R 3480,00 | | | *B. subtilis* + Zn Device + UV-B (10:2, Device extract:Bacteria) 30 minutes UV-B exposure before R Colonies covers the plate completly | | | *B. subtilis* + Zn Device + UV-B (8:2, Device extract: Bacteria) 30 minutes UV-B exposure before R Colonies covers the plate completly | | |
|---|---|---|---|---|---|---|---|---|---|
| | | | | reapplication* after 30 minutes UV-B exposure | | | | | |
| *B. subtilis* alone + UV-B Count before reappli- cation | *B. subtilis* + Zn Device + UV-B (10:2, Device extract: Bacteria) Count before reappli- cation | *B. subtilis* + Zn Device + UV-B (8:2, Device extract: Bacteria) Count before reappli- cation | *B. subtilis* alone + UV-B 30 minutes UV-B exposure after R | *B. subtilis* + Zn Device + UV-B (10:2, Device extract: Bacteria) 30 minutes UV-B exposure after R | *B. subtilis* + Zn Device + UV-B (8:2, Device extract: Bacteria) 30 minutes UV-B exposure after R | *B. subtilis* alone + UV-B 1 hour UV-B exposure after R | *B. subtilis* + Zn Device + UV-B (10:2, Device extract: Bacteria) 1 hour UV-B exposure after R | *B. subtilis* + Zn Device + UV-B (8:2, Device extract: Bacteria) 1 hour UV-B exposure after R | *B. subtilis* alone + UV-B 12 hour UV-B exposure after R |
| 3480 | CPC | CPC | 80 | CPC | CPC | 0 | CPC | CPC | 0 |

Additional columns (continued): *B. subtilis* + Zn Device + UV-B (10:2, Device extract: Bacteria) 12 hour UV-B exposure after R = 3312; *B. subtilis* + Zn Device + UV-B (8:2, Device extract: Bacteria) 12 hour UV-B exposure after R = 310.

*CPC means colonies covers the plate completly

TABLE 11

Protective effect of zinc extract (500 µg/L) on *Bacillus subtilis* (ATCC 82)
against UV-B radiation (302 nm) at different times and extract/bacteria volume ratios
with reapplication at one hour after radiation exposure
Protective effect of Zinc Device on *Bacillus subtilis* (ATCC 82), Against UV-B at different times
initial *B. subtilis* culture alone + no UV-B
Colonies covers the plate completly

| *B. subtilis* alone + UV-B<br>30 minutes UV-B expousure before R<br>Colonies covers the plate completly<br>B.subtilis alone + UV-B<br>1 hour UV-B expousure before R<br>350,00 | | | B.subtilis + Zn Device +<br>UV-B (10:2, Device extract:<br>30 minutes UV-B exposure before R<br>Colonies covers the plate completly<br>*B. subtilis* + Zn Device +<br>UV-B (10:2, Device extract:<br>1 hour UV-B exposure before R<br>Colonies covers the plate completly<br>reapplication* after 1 hour UV-B expousure | | | *B. subtilis* + Zn Device +<br>UV-B (8:2, Device extract:<br>30 minutes UV-B exposure before R<br>Colonies covers the plate completly<br>*B. subtilis* + Zn Device +<br>UV-B (8:2, Device extract:<br>1 hour UV-B expousure before R<br>Colonies covers the plate completly | | |
|---|---|---|---|---|---|---|---|---|
| *B. subtilis* alone + UV-B Count before reapplication | *B. subtilis* + Zn Device + UV-B (10:2, Device extract: Bacteria) Count before reapplication | *B. subtilis* + Zn Device + UV-B (8:2, Device extract: Bacteria) Count before reapplication | *B. subtilis* alone + UV-B 30 minutes UV-B expousure after R | *B. subtilis* + Zn Device + UV-B (10:2, Device extract: Bacteria) 30 minutes UV-B expousure after R | *B. subtilis* + Zn Device + UV-B (8:2, Device extract: Bacteria) 30 minutes UV-B expousure after R | *B. subtilis* alone + UV-B 1 hour UV-B expousure after R | *B. subtilis* + Zn Device + UV-B (10:2, Device extract: Bacteria) 1 hour UV-B expousure after R | *B. subtilis* + Zn Device + UV-B (8:2, Device extract: Bacteria) 1 hour UV-B expousure after R | *B. subtilis* alone + UV-B 4 hour UV-B expousure after R | *B. subtilis* + Zn Device + UV-B (10:2, Device extract: Bacteria) 4 hour UV-B expousure after R | *B. subtilis* + Zn Device + UV-B (8:2, Device extract: Bacteria) 4 hour UV-B expousure after R |
| 350 | CPC | CPC | 28 | CPC | CPC | 14 | CPC | CPC | 0 | CPC | CPC |

*CPC means colonies covers the plate completly

Table 12 shows *B. subtilis* culture treated with the zinc extract and exposed to UV-A radiation (365 nm) showed higher growth by covering the agar plate completely as compared to *B. subtilis* without exposure to zinc extract, which showed very low growth or no growth at all after exposure to UV-A radiation. This confirms the ability of the zinc extract to impart UV protection.

TABLE 12

Protective effect of zinc extract (~500 µg/L) on *Bacillus subtilis* (ATCC 82) against
UV-A radiation (365 nm) at different times and extract/bacteria volume ratios
Protective effect of Zinc Device on *Bacillus subtilis* (ATCC 82), Against UV-A at different times
initial *B. subtilis* culture alone- no UV-A
Colonies covers the plate completly

| *B. subtilis* alone + UV-A<br>Count before UV-A exposure<br>Colonies covers the plate completly | | | | | | | *B. subtilis* + Zn Device + UV-A (4:1, Device extract: Bacteria)<br>Count before UV-A exposure<br>Colonies covers the plate completly | | | | | | |
|---|---|---|---|---|---|---|---|---|---|---|---|---|---|
| *B. subtilis* alone + UV-A Count before UV-A expousure | *B. subtilis* + Zn Device + UV-A (4:1, Device extract: Bacteria) Count before UV-A expousure | *B. subtilis* alone + UV-A 30 minutes UV-A expousure | *B. subtilis* + Zn Device + UV-A (4:1, Device extract: Bacteria) 30 minutes UV-A expousure | *B. subtilis* alone + UV-A 45 minutes UV-A expousure | *B. subtilis* + Zn Device + UV-A (4:1, Device extract: Bacteria) 45 minutes UV-A expousure | *B. subtilis* alone + UV-A 1 hour UV-A expousure | *B. subtilis* + Zn Device + UV-A (4:1, Device extract: Bacteria) 1 hour UV-A expousure | *B. subtilis* alone + UV-A 4 hour UV-A expousure | *B. subtilis* + Zn Device + UV-A (4:1, Device extract: Bacteria) 4 hour UV-A expousure | *B. subtilis* alone + UV-A 8 hour UV-A expousure | *B. subtilis* + Zn Device + UV-A (4:1, Device extract: Bacteria) 8 hour UV-A expousure | *B. subtilis* alone + UV-A 24 hour UV-A expousure | *B. subtilis* + Zn Device + UV-A (4:1, Device extract: Bacteria) 24 hour UV-A expousure |
| CPC | CPC | 60 | CPC | 29 | CPC | 25 | 210 | 0 | CPC | 86 | CPC | 104 | CPC |

* CPC means colonies covers the plate completly

Table 13 shows *B. subtilis* culture treated with zinc extract and exposed to UV-C radiation (254 nm) showed higher growth by covering the agar plate completely as compared to *B. subtilis* without exposure to zinc extract, which showed very low growth or no growth at all after exposure to UV-C. This confirms the ability of the zinc extract to impart UV protection.

TABLE 13

Protective effect of zinc extract (1.3 mg/L) on *Bacillus subtilis* (ATCC 82) against UV-C radiation (254 nm) at different times and extract/bacteria volume ratios
Protective effect of Zinc Device on *Bacillus subtilis* (ATCC 82),
Against UV-C at different times
initial *B. subtilis* culture alone + no UV-C
Colonies covers the plate completly

| *B. subtilis* alone + UV-C Count before UV-C expousure Colonies covers the plate completly | | | | *B. subtilis* + Zn Device + UV-C (4:1, Device extract: Count before UV-C expousure Colonies covers the plate completly | | | |
|---|---|---|---|---|---|---|---|
| *B. subtilis* alone + UV-C Count before UV-C expousure | *B. subtilis* + Zn Device + UV-C (4:1, Device extract: Bacteria) Count before UV-C | *B. subtilis* alone + UV-C 30 minutes UV-C expousure | *B. subtilis* + Zn Device + UV-C (4:1, Device extract: Bacteria) 30 minutes UV-C expousure | *B. subtilis* alone + UV-C 1 hour UV-C expousure | *B. subtilis* + Zn Device + UV-C (4:1, Device extract: Bacteria) 1 hour UV-C expousure | *B. subtilis* alone + UV-C 24 hour UV-C expousure | *B. subtilis* + Zn Device + UV-C (4:1, Device extract: Bacteria) 24 hour UV-C expousure |
| CPC | CPC | 46 | CPC | 0 | CPC | 0 | 368 |

* CPC means colonies covers the plate completly

Example 9: Protective Effect of Oxidized Zinc on Fibroblast Cell Production of Oxidized Zinc The following steps were performed to produce and isolate the oxidized zinc extract:
1. Fermentation in yeast malt medium with 2% of raffinose and induction with 1% of galactose at 30° C. for 72 hours.
2. Sonication: 7 times for 2.5 minutes.
3. Filtration of supernatant by 8 µm, 3 µm, 2 µm and 1.2 µm.

Procedure

Skin fibroblast cells (ATCC 2522-CRL) were used as a model for human skin and were maintained in culture media for propagation and renewal following ATCC recommendations. The propagation medium is based on ATCC-formulated Eagles's Minimum Essential Medium, Catalog No 30-2003. Fetal bovine serum was added to the medium to a final concentration of 10%. The medium was also renewed according to ATCC instructions. This medium is made of 0.025% trypsin, 0.03% EDTA solution. Cultures of fibroblast cells (ATCC 2522-CRL) were grown at 37° C. and 5% $CO_2$.

Oxidized zinc extract was applied to fibroblast culture with different concentrations (300-500 µg/L) of oxidized zinc extract at different ratios extract/skin cells (1:1, 2:1, 3:1, 5:4) (Zn device extract:skin cells) with 5:4 as the preferred ratio. This mixture was then exposed to UV-B radiation (302 nm) for different times and incubated at 37° C. and 5% of $CO_2$. Each experiment was performed in triplicate.

Aliquots of fibroblast cells were harvested and subjected to microscopic analysis. Standard procedures were used to count dead, live, and apoptotic cells by staining the cells with trypan blue (1:1, trypan:sample) and viewing them under a compound microscope. Cells were counted at 20× magnification using several (16 each time) microscopic field views. Results are presented as the average of these 16 microscopic optical field samples.

Results

Results are presented in Tables 14 and 15 as the average of these 16 microscopic optical field samples. Alive cells are elongated without blue pigmentation. Dead cells are spherical with intense blue pigmentation. Apoptotic cells are slightly curved with slight or no light blue pigmentation. Initial Culture of Fibroblast Cells: alive cells: 87; death cells: 3; apoptotic cells: 3

When sunlight passes through the atmosphere, the ozone, water vapor, oxygen and carbon dioxide absorb approximately 90% of UVB radiation, hence reducing the amount of exposure to UVB radiation; however, this UVB wavelength also causes damage to human skin. (World Health Organization/WHO/SDE/OEH/02.2, 2003). As shown in the tables below, the oxidized zinc is highly effective in protecting the skin against UVB radiation, considering that the anti-UVB experiments were performed under continued direct exposure to UVB radiation for the entire time of the experiment.

TABLE 14

Number of alive, dead and apoptotic fibroblast cells at different times.
Protective effect of Zinc Device on SC,
Against UV-B at different times

| | SCC + Water (Control) | | | SCC + Zn Device (Treatment) | | |
|---|---|---|---|---|---|---|
| Type of cell | 45 minutes | 2 hour | 4 hour | 45 minutes | 2 hour | 4 hour |
| Alive Cells (average) | 40 | 3 | 0 | 51 | 22 | 14 |
| Dead Cells (average) | 3 | 18 | 13 | 3 | 5 | 4 |
| Apoptotic Cells (average) | 3 | 0 | 0 | 5 | 8 | 6 |

TABLE 15

Percentage of alive, dead and apoptotic fibroblast cells at different times.
Protective effect of Zinc Device on SC,
Against UV-B at different times

| Type of cell | SCC + Water (Control) | | | SCC + Zn Device (Treatment) | | |
|---|---|---|---|---|---|---|
| | 45 minutes | 2 hour | 4 hour | 45 minutes | 2 hour | 4 hour |
| Alive Cells (Percentage) | 86 | 14 | 0 | 86 | 63 | 58 |
| Dead Cells (Percentage) | 7 | 86 | 100 | 5 | 14 | 17 |
| Apopoptotic Cells (Percentage) | 7 | 0 | 0 | 8 | 23 | 25 |

Throughout this application, various publications are referenced. The disclosures of these publications in their entireties are hereby incorporated by reference into this application in order to more fully describe the compounds, compositions, and methods described herein.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed:

1. A DNA construct comprising the following genetic components:
   a. a gene that expresses zinc-related protein;
   b. a gene that expresses alkaline phosphatase; and
   c. a gene that expresses alcohol dehydrogenase.

2. The DNA construct of claim 1, wherein the gene that expresses zinc-related protein has SEQ ID NO. 1 or at least 70% homology thereto.

3. The DNA construct of claim 1, wherein the gene that expresses alkaline phosphatase has SEQ ID NO. 2 or at least 70% homology thereto.

4. The DNA construct of claim 1, wherein the gene that expresses alcohol dehydrogenase has SEQ ID NO. 3 or at least 70% homology thereto.

5. The DNA construct of claim 1, wherein the DNA construct further comprises a gene that expresses lipase.

6. The DNA construct of claim 5, wherein the gene that expresses lipase has SEQ ID NO. 6 or at least 70% homology thereto.

7. The DNA construct of claim 1, further comprising a GAL1 promoter is positioned before the gene that expresses zinc-related protein, the gene that expresses alkaline phosphatase, and the gene that expresses alcohol dehydrogenase.

8. The DNA construct of claim 1, wherein the DNA construct comprises from 5' to 3' the following genetic components in the following order: (a) a gene that expresses a zinc-related protein, (b) a gene that expresses an alkaline phosphatase, and (c) a gene that expresses an alcohol dehydrogenase.

9. The DNA construct of claim 1, wherein the DNA construct comprises from 5' to 3' the following genetic components in the following order: (a) a gene that expresses a zinc-related protein, (b) a gene that expresses a lipase, (c) a gene that expresses an alkaline phosphatase, and (d) a gene that expresses an alcohol dehydrogenase.

10. The DNA construct of claim 1, wherein the DNA construct comprises from 5' to 3' the following genetic components in the following order: (a) a GAL1 promoter, (b) a gene that expresses a zinc-related protein, (c) a CYC1 terminator, (d) a GAL1 promoter, (e) a gene that expresses an alkaline phosphatase, (f) a CYC1 terminator, (g) a GAL1 promoter, (h) a gene that expresses an alcohol dehydrogenase, (i) a CYC1 terminator.

11. The DNA construct of claim 1, wherein the DNA construct comprises from 5' to 3' the following genetic components in the following order: (a) a gene that expresses a zinc-related protein, (b) a CYC1 terminator, (c) a GAL1 promoter, (d) a gene that expresses a lipase, (e) a CYC1 terminator, (f) a GAL1 promoter, (g) a gene that expresses an alkaline phosphatase, (h) a CYC1 terminator, (i) a GAL1 promoter, (j) a gene that expresses an alcohol dehydrogenase, and (k) a CYC1 terminator.

12. The DNA construct of claim 1, wherein the DNA construct comprises from 5' to 3' the following genetic components in the following order: (a) a GAL1 promoter, (b) a gene that expresses a zinc-related protein having SEQ ID NO. 1 or at least 70% homology thereto, (c) a CYC1 terminator, (d) a GAL1 promoter, (e) a gene that expresses an alkaline phosphatase having SEQ ID NO. 2 or at least 70% homology thereto, (f) a CYC1 terminator, (g) a GAL1 promoter, (h) a gene that expresses an alcohol dehydrogenase having SEQ ID NO. 3 or at least 70% homology thereto, and (i) a CYC1 terminator.

13. The DNA construct of claim 1, wherein the DNA construct comprises from 5' to 3' the following genetic components in the following order: (a) a gene that expresses a zinc-related protein having SEQ ID NO. 1 or at least 70% homology thereto, (b) a CYC1 terminator, (c) a GAL1 promoter, (d) a gene that expresses a lipase having SEQ ID NO. 6, (e) a CYC1 terminator, (f) a GAL1 promoter, (g) a gene that expresses an alkaline phosphatase having SEQ ID NO. 2 or at least 70% homology thereto, (h) a CYC1 terminator, (i) a GAL1 promoter, (j) a gene that expresses an alcohol dehydrogenase having SEQ ID NO. 3 or at least 70% homology thereto, and (k) a CYC1 terminator.

14. The DNA construct of claim 1, wherein the DNA construct has SEQ ID NO. 5 or at least 70% homology thereto.

15. The DNA construct of claim 5, wherein the DNA construct has SEQ ID NO. 7 or at least 70% homology thereto.

16. A vector comprising the DNA construct of claim 1.

17. The vector of claim 16, wherein the vector is a plasmid.

18. The vector of claim 17, wherein the plasmid is pWLneo, pSV2cat, pOG44, pXT1, pSG, pSVK3, pBSK, pBSKII, pYES, pYES2, pUC, or pUC19.

19. A biological device comprising host cells transformed with the DNA construct of claim 1.

20. The biological device of claim 19, wherein the host cells comprise fungi or bacteria.

* * * * *